(12) United States Patent
Haines

(10) Patent No.: US 7,815,645 B2
(45) Date of Patent: Oct. 19, 2010

(54) METHODS AND APPARATUS FOR PINPLASTY BONE RESECTION

(75) Inventor: Timothy G. Haines, Seattle, WA (US)

(73) Assignee: Hudson Surgical Design, Inc., Seattle, WA (US)

( * ) Notice: Subject to any disclaimer, the term of this patent is extended or adjusted under 35 U.S.C. 154(b) by 210 days.

(21) Appl. No.: 11/036,584

(22) Filed: Jan. 14, 2005

(65) Prior Publication Data

US 2006/0030853 A1 Feb. 9, 2006

Related U.S. Application Data

(60) Provisional application No. 60/536,320, filed on Jan. 14, 2004, provisional application No. 60/540,992, filed on Feb. 2, 2004, provisional application No. 60/551,080, filed on Mar. 8, 2004, provisional application No. 60/551,078, filed on Mar. 8, 2004, provisional application No. 60/551,096, filed on Mar. 8, 2004, provisional application No. 60/551,631, filed on Mar. 8, 2004, provisional application No. 60/551,307, filed on Mar. 8, 2004, provisional application No. 60/551,262, filed on Mar. 8, 2004, provisional application No. 60/551,160, filed on Mar. 8, 2004.

(51) Int. Cl.
 *A61B 5/00* (2006.01)
(52) U.S. Cl. .................................................. 606/86 R
(58) Field of Classification Search .................. 606/79, 606/82, 86, 87–89; 623/911, 20.14
See application file for complete search history.

(56) References Cited

U.S. PATENT DOCUMENTS

| 3,739,662 A | 6/1973 | Windelman et al. |
| 3,774,244 A | 11/1973 | Walker |
| 3,798,679 A | 3/1974 | Ewald |

(Continued)

FOREIGN PATENT DOCUMENTS

EP 0189253 7/1986

(Continued)

OTHER PUBLICATIONS

*Hudson Surgical Design v. Zimmer Holdings, Inc., et al.*, Zimmer, Inc.'s and Zimmer Holding Inc's Supplemental Responses to Hudson Surgical Design, Inc.'s First Set of Interrogatories (Nos. 1-18) To Each of Them, dated Aug. 1, 2008.

(Continued)

*Primary Examiner*—Thomas C Barrett
*Assistant Examiner*—Michael J Araj
(74) *Attorney, Agent, or Firm*—Patterson, Thuente, Skaar & Christensen, P.A.

(57) ABSTRACT

Methods and apparatus for performing arthoplasty utilizes a plurality of apertures created in a bone, each aperture having a cross section defined perpendicular to an axis of the aperture that intersects a plane of a resected surface to be created in the bone and also intersects a peripheral rim border that externally delineates the resected surface. A pin feature is inserted into each of the plurality of apertures and the resected surface is created by guiding a cutting tool along at least a line of contact of the pin features. An implant can then be attached to the resected surface.

13 Claims, 61 Drawing Sheets

U.S. PATENT DOCUMENTS

| | | |
|---|---|---|
| 3,816,855 A | 6/1974 | Salch |
| 3,906,550 A | 9/1975 | Rostoker |
| 3,953,899 A | 5/1976 | Charnley |
| 4,069,824 A | 1/1978 | Weinstock |
| 4,178,641 A | 12/1979 | Gruendel |
| 4,340,978 A | 7/1982 | Buechel |
| 4,349,058 A | 9/1982 | Comparetto |
| 4,353,135 A | 10/1982 | Forte |
| 4,358,859 A | 11/1982 | Schurman et al. |
| 4,421,112 A * | 12/1983 | Mains et al. .................. 606/88 |
| 4,457,307 A | 7/1984 | Stillwell |
| 4,474,177 A | 10/1984 | Whiteside |
| 4,479,271 A | 10/1984 | Bolesky |
| 4,487,203 A | 12/1984 | Androphy |
| 4,501,266 A | 2/1985 | McDaniel |
| 4,502,483 A | 3/1985 | Lacey |
| 4,524,766 A | 6/1985 | Petersen |
| 4,566,448 A | 1/1986 | Rohr, Jr. |
| 4,567,886 A | 2/1986 | Peterson |
| 4,568,348 A | 2/1986 | Johnson et al. |
| 4,586,496 A | 5/1986 | Keller |
| 4,586,933 A | 5/1986 | Shoji et al. |
| 4,653,488 A | 3/1987 | Kenna |
| 4,659,331 A | 4/1987 | Matthews |
| 4,662,889 A | 5/1987 | Zichner |
| 4,693,721 A | 9/1987 | Ducheyne |
| 4,709,699 A | 12/1987 | Michael |
| 4,714,473 A | 12/1987 | Bloebaum |
| 4,718,413 A | 1/1988 | Johnson |
| 4,721,104 A | 1/1988 | Kaufman |
| 4,722,330 A | 2/1988 | Russell |
| 4,731,086 A | 3/1988 | Whiteside |
| 4,736,086 A | 4/1988 | Obara |
| 4,736,737 A | 4/1988 | Fargie |
| 4,738,256 A | 4/1988 | Freeman |
| 4,759,350 A | 7/1988 | Dunn |
| 4,770,663 A | 9/1988 | Hanslik |
| 4,787,383 A | 11/1988 | Kenna |
| 4,822,365 A | 4/1989 | Walker |
| 4,841,975 A | 6/1989 | Woolson |
| 4,880,429 A | 11/1989 | Stone |
| 4,892,093 A | 1/1990 | Zarnowski |
| 4,896,663 A | 1/1990 | Vandewalle |
| 4,919,667 A | 4/1990 | Richmond |
| 4,938,762 A | 7/1990 | Wehrli |
| 4,952,213 A | 8/1990 | Bowman |
| 4,971,075 A | 11/1990 | Lee |
| 5,002,545 A | 3/1991 | Whiteside |
| 5,002,547 A | 3/1991 | Poggie |
| 5,007,934 A | 4/1991 | Stone |
| 5,021,056 A | 6/1991 | Hofman |
| 5,032,134 A | 7/1991 | Lindwer |
| 5,041,138 A | 8/1991 | Vacanti |
| 5,047,032 A | 9/1991 | Jellicoe |
| 5,049,149 A | 9/1991 | Schmidt |
| 5,053,037 A | 10/1991 | Lackey |
| 5,092,869 A | 3/1992 | Waldron |
| 5,098,436 A | 3/1992 | Ferrante |
| 5,100,409 A | 3/1992 | Coates |
| 5,112,336 A | 5/1992 | Krevolin |
| 5,122,144 A | 6/1992 | Bert |
| 5,129,909 A | 7/1992 | Sutherland |
| 5,147,365 A | 9/1992 | Whitlock |
| 5,176,710 A | 1/1993 | Hahn |
| 5,190,547 A | 3/1993 | Barber, Jr. |
| 5,206,023 A | 4/1993 | Hunziker |
| 5,226,916 A | 7/1993 | Goodfellow |
| 5,228,459 A | 7/1993 | Caspari |
| 5,234,432 A | 8/1993 | Brown |
| 5,234,433 A | 8/1993 | Bert |
| 5,236,875 A | 8/1993 | Trigg |
| 5,250,050 A | 10/1993 | Poggie |
| 5,263,498 A | 11/1993 | Caspari |
| 5,269,786 A | 12/1993 | Morgan |
| 5,284,482 A | 2/1994 | Mikhail |
| 5,304,181 A | 4/1994 | Caspari |
| 5,306,276 A | 4/1994 | Johnson |
| 5,314,482 A | 5/1994 | Goodfellow |
| 5,342,368 A | 8/1994 | Peterson |
| 5,358,527 A | 10/1994 | Forte |
| 5,358,529 A | 10/1994 | Davidson |
| 5,364,401 A | 11/1994 | Ferrante |
| 5,364,402 A * | 11/1994 | Mumme et al. ................ 606/88 |
| 5,370,699 A | 12/1994 | Hood |
| 5,454,816 A | 10/1995 | Ashby |
| 5,462,551 A | 10/1995 | Bailey |
| 5,470,335 A | 11/1995 | Du Toit |
| 5,474,559 A | 12/1995 | Bertin |
| 5,514,136 A | 5/1996 | Richelsoph |
| 5,514,139 A | 5/1996 | Goldstein et al. |
| 5,514,143 A | 5/1996 | Bonutti |
| 5,520,695 A * | 5/1996 | Luckman ..................... 606/88 |
| 5,540,695 A | 7/1996 | Levy |
| 5,542,947 A | 8/1996 | Treacy |
| 5,571,100 A | 11/1996 | Goble |
| 5,578,039 A | 11/1996 | Vendrely |
| 5,593,411 A | 1/1997 | Stalcup |
| 5,597,379 A | 1/1997 | Haines et al. |
| 5,601,563 A | 2/1997 | Burke |
| 5,611,802 A | 3/1997 | Samuelson |
| 5,628,749 A | 5/1997 | Vendrely |
| 5,643,272 A * | 7/1997 | Haines et al. ................. 606/80 |
| 5,643,402 A | 7/1997 | Schmid |
| 5,649,928 A | 7/1997 | Grundei |
| 5,653,714 A | 8/1997 | Dietz |
| 5,658,293 A | 8/1997 | Vanlaningham |
| 5,667,511 A | 9/1997 | Vendrely |
| 5,682,886 A | 11/1997 | Delp |
| 5,690,635 A | 11/1997 | Matsen, III |
| 5,690,637 A | 11/1997 | Wen |
| 5,697,935 A | 12/1997 | Moran |
| 5,723,016 A | 3/1998 | Minns |
| 5,725,530 A | 3/1998 | Popken |
| 5,755,803 A | 5/1998 | Haines |
| 5,769,855 A | 6/1998 | Bertin |
| 5,769,899 A | 6/1998 | Schwartz |
| 5,799,055 A | 8/1998 | Peshkin et al. |
| 5,810,827 A | 9/1998 | Haines et al. |
| 5,824,105 A | 10/1998 | Ries |
| 5,871,546 A | 2/1999 | Colleran |
| 5,879,354 A | 3/1999 | Haines |
| 5,906,643 A | 5/1999 | Walker |
| 5,980,526 A | 11/1999 | Johnson |
| 5,986,169 A | 11/1999 | Gjunter |
| 6,039,764 A | 3/2000 | Pottenger |
| 6,056,754 A | 5/2000 | Haines |
| 6,059,788 A | 5/2000 | Katz |
| 6,132,468 A | 10/2000 | Mansmann |
| 6,171,340 B1 | 1/2001 | McDowell |
| 6,197,064 B1 | 3/2001 | Haines |
| 6,236,875 B1 | 5/2001 | Bucholz et al. |
| 6,285,902 B1 | 9/2001 | Kienzle et al. |
| 6,340,363 B1 | 1/2002 | Bolger et al. |
| 6,342,075 B1 | 1/2002 | MacArthur |
| 6,348,058 B1 | 2/2002 | Melkent et al. |
| 6,368,353 B1 | 4/2002 | Arcand |
| 6,375,658 B1 | 4/2002 | Hangody |
| 6,401,346 B1 | 6/2002 | Roberts |
| 6,430,434 B1 | 8/2002 | Mittelstadt |
| 6,458,128 B1 | 10/2002 | Schulze |
| 6,470,207 B1 | 10/2002 | Simon et al. |
| 6,477,400 B1 | 11/2002 | Barrick |
| 6,482,209 B1 | 11/2002 | Engh et al. |
| 6,491,699 B1 | 12/2002 | Henderson et al. |

| | | |
|---|---|---|
| 6,520,964 B2 | 2/2003 | Tallarida |
| 6,554,838 B2 | 4/2003 | McGovern |
| 6,575,980 B1 | 6/2003 | Robie |
| 6,579,290 B1 | 6/2003 | Hardcastle |
| 6,595,997 B2 | 7/2003 | Axelson et al. |
| 6,672,224 B2 | 1/2004 | Weber et al. |
| 6,679,917 B2 | 1/2004 | Ek |
| 6,685,711 B2 | 2/2004 | Axelson et al. |
| 6,694,168 B2 | 2/2004 | Traxel et al. |
| 6,694,768 B2 | 2/2004 | Lu |
| 6,695,848 B2 | 2/2004 | Haines |
| 6,697,664 B2 | 2/2004 | Kienzle et al. |
| 6,701,174 B1 | 3/2004 | Krause et al. |
| 6,702,821 B2 | 3/2004 | Bonutti |
| 6,711,432 B1 | 3/2004 | Krause et al. |
| 6,725,080 B2 | 4/2004 | Melkent et al. |
| 6,783,550 B2 | 8/2004 | MacArthur |
| 6,796,988 B2 | 9/2004 | Melkent et al. |
| 6,827,723 B2 | 12/2004 | Carson |
| 6,858,032 B2 | 2/2005 | Chow |
| 6,875,222 B2 | 4/2005 | Long |
| 6,898,858 B1 | 5/2005 | Spell |
| 6,916,324 B2 | 7/2005 | Sanford |
| 6,942,627 B2 | 9/2005 | Huitema |
| 6,942,694 B2 | 9/2005 | Liddicoat |
| 7,018,418 B2 | 3/2006 | Amrich |
| 7,077,867 B1 | 7/2006 | Pope |
| 7,104,966 B2 | 9/2006 | Shilber |
| 7,141,053 B2 | 11/2006 | Rosa |
| 7,172,596 B2 | 2/2007 | Coon |
| 7,326,252 B2 | 2/2008 | Otto |
| 7,344,541 B2 | 3/2008 | Haines |
| 7,422,605 B2 | 9/2008 | Burstein |
| 7,491,235 B2 | 2/2009 | Fell |
| 2001/0044627 A1 | 11/2001 | Justin |
| 2003/0028196 A1 | 2/2003 | Bonutti |
| 2003/0069585 A1 | 4/2003 | Axelson et al. |
| 2003/0069591 A1 | 4/2003 | Carson et al. |
| 2003/0075564 A1* | 4/2003 | Wahlig et al. ............... 222/206 |
| 2003/0130665 A1 | 7/2003 | Pinczewski et al. |
| 2003/0181986 A1* | 9/2003 | Buchholz ................ 623/22.12 |
| 2003/0208122 A1 | 11/2003 | Melkent et al. |
| 2003/0212403 A1 | 11/2003 | Swanson |
| 2003/0212413 A1 | 11/2003 | Wilk |
| 2004/0039396 A1 | 2/2004 | Couture et al. |
| 2004/0122305 A1* | 6/2004 | Grimm et al. ............... 600/407 |
| 2004/0122436 A1 | 6/2004 | Grimm |
| 2004/0152970 A1 | 8/2004 | Hunter et al. |
| 2004/0153066 A1 | 8/2004 | Coon et al. |
| 2004/0153083 A1* | 8/2004 | Nemec et al. ................ 606/86 |
| 2004/0153085 A1 | 8/2004 | Farling et al. |
| 2004/0249471 A1 | 12/2004 | Bindseil |
| 2005/0149038 A1 | 7/2005 | Haines |
| 2005/0149039 A1 | 7/2005 | Haines |
| 2005/0149040 A1 | 7/2005 | Haines |
| 2005/0171604 A1 | 8/2005 | Michalow |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero |
| 2006/0058882 A1 | 3/2006 | Haines |
| 2007/0078517 A1 | 4/2007 | Engh |
| 2007/0179607 A1 | 8/2007 | Hodorek |
| 2008/0154270 A1 | 6/2008 | Haines |
| 2009/0076514 A1 | 3/2009 | Haines |
| 2009/0082773 A1 | 3/2009 | Haines |
| 2009/0138018 A1 | 5/2009 | Haines |

FOREIGN PATENT DOCUMENTS

| | | |
|---|---|---|
| EP | 0466659 A2 | 1/1992 |
| EP | 0538153 A1 | 4/1993 |
| EP | 0682916 A2 | 11/1995 |
| EP | 0761242 | 3/1997 |
| FR | 2664157 A1 | 1/1992 |
| GB | 2007980 | 7/1982 |
| JP | 2002/274214 | 11/1990 |
| SU | 577020 T | 10/1977 |
| WO | WO96/01588 | 1/1996 |
| WO | WO96/07361 A1 | 3/1996 |
| WO | WO 97/05827 | 2/1997 |
| WO | WO97/29703 A1 | 8/1997 |
| WO | WO97/29704 A1 | 8/1997 |
| WO | WO02/34310 | 5/2002 |
| WO | WO2004/069036 A2 | 8/2004 |
| WO | WO2004/070580 A2 | 8/2004 |
| WO | WO2004/100758 A2 | 11/2004 |
| WO | WO2004/100839 | 11/2004 |

OTHER PUBLICATIONS

*Hudson Surgical Design v. Zimmer Holdings, Inc., et al.*, Revised Final Claim Construction Chart, dated Mar. 11, 2009.

T.D.V. Cooke et al., *Universal Bone Cutting Device for Precision Knee Replacement Arthroplasty and Osteotomy*, 7 J. Biomed. Eng'g 45, 47, col. 2,11. 52-57 (1985).

E. Marlowe Goble and Daniel F. Justin, *Minimally invasive total knee replacement: principles and technique*, Orthop. Clin. N. Am. 35 (2004) 235-245.

Whiteside Ortholoc Total Knee System: Surgical Procedure, Dow Corning Wright, pp. WMT000001-WMT000040, Jun. 1985.

Zimmer, Insall/Burstein II, *Constrained Condylar: Modular Knee System*, Surgical Technique, Inc., copyright 1989.

Zimmer, The Miller/Galante Advantage: Total Knee System, pp. ZH000159653-ZH000159668.

File History for U.S. Appl. No. 12/187,210, filed Aug. 6, 2008.

File History for U.S. Appl. No. 11/075,842, filed Mar. 8, 2005.

File History for U.S. Appl. No. 11/075,828, filed Mar. 8, 2005.

File History for U.S. Appl. No. 11/074,599, filed Mar. 8, 2005.

U.S. Appl. No. 12/171,843, Inventor: Haines, filed Jul. 11, 2008.

U.S. Appl. No. 11/825,857, Inventor: Haines, filed Jul. 9, 2007.

U.S. Appl. No. 11/075,552, Inventor: Haines, filed Mar. 8, 2005.

File History for U.S. Appl. No. 11/075,840, filed Mar. 8, 2005.

File History for U.S. Appl. No. 11/075,553, filed Mar. 8, 2005.

File History for U.S. Appl. No. 11/049,634, filed Feb. 5, 2005.

File History for U.S. Appl. No. 11/075,836, filed Mar. 8, 2005.

Whiteside Ortholoc Total Knee System, Dow Coming Wright, pp. ZH000109679-ZH000109690.

Zimmer, Insall/Burstein II, *Modular Knee System*, Surgical Technique, Inc., pp. ZH000109691-ZH000109710.

* cited by examiner

ANTERIOR CUT SURFACE

OSCILLATING SAW

POSTERIOR CUT SURFACE

DISTAL CUT SURFACE

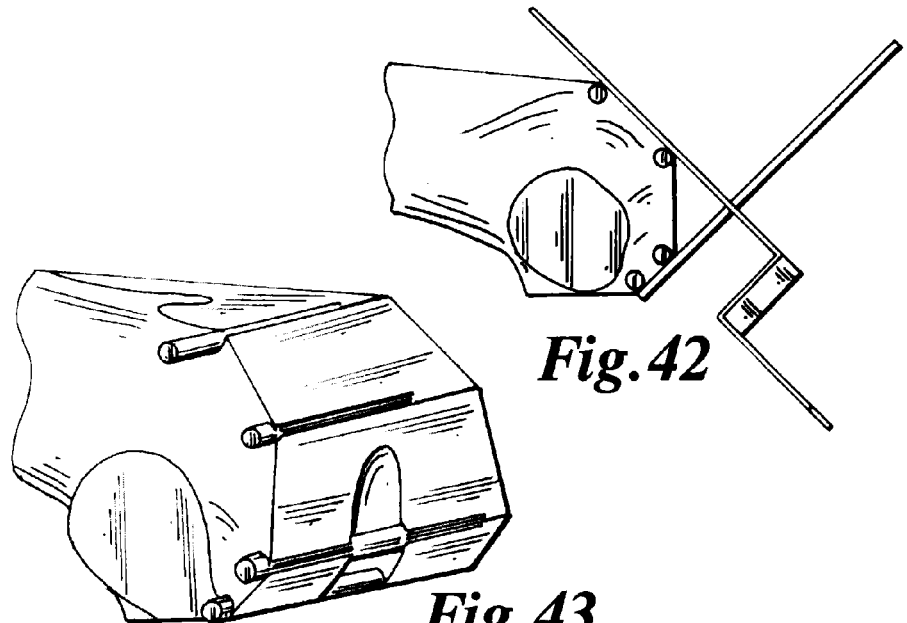
*Fig.42*
*Fig.43*
SUB SURFACE HOLES OR ARTIFACTS PERFECT FOR PMMA BONE CEMENT INJECTION AFTER PLACING THE IMPLANT ON THE BONE
MODULAR OR UNITARY GUIDE RAIL INTERCONNECTING THE PINS-COULD BE A SEPARATE COMPONENT CONNECTED TO THE PINS BEFORE OR AFTER THE PINS ARE ATTACHED TO THE BONE
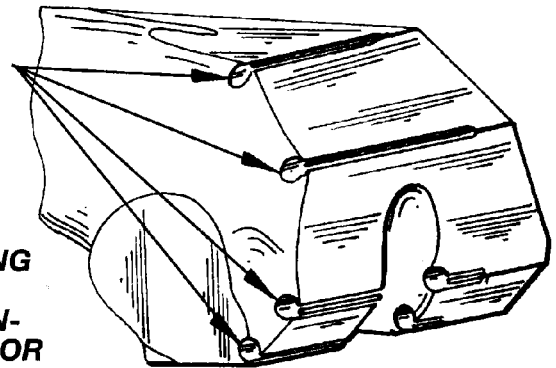
*Fig.44*
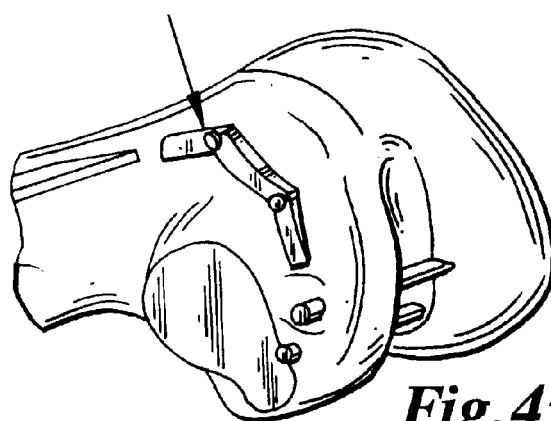
*Fig.45*

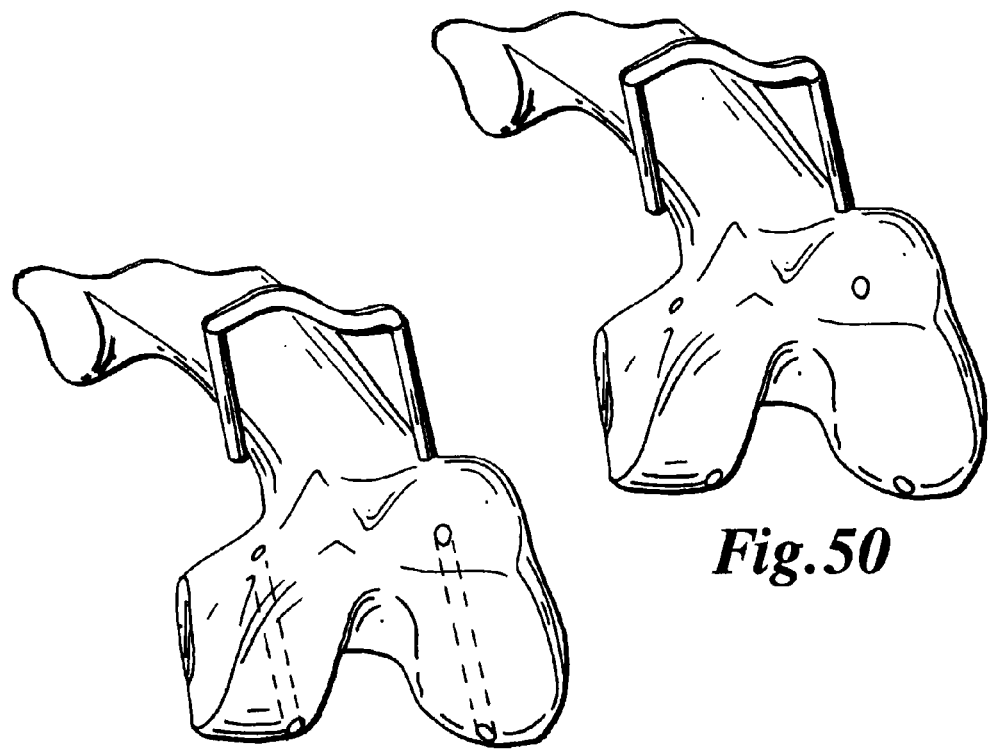
*Fig.50*
*Fig.51*
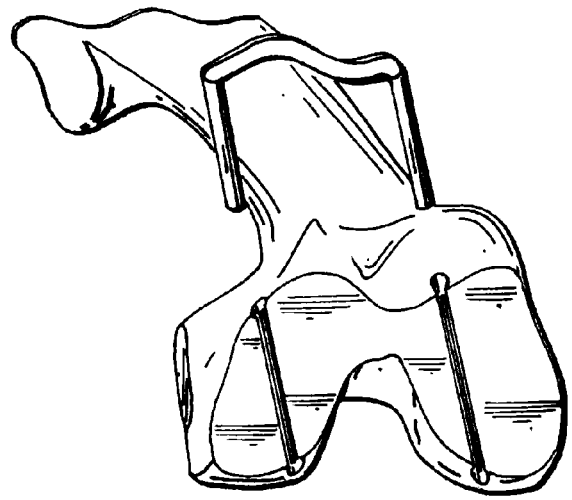
*Fig.52*

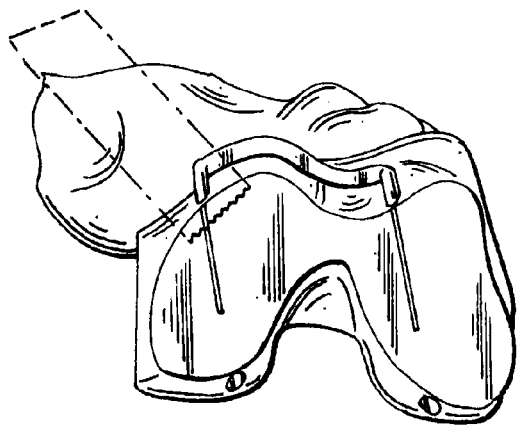
*Fig.61*
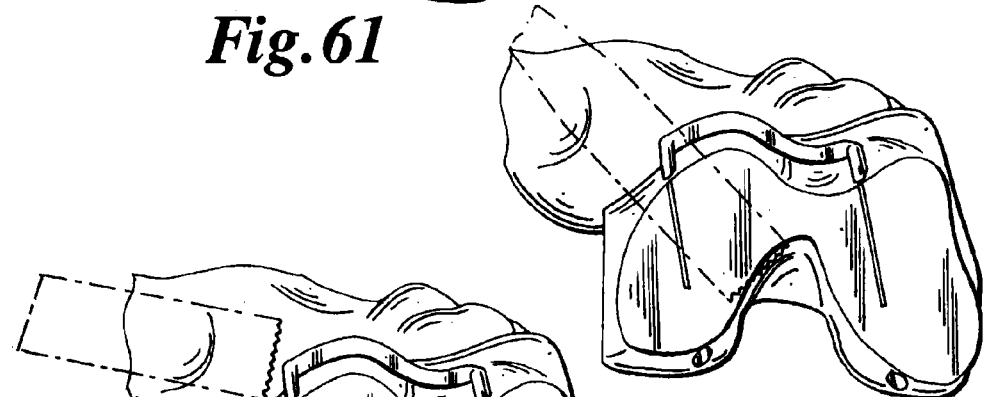
*Fig.62*
*Fig.63*
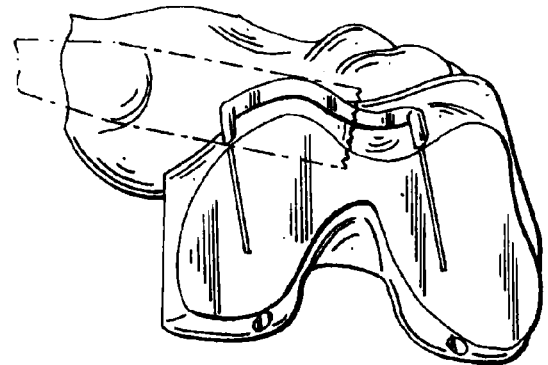
*Fig.64*

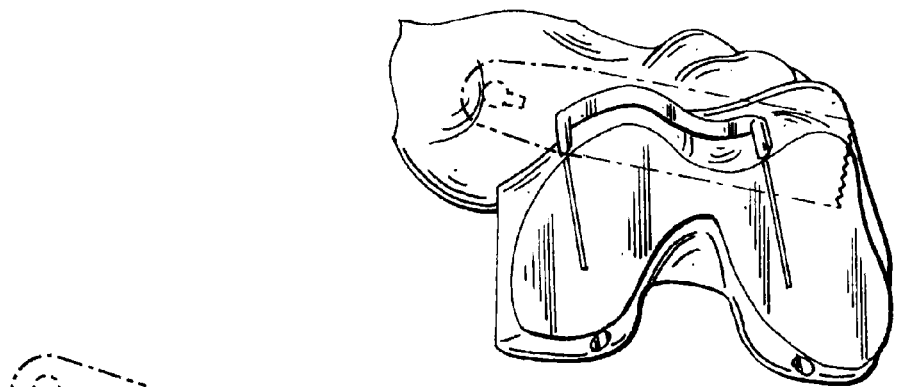
*Fig.65*
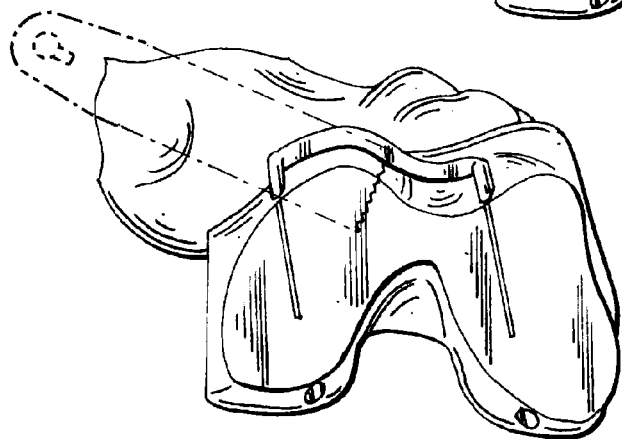
*Fig.66*
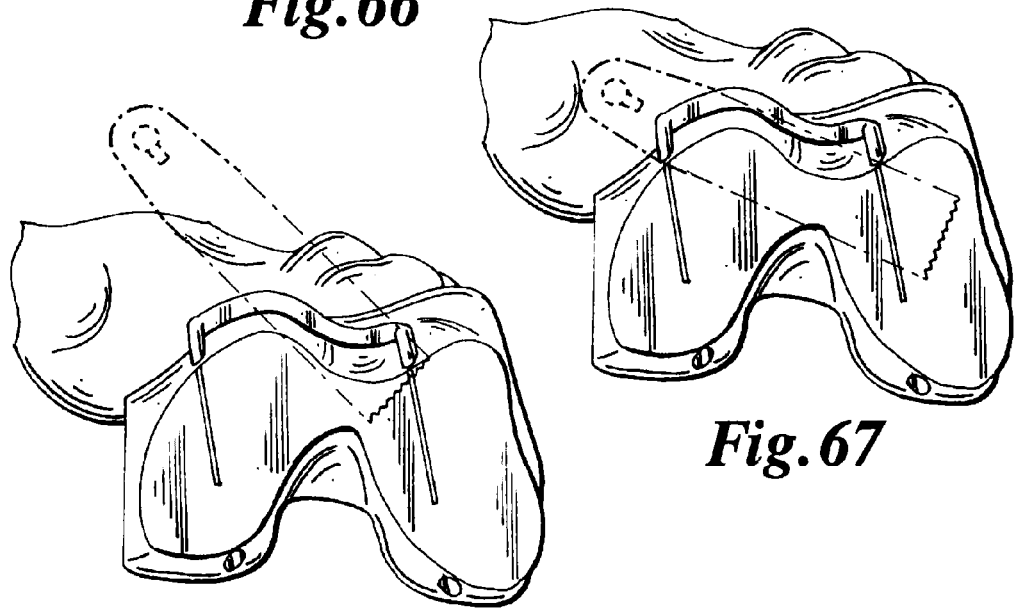
*Fig.67*
*Fig.68*

CUTTING TOOL CAPTURE

DISTAL CUT SURFACE TO BE CREATED

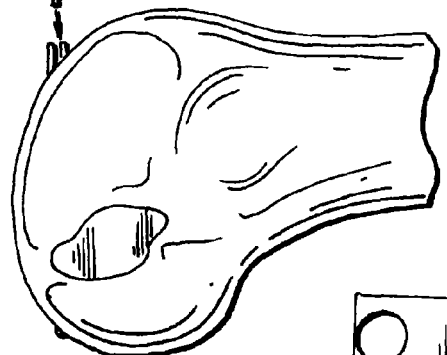
*Fig. 97*
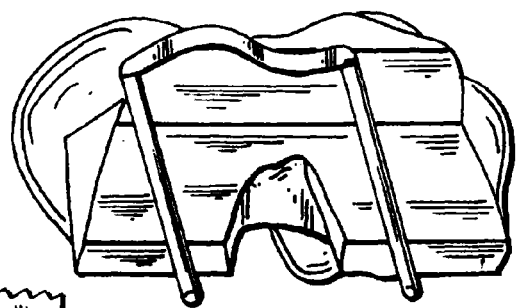
*Fig. 98*
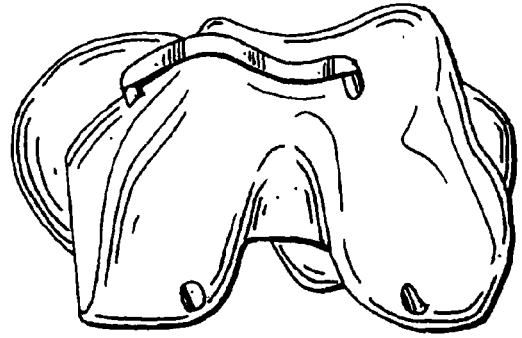
*Fig. 99*
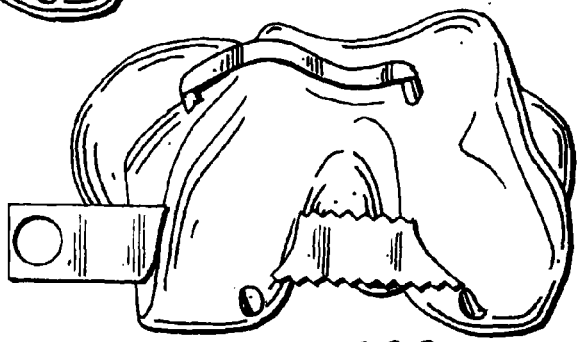
*Fig. 100*

ANTERIOR CUT DRILL HOLES
ANTERIOR CHAMFER CUT DRILL HOLES
POSTERIOR CHAMFER CUT DRILL HOLES
POSTERIOR CUT DRILL HOLES

FEMUR

DIVERGENT PIN SHOWN SEPERATE FROM GUIDE

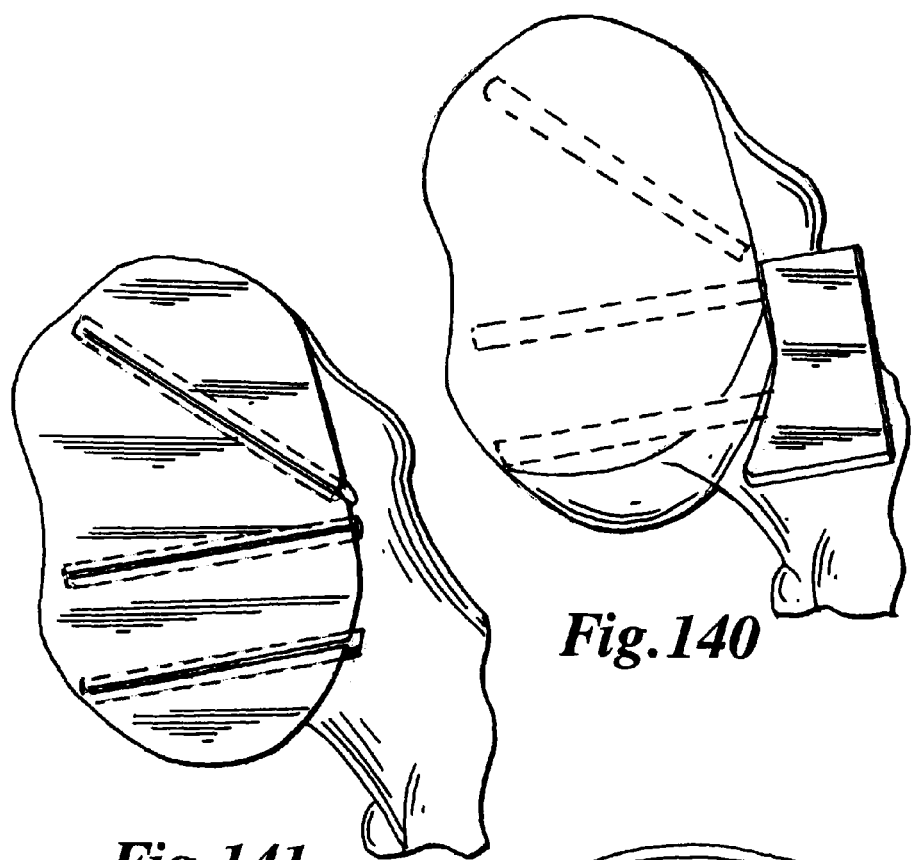
Fig.140
Fig.141
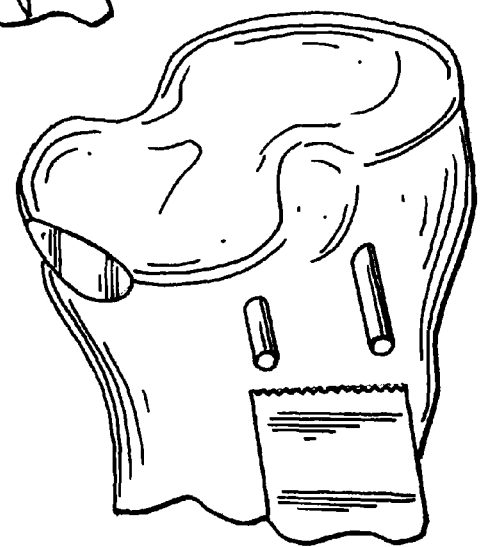
Fig.142

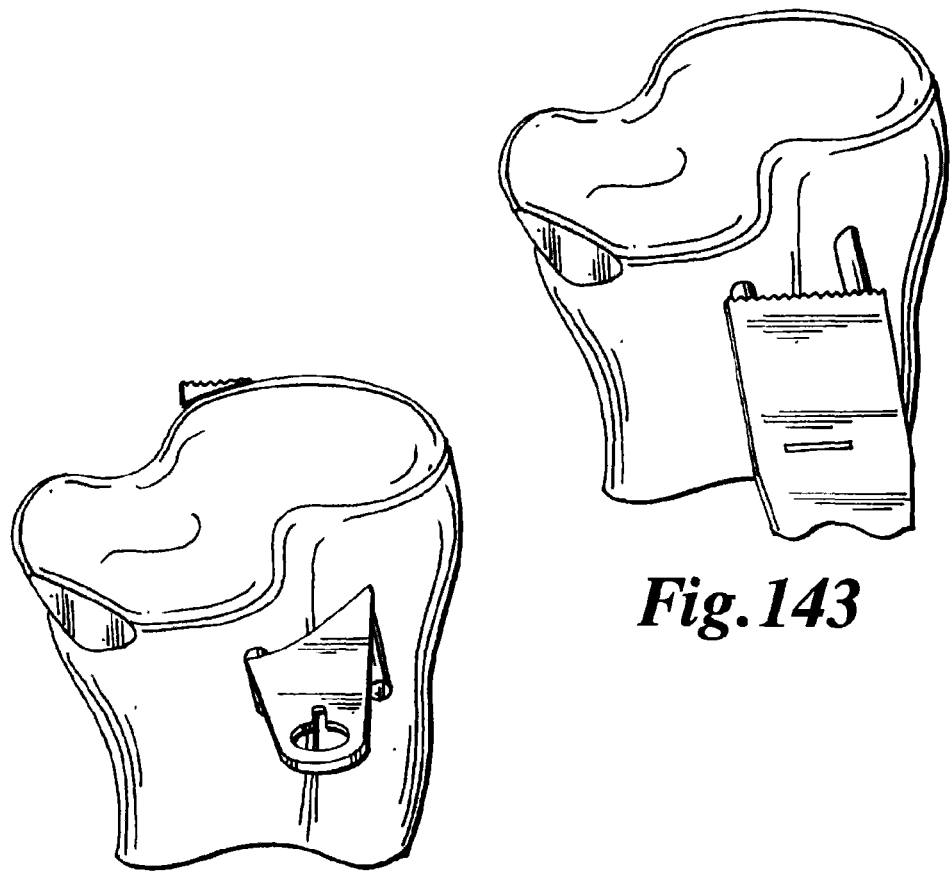
Fig.143
Fig.144
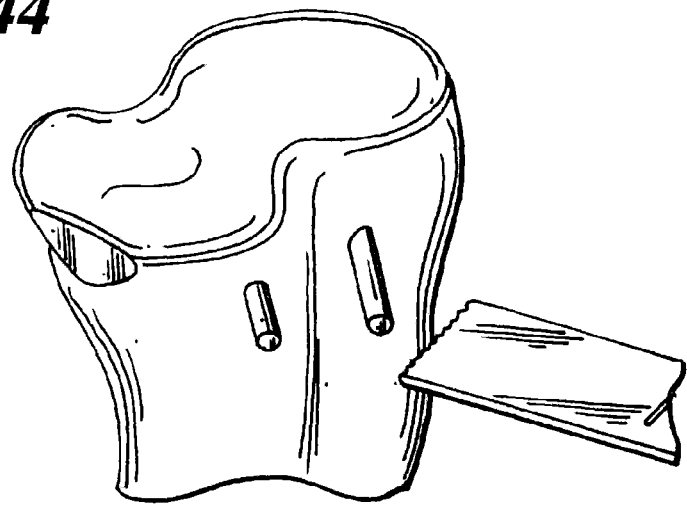
Fig.145

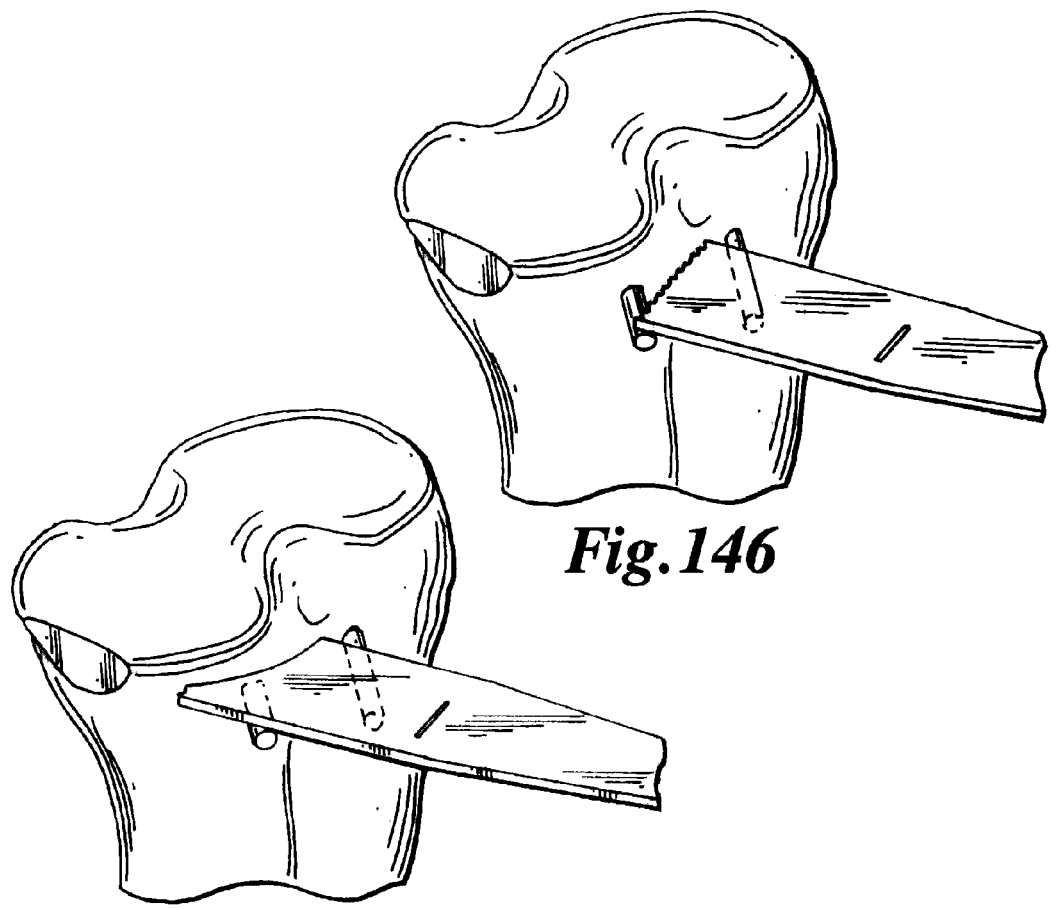
*Fig.146*
*Fig.147*
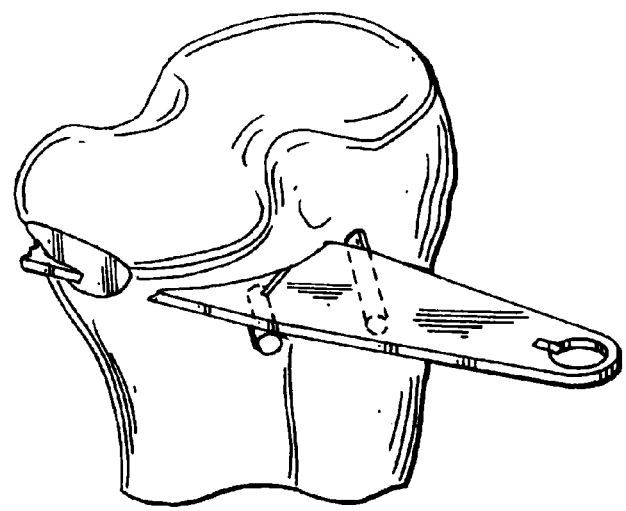
*Fig.148*

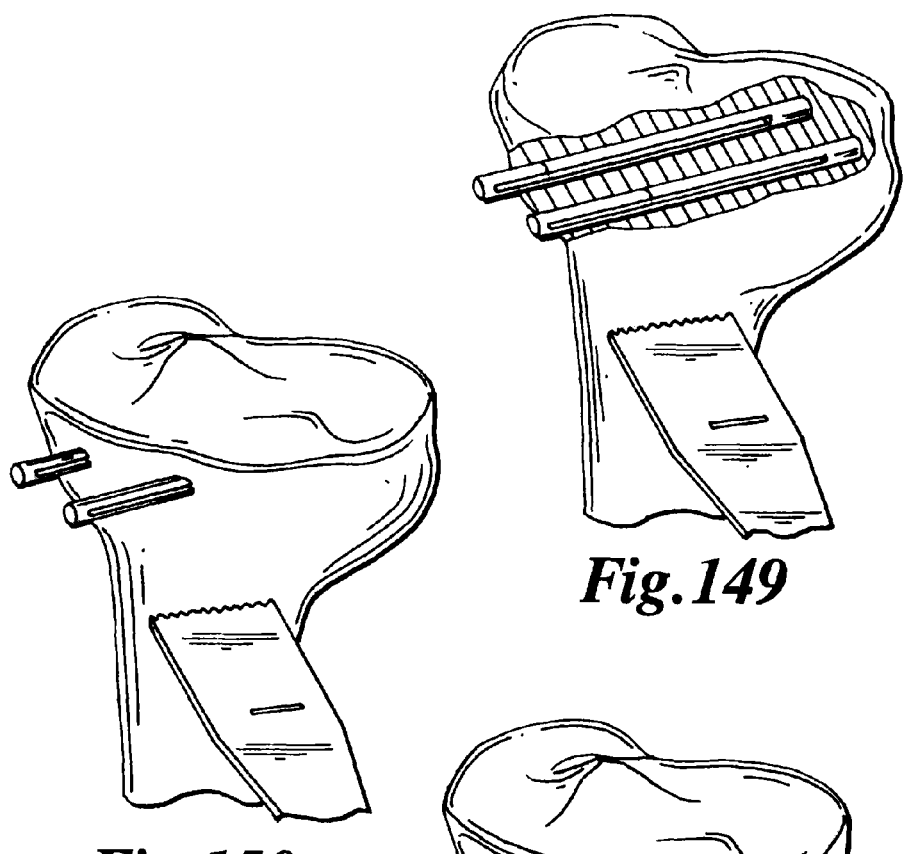
*Fig.149*
*Fig.150*
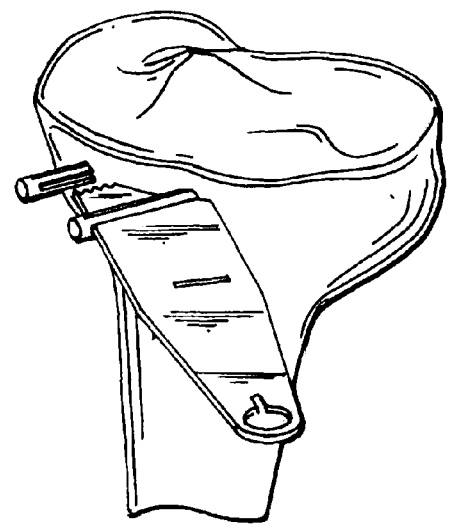
*Fig.151*

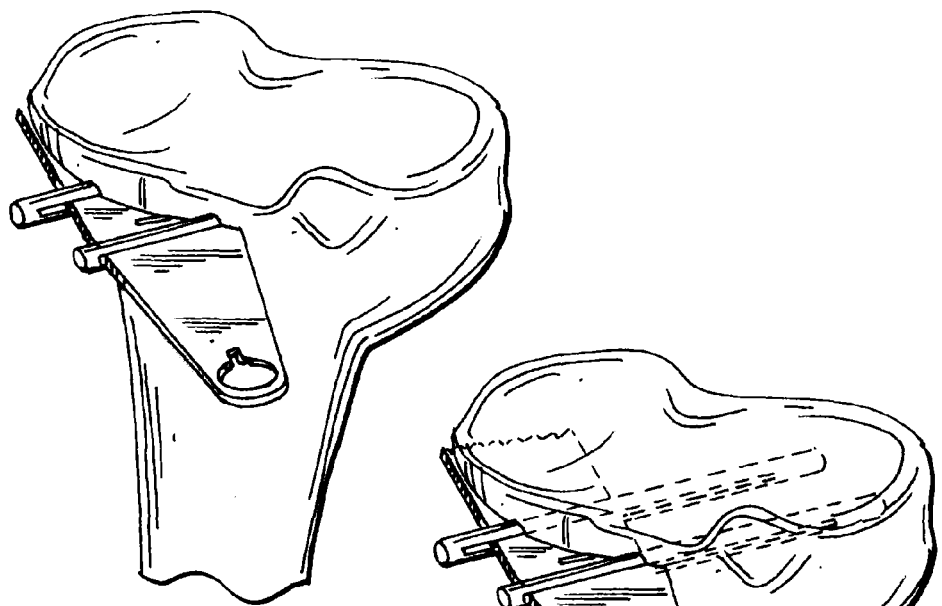
Fig.152
Fig.153
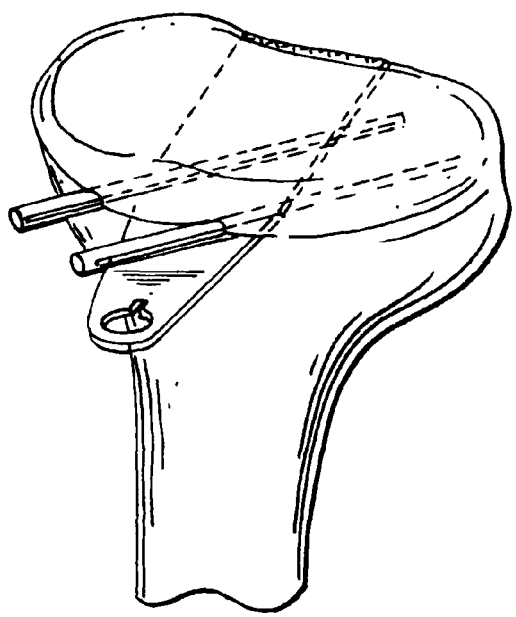
Fig.154

SPACING FEATURE
SPACING FEATURES

SPACING FEATURES
SPACING FEATURE

LOCKED POSITION

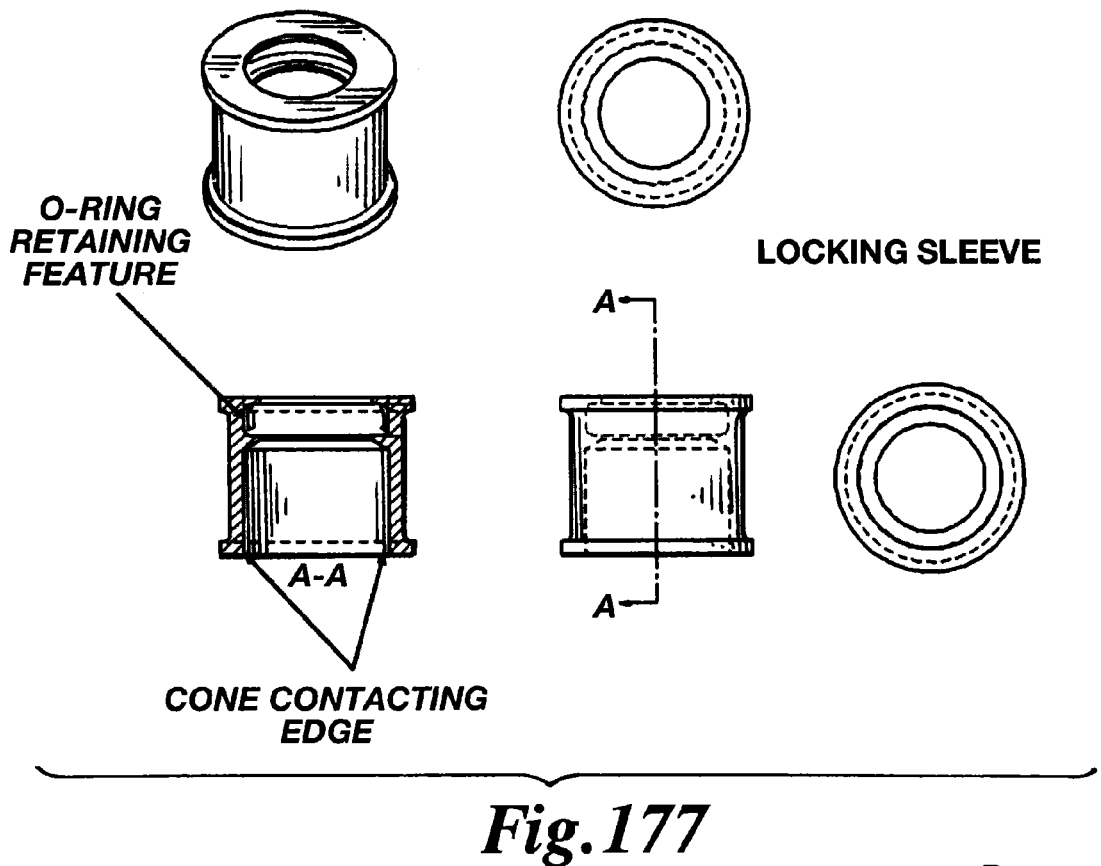
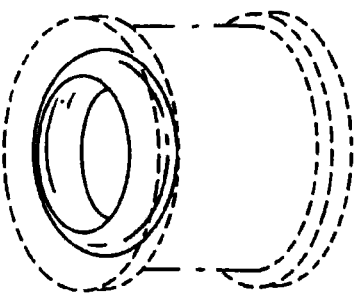
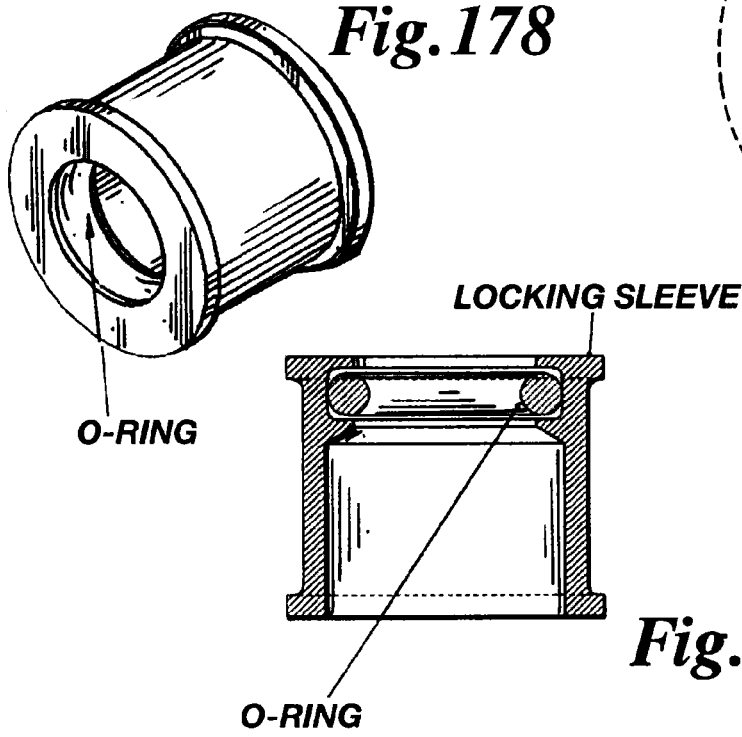
Fig. 177
Fig. 178
Fig. 179
Fig. 180

MALALIGNED IN 6 DEGREES OF FREEDOM WITH RESPECT TO THE DESIRED CUT LOCATION AND ORIENTATION

1. VARUS-VALGUS
2. FLEXION-EXTENSION
3. INTERNAL-EXTERNAL ROTATION
4. ANTERIOR-POSTERIOR
5. PROXIMAL-DISTAL
6. MEDIAL-LATERAL

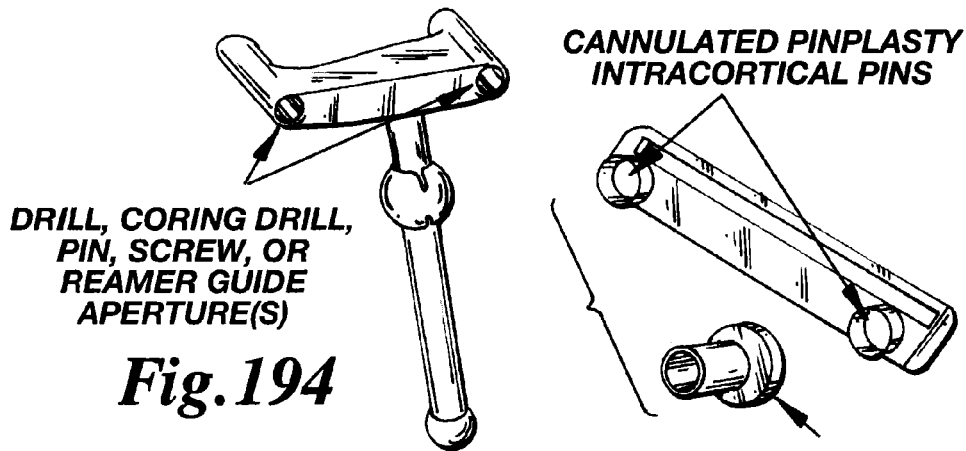
Fig.194 DRILL, CORING DRILL, PIN, SCREW, OR REAMER GUIDE APERTURE(S)
Fig.195 CANNULATED PINPLASTY INTRACORTICAL PINS / CORING DRILL: OD 0.15". ID 0.143"
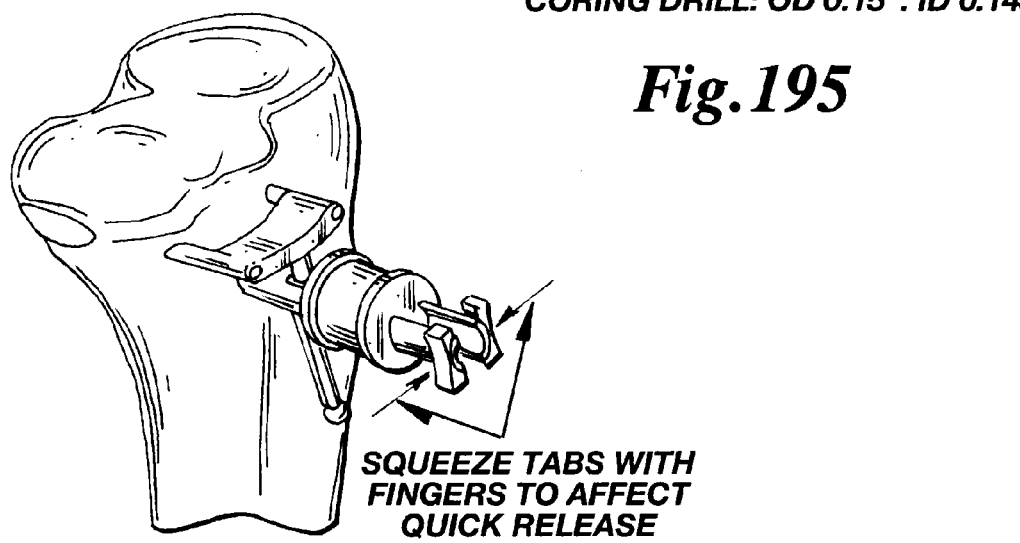
Fig.196 SQUEEZE TABS WITH FINGERS TO AFFECT QUICK RELEASE
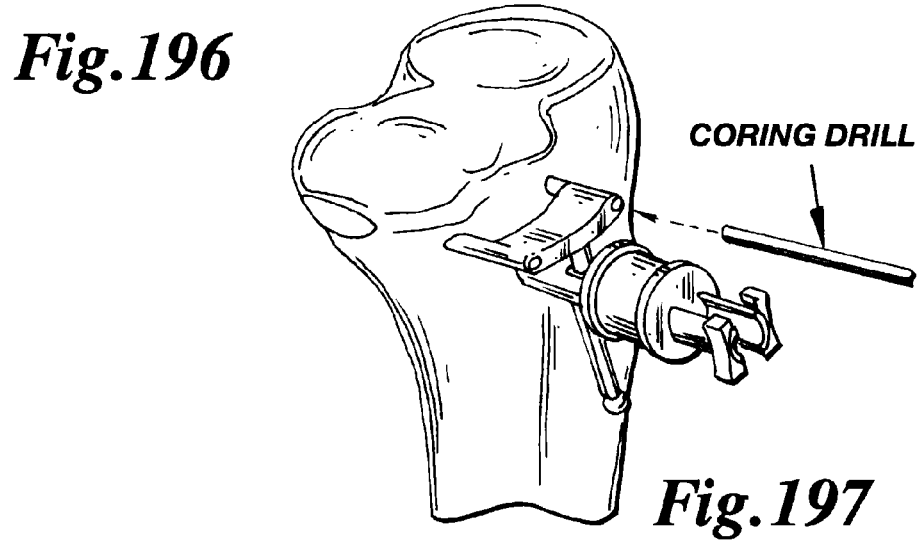
Fig.197 CORING DRILL

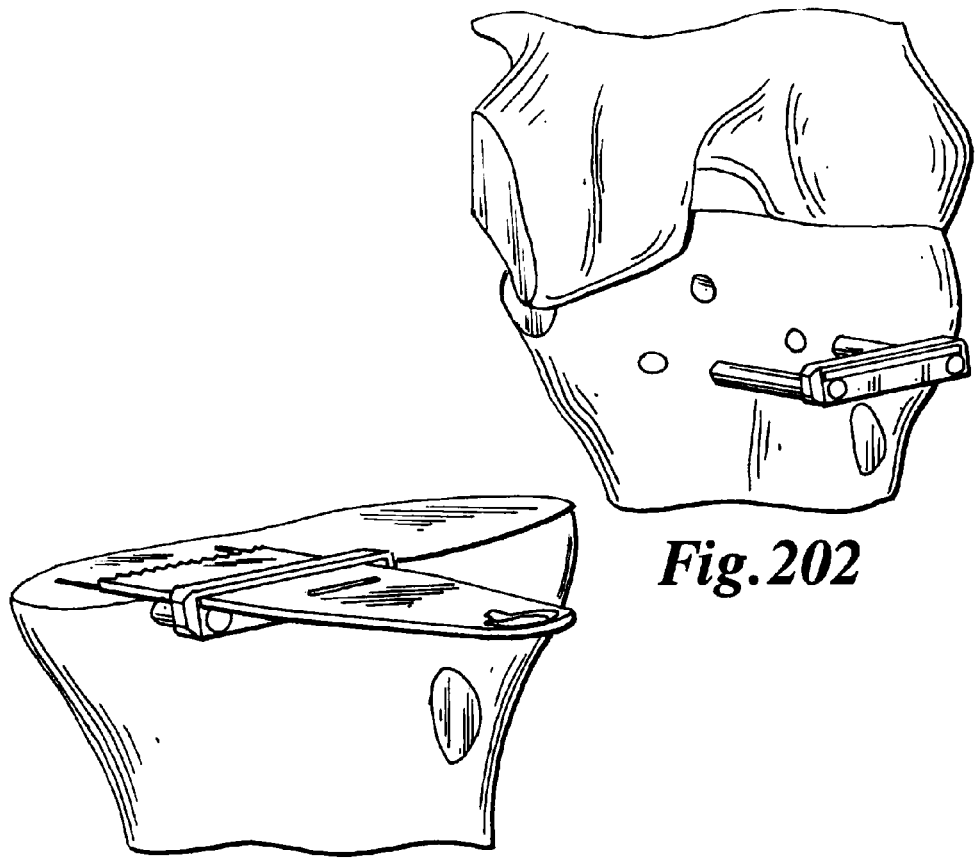
*Fig.202*
*Fig.205*
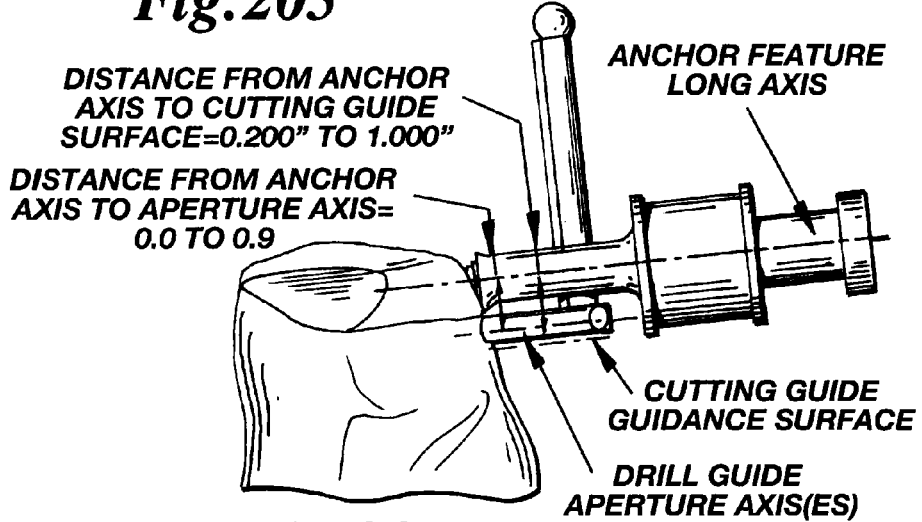
*Fig.207*

RESECTED SURFACE WITH RESPECT TO WHICH THE IMPLANT WILL BE ATTACHED

BONE TO BE REMOVED PRIOR TO PROSTHESIS IMPLANTATION

TYPICAL PLACEMENT FOR PINPLASTY GUIDANCE IN UNDERCUTTING MODE

TYPICAL PLACEMENT FOR PINPLASTY GUIDANCE IN OVERCUTTING MODE

TYPICAL PLACEMENT FOR ATTACHMENT OF CONVENTIONAL CUTTING GUIDE TO IMPLANTED PINS OR APERTURES IN BONE

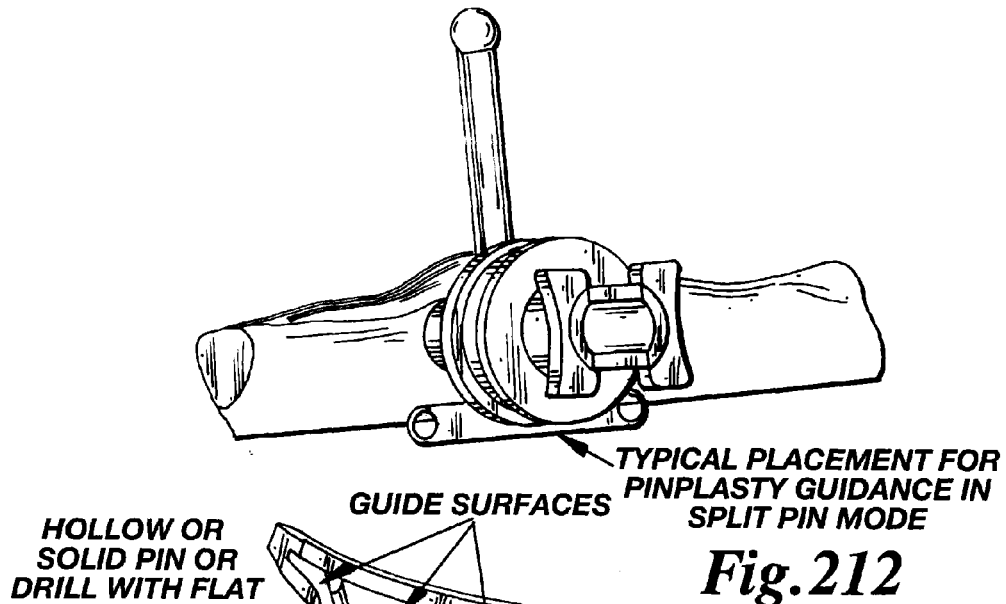
*Fig.212* TYPICAL PLACEMENT FOR PINPLASTY GUIDANCE IN SPLIT PIN MODE
GUIDE SURFACES
HOLLOW OR SOLID PIN OR DRILL WITH FLAT
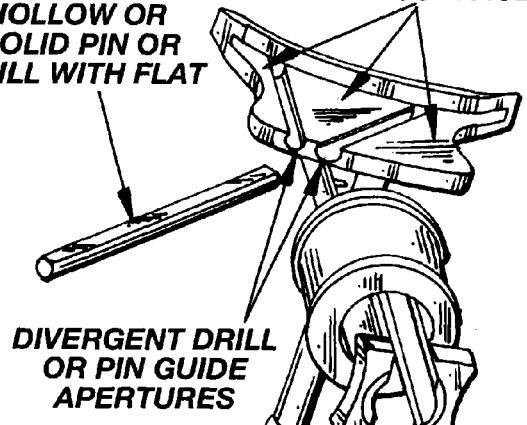
DIVERGENT DRILL OR PIN GUIDE APERTURES
*Fig.213*
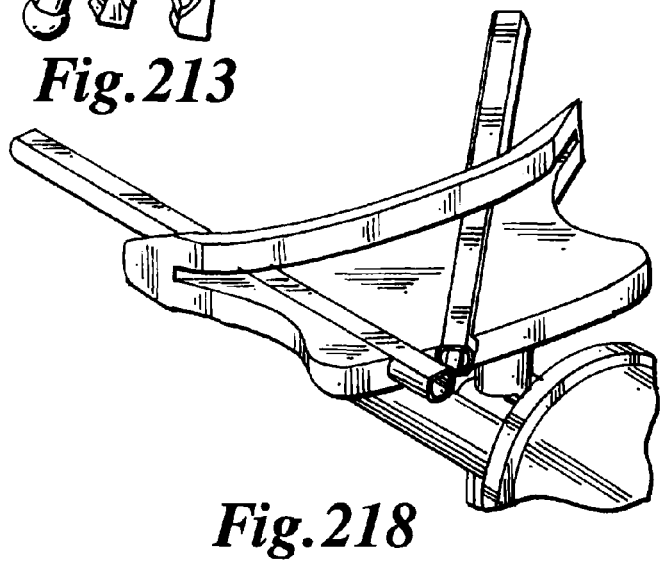
*Fig.218*

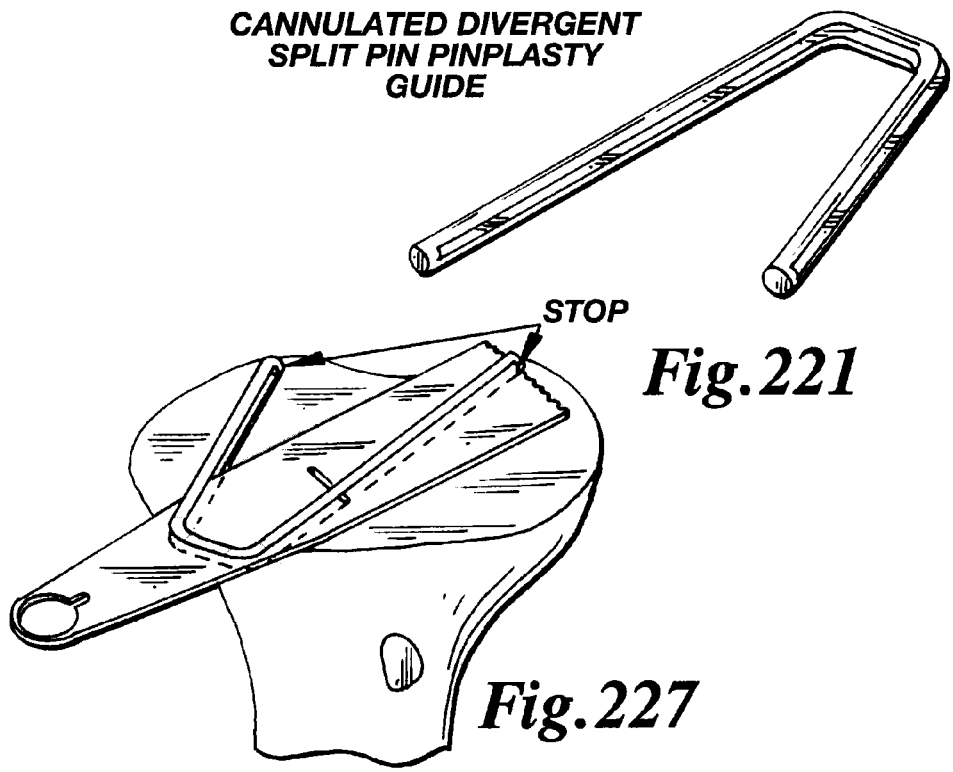
Fig.221
Fig.227
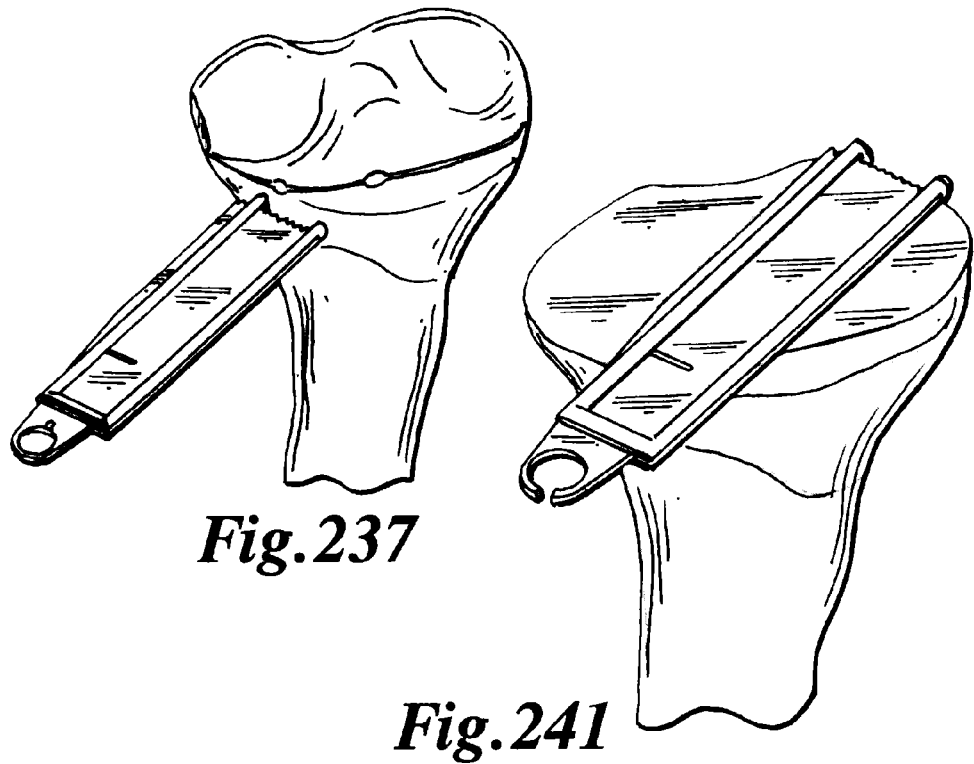
Fig.237
Fig.241

METHODS AND APPARATUS FOR PINPLASTY BONE RESECTION

RELATED APPLICATIONS

The present invention claims priority to U.S. Provisional Application No. 60/536,320, filed Jan. 14, 2004; U.S. Provisional Application No. 60/540,992, filed Feb. 2, 2004; U.S. Provisional Application No. 60/551,080, filed Mar. 8, 2004; U.S. Provisional Application No. 60/551,078, filed Mar. 8, 2004; U.S. Provisional Application No. 60/551,096, filed Mar. 8, 2004; U.S. Provisional Application No. 60/551,631, filed Mar. 8, 2004; U.S. Provisional Application No. 60/551,307, filed Mar. 8, 2004; U.S. Provisional Application No. 60/551,262, filed Mar. 8, 2004; and U.S. Provisional Application No. 60/551,160, filed Mar. 8, 2004, the disclosures of which are hereby fully incorporated by reference.

BACKGROUND OF THE INVENTION

1. Field of the Invention

This invention generally relates to methods and apparatus for bone resection to allow for the interconnection or attachment of various prosthetic devices. More particularly, the present invention relates to the use of a pinplasty bone resection technique in which pins placed internally within the bone are used as guide surfaces for a cutting tool.

2. Background Art

Different methods and apparatus have been developed in the past to enable a surgeon to remove bony material to create specifically shaped surfaces in or on a bone for various reasons including to allow for attachment of various devices or objects to the bone. Keeping in mind that the ultimate goal of any surgical procedure is to restore the body to normal function, it is critical that the quality and orientation of the cut, as well as the quality of fixation, and the location and orientation of objects or devices attached to the bone, is sufficient to ensure proper healing of the body, as well as appropriate mechanical function of the musculoskeletal structure.

In total knee replacements, for example, a series of planar and/or curvilinear surfaces, or "resections," are created to allow for the attachment of prosthetic or other devices to the femur, tibia and/or patella. In the case of the femur, it is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint. Additionally, with any surgical procedure, time is critical, and methods and apparatus that can save operating room time, are valuable. Past efforts have not been successful in consistently and/or properly locating and orienting distal femoral resections in a quick and efficient manner.

The use of oscillating saw blade based resection systems has been the standard in total knee replacement and other forms of bone resection for over 30 years. Unfortunately, present approaches to using such planar saw blade instrumentation systems all possess certain limitations and liabilities.

Perhaps the most critical factor in the clinical success of any arthroplasty procedure is the accuracy of the implant's placement. This can be described by the degrees of freedom associated with each implant. In the case of a total knee arthroplasty (TKA), for example, for the femoral component these include location and orientation that may be described as Varus-Valgus Alignment, Rotational Alignment, Flexion-Extension Alignment, A-P location, Distal Resection Depth Location, and Mediolateral Location. Conventional instrumentation very often relies on the placement of ⅛ or 3/16 inch diameter pin or drill placement in the anterior or distal faces of the femur for placement of cutting guides. In the case of posterior referencing systems for TKA, the distal resection cutting guide is positioned by drilling two long drill bits into the anterior cortex along the longitudinal axis of the bone. As these long drills contact the oblique surface of the femur they very often deflect, following the path of least resistance into the bone. As the alignment guides are disconnected from these cutting guides, the drill pins will "spring" to whatever position was dictated by their deflected course thus changing their designated, desired alignment to something less predictable and/or desirable. This kind of error is further compounded by the "tolerance stacking," inherent in the use of multiple alignment guides and cutting guides.

Another error inherent in these systems further adding to mal-alignment is deflection of the oscillating saw blade during the cutting process. The use of an oscillating saw blade is very skill intensive as the blade will also follow the path of least resistance through the bone and deflect in a manner creating variations in the cut surfaces which further contribute to prosthesis mal-alignment as well as poor fit between the prosthesis and the resection surfaces.

Despite the fact that the oscillating saw has been used in TKA and other bone resection procedures for more than 30 years, there are still reports of incidences where poor cuts result in significant gaps in the fit between the implant and the bone. Improvements in the alignment and operation of planar saw blades for resecting bone surfaces are desired in order to increase the consistency and repeatability of bone resection procedures.

SUMMARY OF THE INVENTION

The present invention provides guide surfaces for bone resection by utilizing a pinplasty technique in which a cutting tool having a linear cutting profile, such as a planar oscillating or sagital saw blade, is guided by the tangential surfaces of a plurality of pin members located internally within the bone.

One of the critical problems with existing cutting guide systems for planar saw blades is that the distal or cutting end of the saw blade is not supported by the guide as the saw blade cuts through bone. Because the distal end includes the cutting profile of the planar saw blade, it is simply not possible with conventional guide systems that are located exterior to the bone being cut to positively guide the distal end of the planar saw blade. The present invention overcomes this inherent limitation in the operation of a planar saw blade by locating multiple guide surfaces in the bone, not just next to the bone.

In one embodiment for a cutting tool having a generally linear cutting profile, the present invention utilizes a plurality of pin members located within at a series of independent pin apertures where a tangential surface of the pin cooperates with a flat surface of a planar saw blade to act as a cutting guide internal to the bone. Two or more of these tangential surfaces form corresponding lines of contact on the intended plane of a resected surface to be created by the linear cutting profile of a planar saw blade. The location and orientation of the pin members serve to define the intended plane of the resected surface. It will be seen that the location and orientation of the pin members, together with the orientation and operation of the planar saw blade, permit the tangential surface of the pin members to effectively guide not only the proximal end of the planar saw blade, but also distal portions of the planar saw blade. Depending upon the operation and orientation of the planar saw blade, at least two points or portions of the lines of contact with the flat surface of the planar saw blade are preferably maintained during operation of the planar saw blade. By maintaining at least two points or portions of contact, the pinplasty technique of the present invention overcomes the tendency of the planar saw blade to deflect or curve while cutting bone when guided only from the proximal end.

It is an often repeated rule of thumb for orthopedic surgeons that a "Well placed, but poorly designed implant will perform well clinically, while a poorly placed, well designed implant will perform poorly clinically." The present invention provides a method and apparatus for reducing implant placement errors in order to create more reproducible, consistently excellent clinical results in a manner that decreases the dependency of planar saw cuts on the level of manual skill of the surgeon creating a resected surface.

It should be clear that applications of the present invention are not limited to Total Knee Arthroplasty, but are rather universally applicable to any form of surgical intervention where the resection of bone is required. These possible applications include, but are not limited to Unicondylar Knee Replacement, Hip Arthroplasty, Ankle Arthroplasty, Spinal Fusion, Osteotomy Procedures (such as High Tibial Osteotomy), ACL or PCL reconstruction, and many others. In essence, any application where an inexpensive, accurate, and relatively precise system is required or desired for a bone resection is a potential application for this technology. In addition, many of the embodiments shown have unique applicability to minimally invasive surgical (MIS) procedures and/or for use in conjunction with Surgical Navigation, Image Guided Surgery, or Computer Aided Surgery systems.

BRIEF DESCRIPTION OF THE DRAWINGS

The patent or application file contains at least one drawing executed in color. Copies of this patent with color drawing(s) will be provided by the Patent and Trademark Office upon request and payment of the necessary fee.

Other important objects and features of the invention will be apparent from the following detailed description of the invention taken in connection with the accompanying drawings in which:

FIGS. 3-186, 190-197, 202, 205, 207-213, 218, 221, 227, 237, 241-242, 246, 250, 252, and 254 show various depictions of the placement of pin members and operation of a cutting tool in accordance with alternate embodiments of the present invention.

DETAILED DESCRIPTION OF THE PREFERRED EMBODIMENTS

Figure 1:
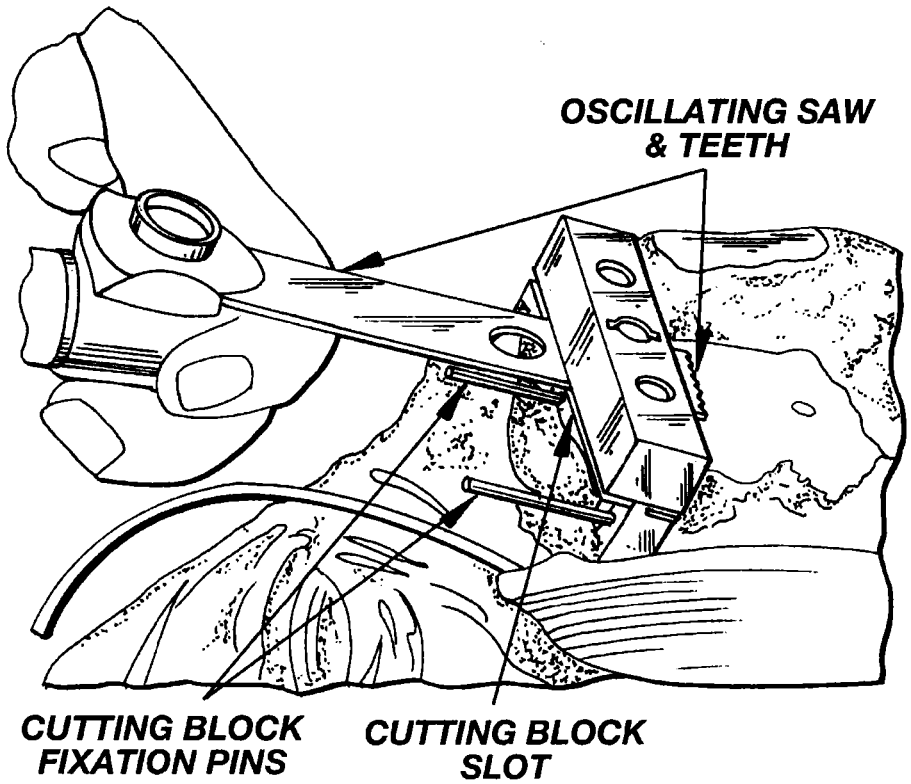
FIGS. 1 and 2 are pictorial representations of planar saw cutting guide systems of the prior art.
Figure 2:
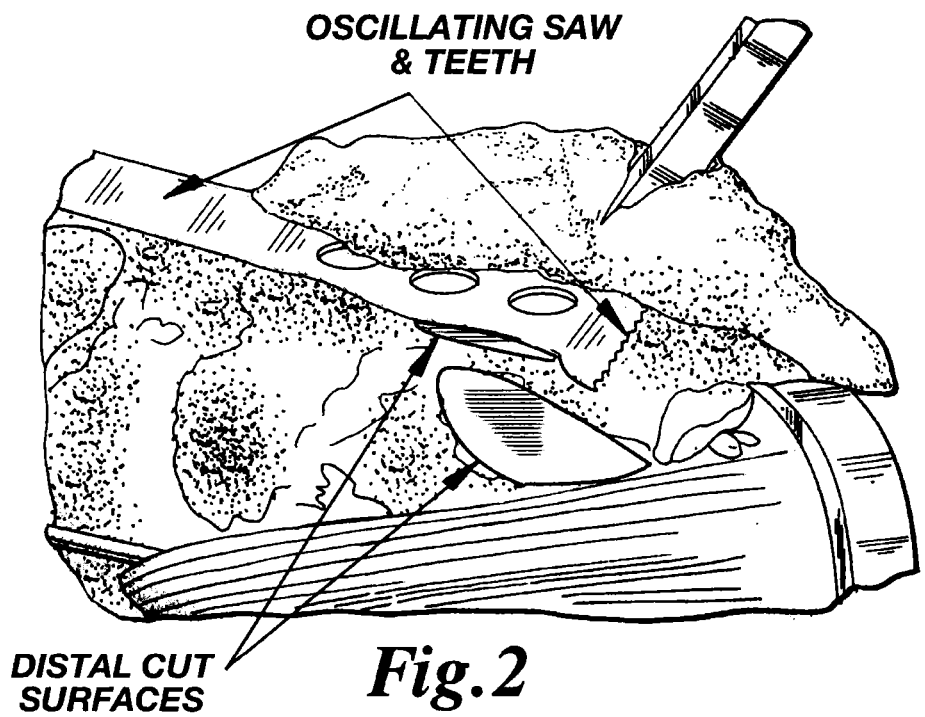

FIGS. 1 and 2 show a conventional oscillating saw blade system in action. The basic components are the oscillating saw, the cutting guide, and fixation features of the cutting guide, which in this case are 0.125 inch drill pins. The cutting guide possesses at least one slot to which the saw is engaged during cutting. A drawback about this technology is shown in FIG. 2 as the saw blade is in an extended cantilever as it finishes the side of the cut furthest from the guide generating sometimes significant error requiring recutting or tweaking of the cut by eye as shown in FIG. 2.

Figure 3:
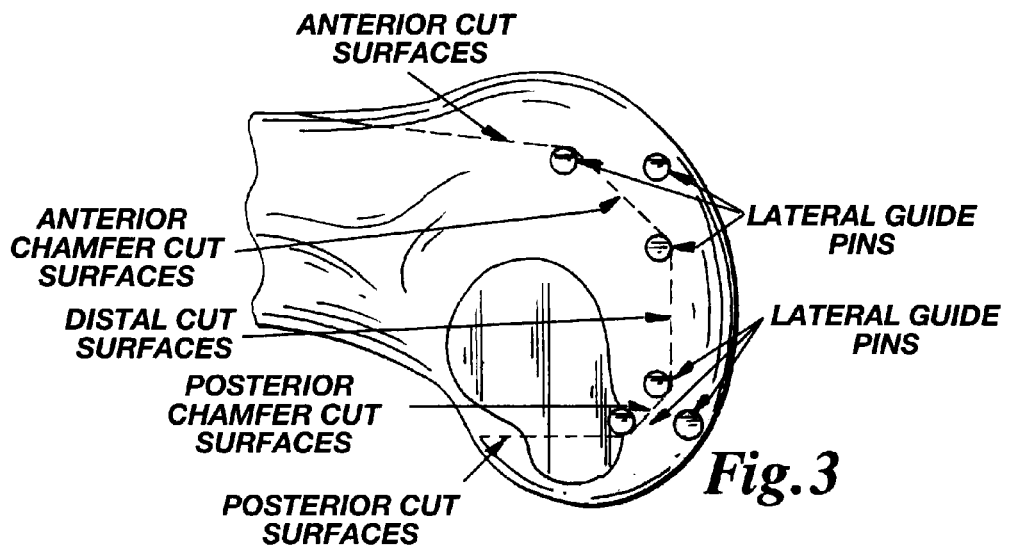
Figure 4:
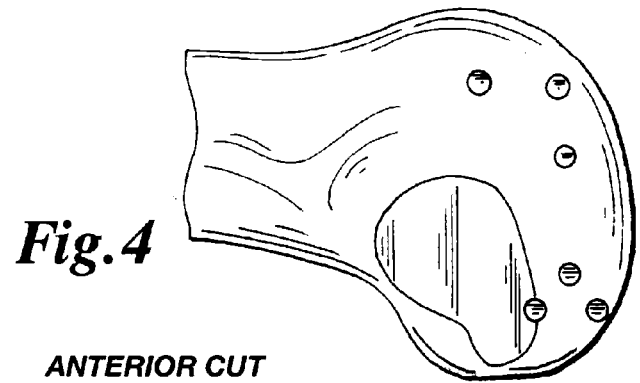
Figure 5:
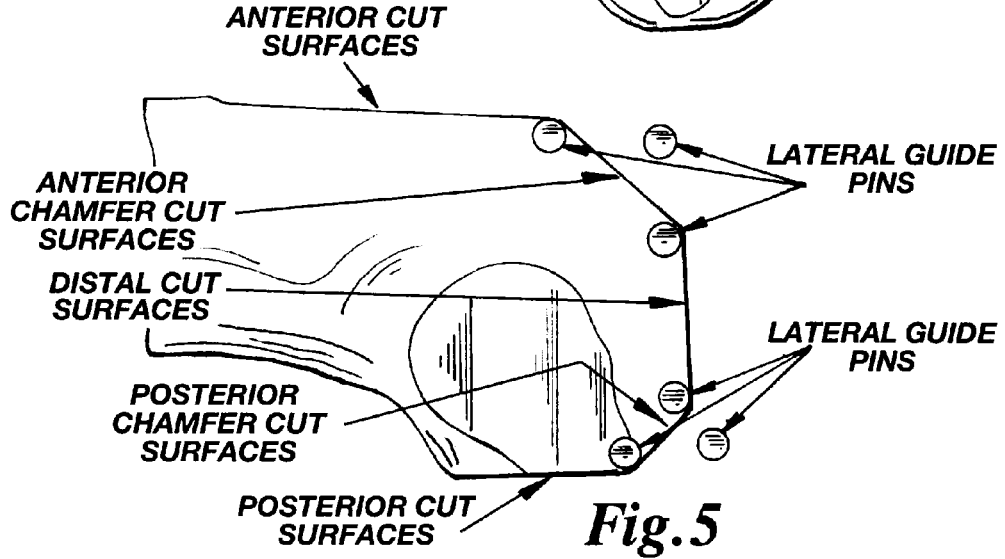
Figure 6:
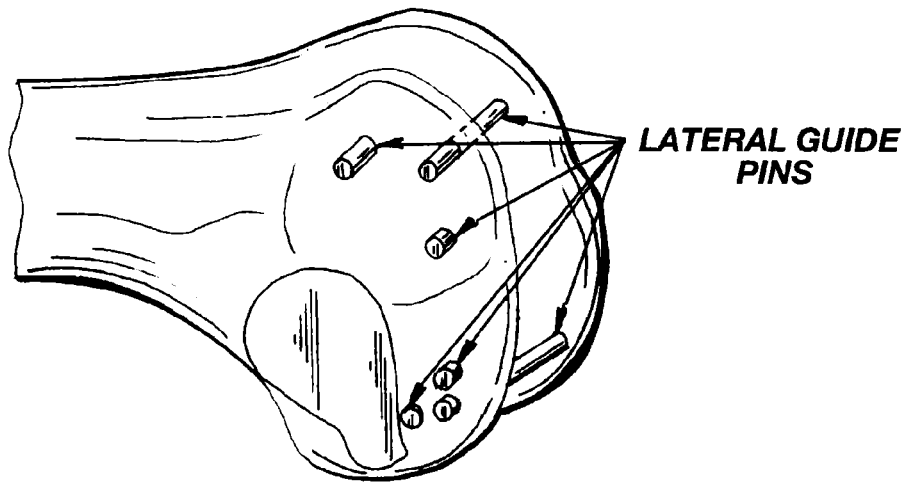
Figure 7:
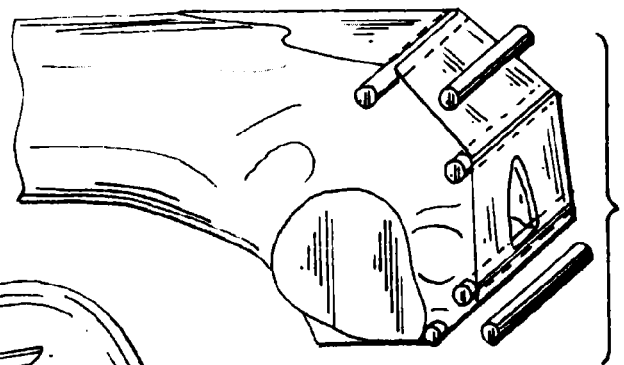
Figure 8:
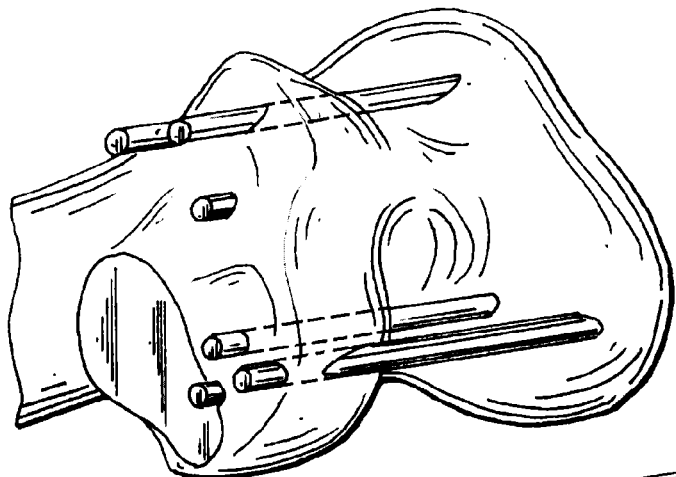
Figure 9:
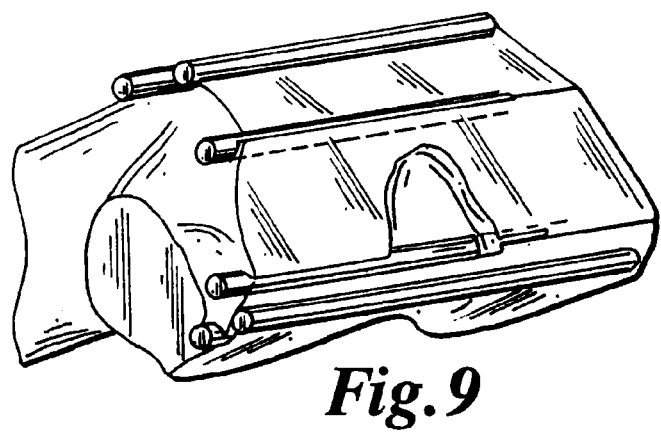
Figure 10:
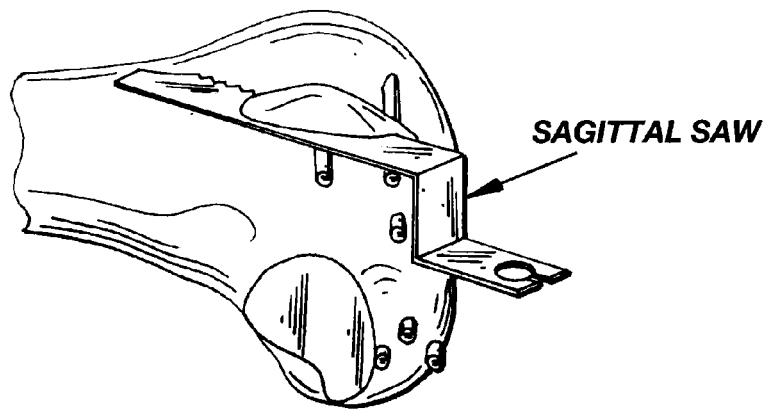
Figure 11:
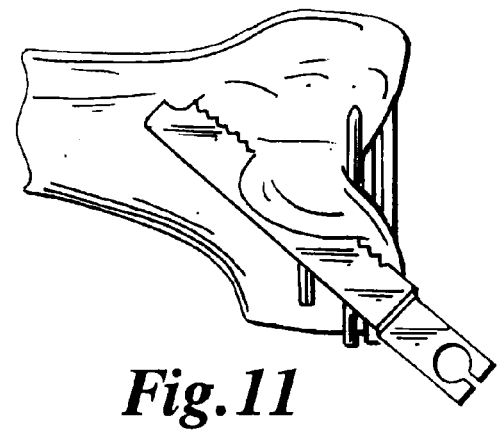
Figure 12:
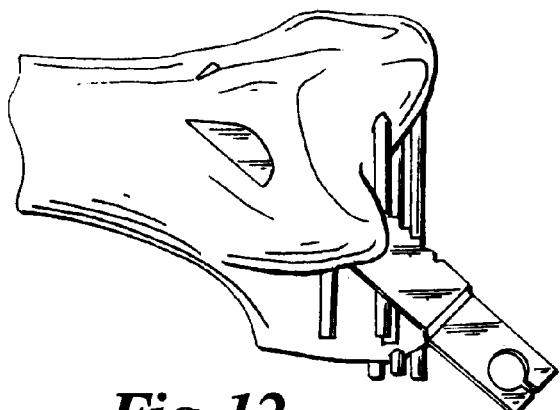
Figure 13:
Figure 14:
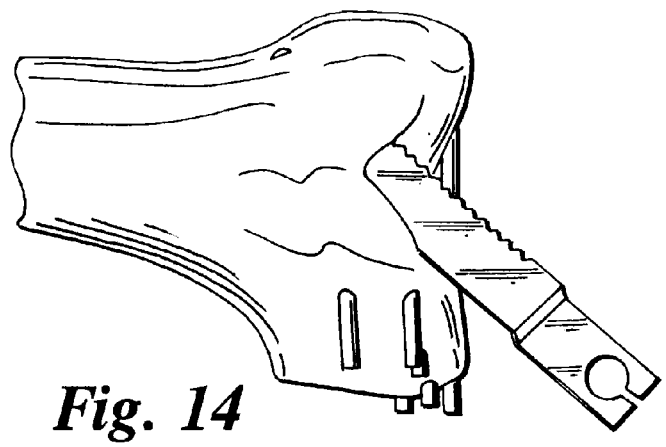
Figure 15:
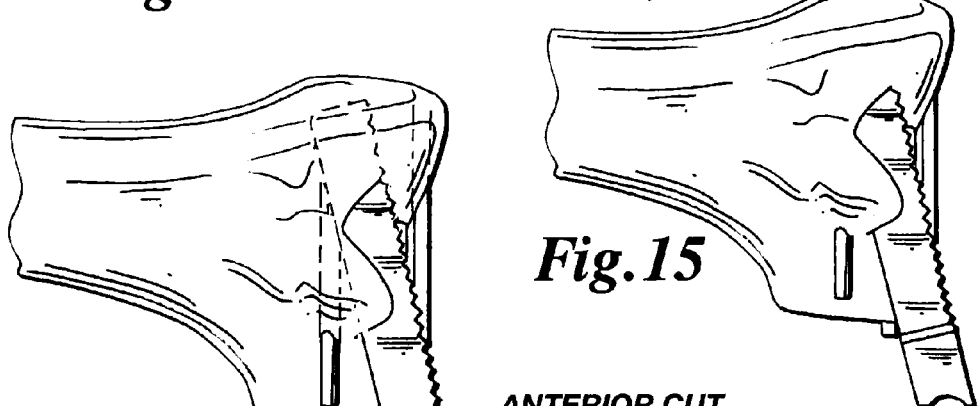
Figure 16:
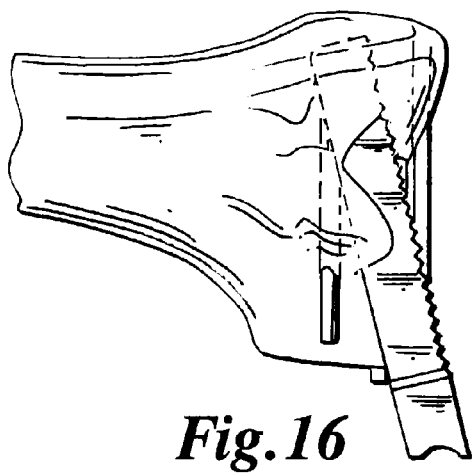
Figure 17:
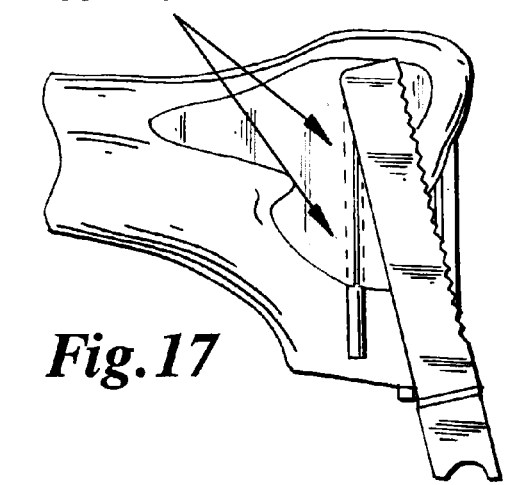

FIGS. 3-49 show various depictions of the placement of pin members in accordance with one embodiment of the present invention. FIG. 3 is a view from medial to lateral showing the intended location of the cuts and some of the possible pin locations. In this particular form of this concept, the 'guide' is merely a series of independent pins positioned through, at, above, or below the cut surfaces to be created. For conventional TKA, the basic surfaces to be created are the Anterior Cut, Anterior Chamfer Cut, Distal Cut, Posterior Chamfer Cut, and Posterior Cut as is made clear in FIGS. 3, 5, 17, 32, and 41. FIG. 42 shows the Chamfer Cuts being made by different cutting tools. In later figures, application of this concept to the tibia will be explored. Although the embodiment of the pins shown is, well, pins, one versed in the art will recognize that the pin members could be drill bits, roughened shafts (for purchase/fixation to the bone), threaded pins (where the threads may be used to facilitate fixation of the pins to bone or to ancillary guide surfaces), or other cylindrical or non cylindrical cross-sectioned components having a generally longitudinal axis and at least one surface designed to serve as a tangential surface for purposes of defining the points and/or portions of the lines of contact that will defined a plane of a resected surface.

Preferably, pin guide members are made of materials that are more durable than bone material and also at least as durable, if not more durable, than the materials of the planar saw blade of the cutting tool. Materials could be harder or softer than the material comprising the cutting tool, and in some cases the cutting tool and the pins could be the same material—this is especially viable for ceramics which have very nice bearing characteristics. Certain surface treatments for metal may also be advantageous (titanium nitride, ceramic or non-metallic coating). Preferably, the cutting tool is prevented from cutting or abrading the cutting guide to avoid debris generation. Although pulsating lavage will normally clean any debris from the cut surfaces, the possibility of a foreign body, allergic, or other adverse reaction should be avoided. In certain situations, however, it may be desirable to construct the pin member guides of allograft or autograft bone tissue, such as when used in cortical bone tissue where it may be acceptable to cut the pin member guides. Diamond, or other carbon-based materials, could also be utilized, cost permitting. Also, the pin guides could be constructed of plastics, liquid metal, or some other form of injection moldable material thereby reducing cost levels to an extent enabling the pins to be offered on a disposable or semi-disposable basis.

It should be understood that the pinplasty technique of the present invention can be combined with any other forms of alignment and cutting guide tools and techniques. An example of such a combination is to modify a standard cutting guide, as shown in FIG. 1, to include holes that are tangent to the cutting guide slot and to which the pins of this invention are attached. This could be especially useful in the case of "4 in 1" cutting blocks wherein the blocks could be positioned against the cut distal surface and the pins passed through the block and into the bone and across, along, or about the cut surface to be created. "5 in 1" cutting blocks or other blocks could be augmented by this technology in a similar manner.

Alignment guides are not shown specifically in the drawings of this application. Many different kinds of devices or alignment systems could be used to position the pins or cutting guides of this invention or to create bone aperture features or holes to which these guides are attached. Outstanding examples include alignment or drill guides disclosed in U.S. Pat. Nos. 5,514,139, 5,597,379, 5,643,272, 5,810,827, and U.S. Publ. No. US 2002-0029038 A1. It will be seen that the location and orientation of the pin members or pin cutting guides of the present invention are critical in obtaining desirable results. Accordingly, an alignment system used to directly or indirectly dictate the position of these guides/pins must be both precise and accurate in positioning the guides/pins or in creating the bores within the bone tissue to which they are engaged. Modification of prior art devices to accomplish this are fairly straight-forward. For instance, the ligament balancing alignment guide of U.S. Pat. No. 5,597,379 could be modified to include a plurality of drill guide portals (58) and a plurality of apertures (44), corresponding to the 8 drill holes shown in FIG. 108 of this patent. Additional drill guide portals could be included and marked on the guide of U.S. Pat. No. 5,597,379 to accommodate different sized femurs and thereby different sizes of prostheses and/or cutting guides. The immediately aforementioned was but one example of alignment systems that could be utilized to facilitate use of this new invention.

In one embodiment for use in TKA procedures, the pin guide members shown in many of the figures herein range in diameter between 0.125 inches and 0.158 inches. Pin guide members could be larger or smaller depending upon the requirements of the bone resection procedure. The preferred diameters of the pin guide members for TKA procedures represent a significant decrease in the overall material volume of any cutting guides for TKA procedures. The material volume of a cutting guide can have a direct effect on the cost of producing the device, and, in general, the less the material volume, the lower the cost. Thus, the guides disclosed may have a total material volume of somewhere between 0.0092 cubic inches and 0.118 cubic inches. In comparison, the conventional guide shown in FIG. 1 probably has a volume somewhere in the area of 5.0 cubic inches or more, which is 40 to 500 times more massive than some of the guides or pins of the present invention.

FIGS. 3 through 49

FIGS. 3 through 49 concentrate on mediolaterally, or 'side to side' oriented pins. Although any kind of cutting tool or milling handle could be engaged to these pins, a sagittal saw (FIGS. 10-14) and an oscillating saw (FIGS. 21 through 32) are shown. A wire or gigli saw could also be used in conjunction with the pins or guides disclosed herein as the cutting profile of such a saw affects the same linear cutting profile as a planar saw blade. Similarly, any of the following cutting tools effecting a linear cutting profile could also be used: rotating or oscillating or reciprocating cutters, linear milling tools, garrotes (thin, highly tensioned wire cutter), powered rasps or broaches, manual rasps or broaches, jack hammers, chisels, chain saws, osteotomes, abrasive wire cutters, oscillating/reciprocating/chain/gigli/coping/scroll/band/circular/hack/jig/sagittal saws, belt cutters, or cutting tools that combine elements of the aforementioned cutting tools.

In one embodiment, cutting tools may be plunged across, along, or through the pin guides of the present invention in any direction desirable. The directions of tool movement with respect to the pins include those generally oblique, normal, or parallel to the long axis of any pin, guide, or guide surface of this invention. Furthermore, the cutting tools may move linearly with respect to the bone and/or guide, or may be manipulated to move in circular, nonlinear, or 'sweeping motions' (shown in FIGS. 13 through 15).

Figure 18:
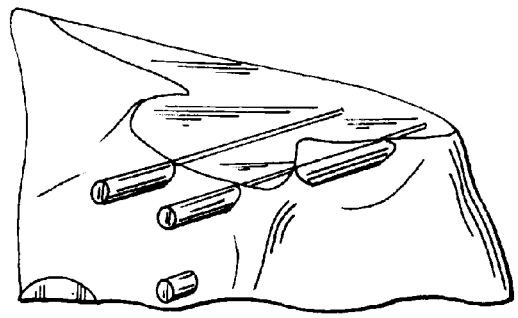
Figure 19:
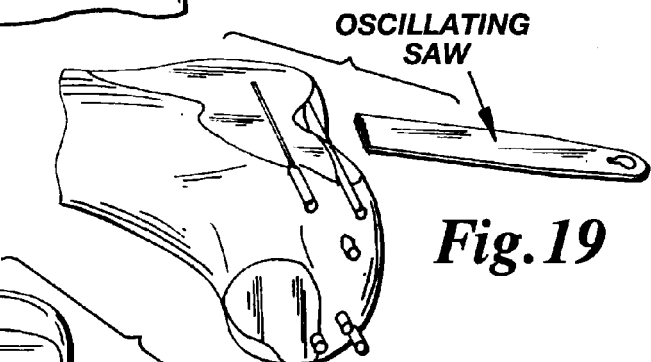
Figure 20:
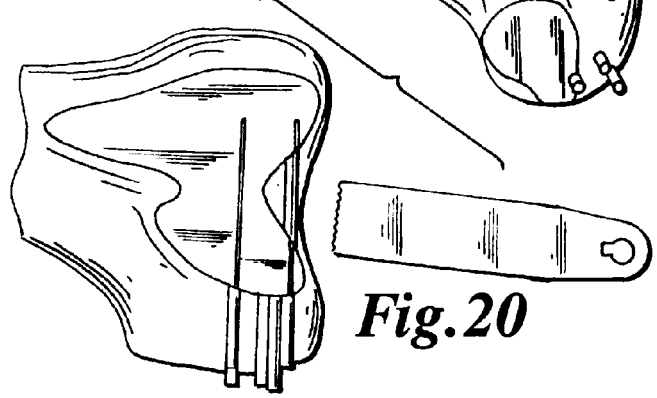
Figure 21:
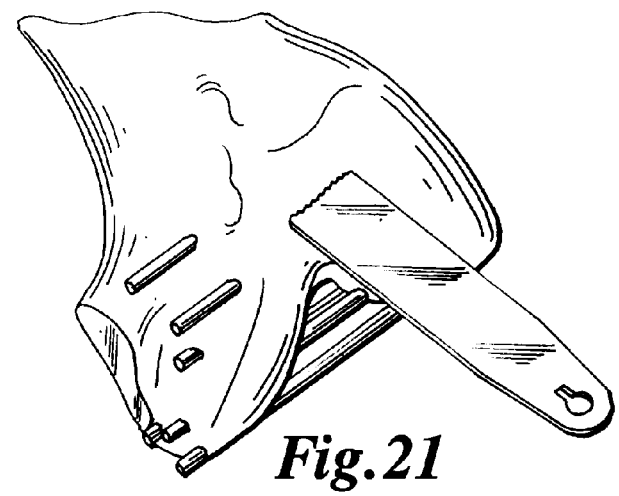
Figure 22:
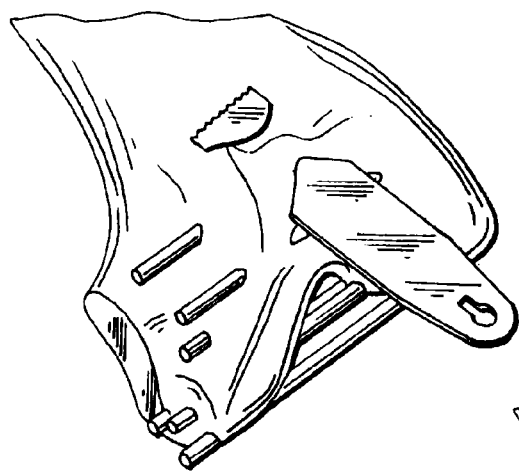
Figure 23:
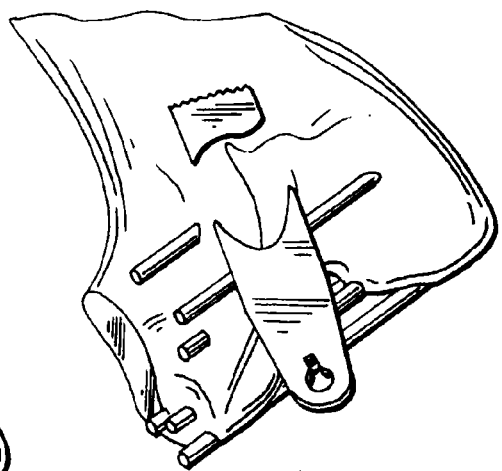
Figure 24:
Figure 25:
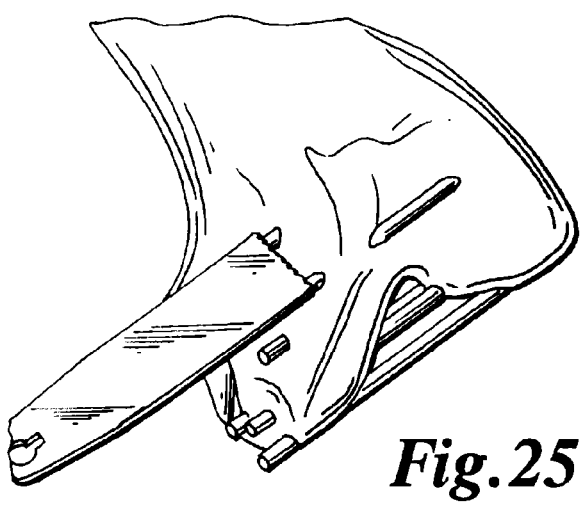
Figure 26:
Figure 27:
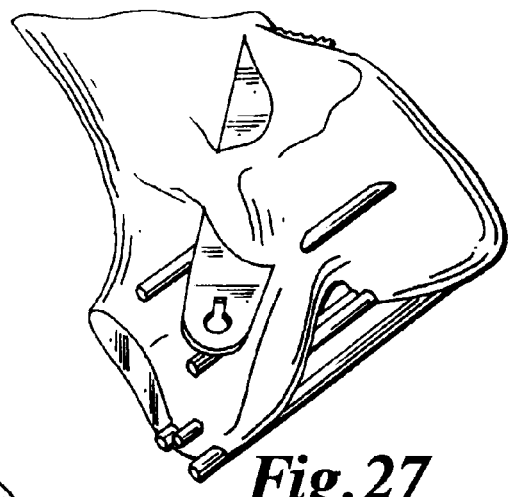
Figure 28:
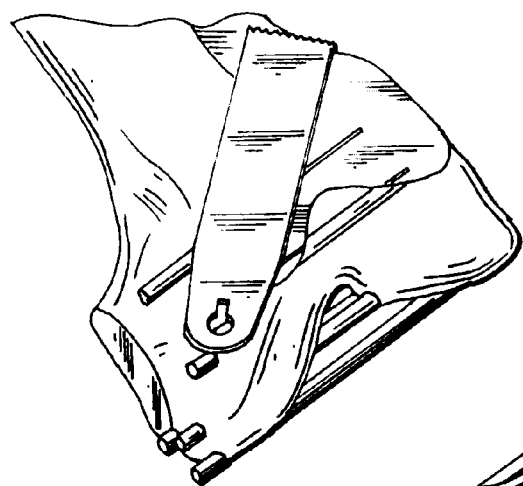
Figure 29:
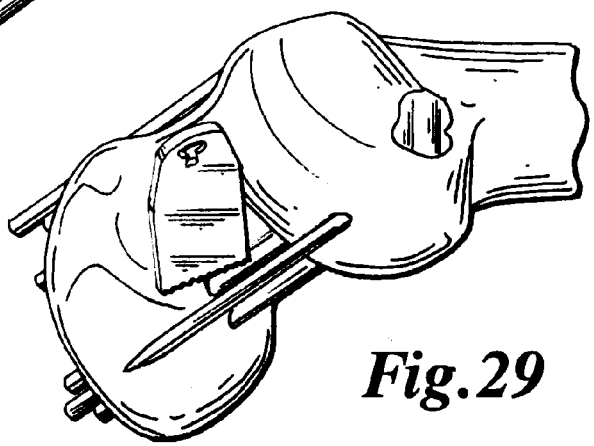
Figure 30:
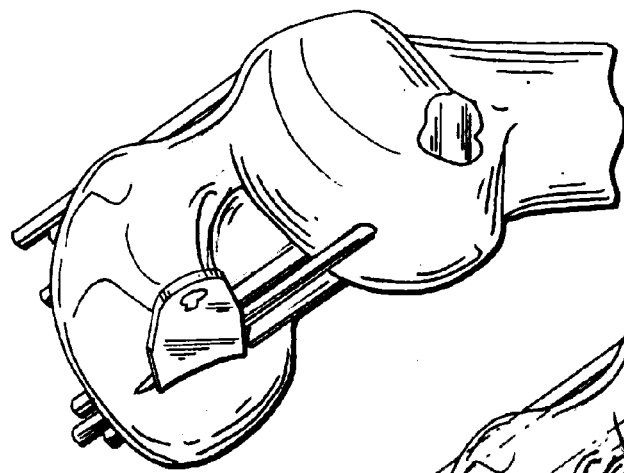
Figure 31:
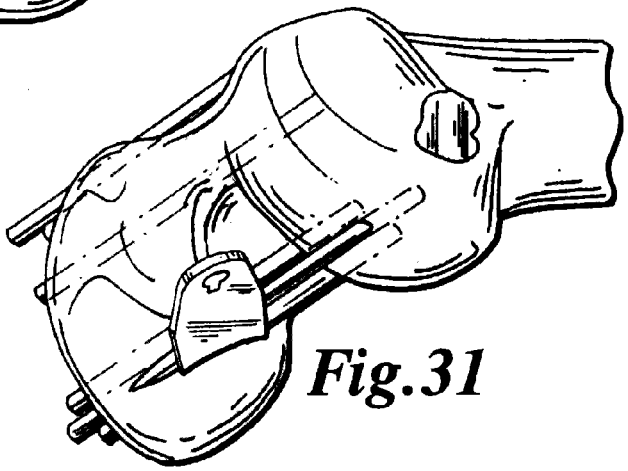
Figure 32:
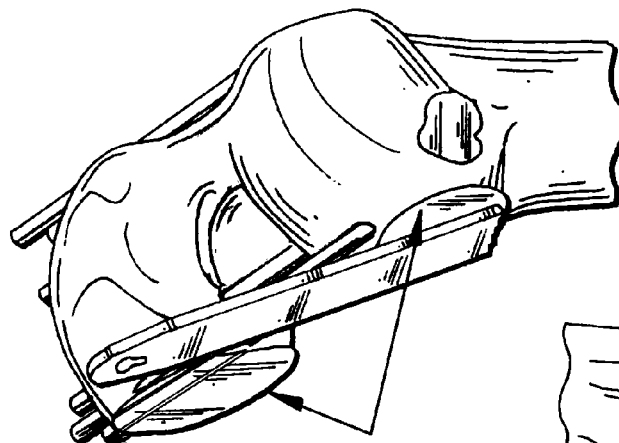

Furthermore, although the pins shown in FIG. 18 show the upper surface of the guide pins having been used to guide the cutting tool to create the cut surface, the pins could easily be located in a more anterior location allowing their 'underside' to act as the guide surface (see FIGS. 87 through 94 for an example of this principal of operation applied to the distal femoral cut). This concept could be referred to as 'undercutting.' This may be desirable if the 'artifacts' described with respect to FIGS. 43 and 44 are undesirable. The technique of cutting while engaged to the 'upper side' of the pins could be referred to as 'overcutting' (a term not to be confused with removing too much bone).

FIGS. 45 through 49 show an alternative or adjunct/modular guide for use with the pins. This modular guide could be integrally formed with the pins or seperably attached thereto. The modular guide surfaces could help the surgeon initially align the cutting tool with respect to the pins and/or the cut to be created and/or/also to maintain that relationship during a portion of or the entirety of the cutting process used to create the cut. Undercutting is also beneficial in this form of the present invention, as is the split pin, hollow pin, and hollow split pin embodiments of the present invention.

Referring again to FIGS. 43 and 44, the placement of pins used in the overcutting form of the present invention leaves behind it the holes shown in FIG. 44 which will be referred to as 'artifacts,' a normally undesirable thing. A major issue confronting surgeons and industry alike in the pursuit of minimally invasive arthroplasty, especially knees, is the control of Polymethylmethacrylate (otherwise known as PMMA or Bone Cement). It may be highly beneficial to first attach the implant to the bone, then inject bone cement through these artifacts or portals. The cement recesses formed in the fixation surfaces of the implant will readily accept the cement that 'oozes' up from these artifacts/pin holes and act to facilitate interdigitation of the bone cement with both the implant and the bone while controlling or helping to limit extravasation of the bone cement out from under the implant and into the joint space. This could be key in avoiding the presence of bone cement debris floating about the joint after surgery thus leading to premature failure of the bearing surfaces of the implants (otherwise known as $3^{rd}$ body wear, a potential problem in cemented minimally invasive arthroplasty). Any one, all, or any combination of the artifacts could be used in this manner.

It should be noted that, in many of the figures, the cut surface created by the cutting tool in accordance with the pinplasty technique of the present invention are shown as having already been completed for the sake of clarity. Similarly, the bones may be shown as being transparent or translucent for the sake of clarity. The guides/pins, cutting tool, bones, and other items disclosed may be similarly represented for the sake of clarity or brevity.

Figure 107:
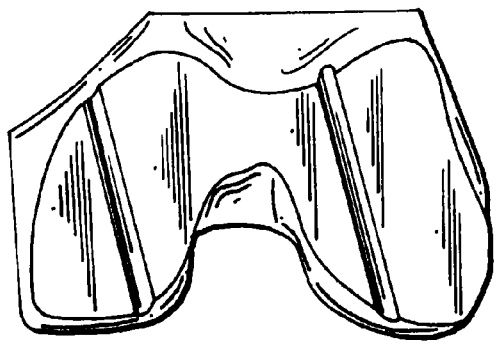

FIGS. 50 through 107

Figure 55:
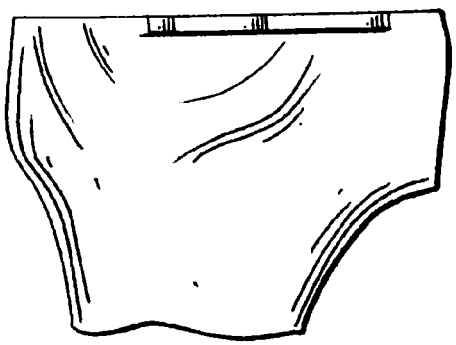
Figure 56:
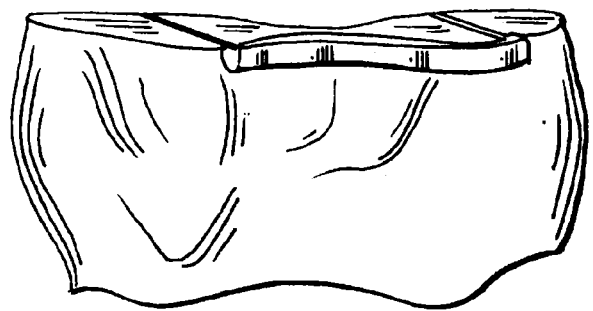
Figure 57:
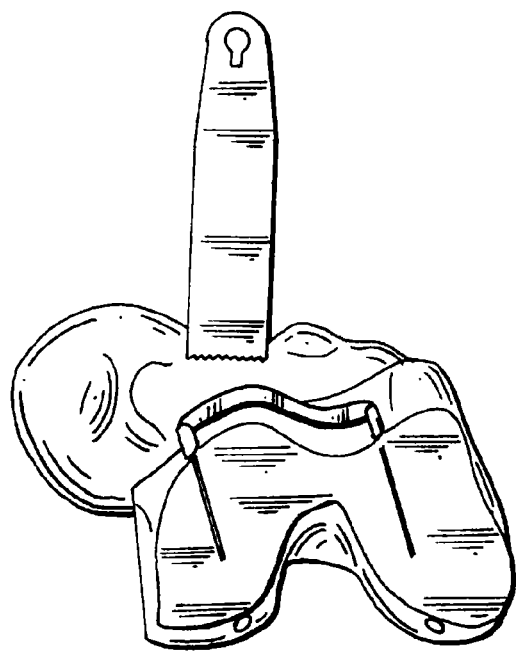
Figure 58:
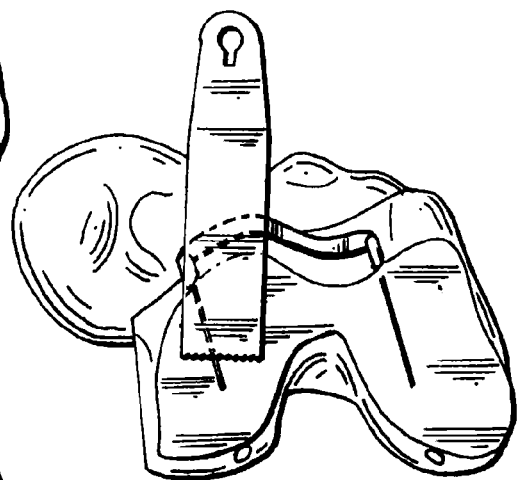
Figure 59:
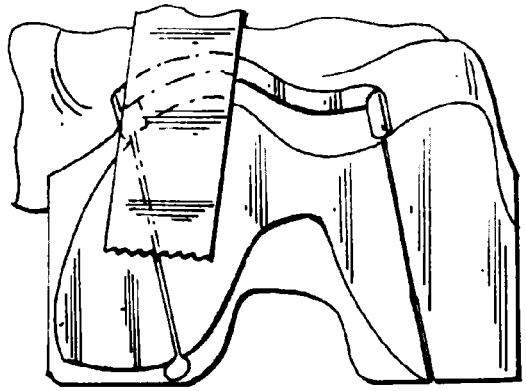
Figure 60:
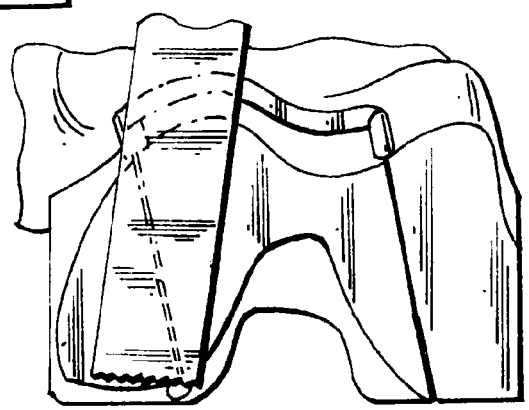
Figure 69:
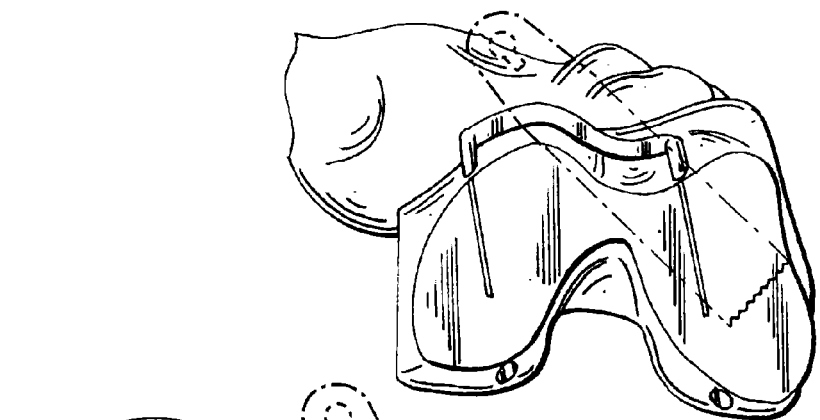
Figure 70:
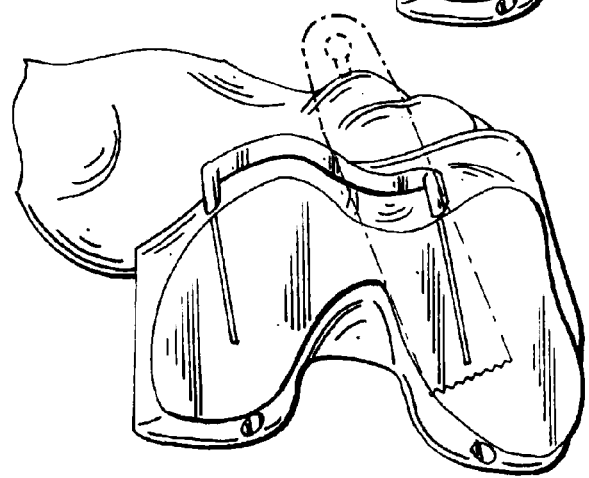

FIGS. 50 through 107 disclose a series of internal guides or pin members for use in conjunction with different cutting tools in different ways. FIGS. 50 through 56 show the pins/guide being inserted into preformed holes in the bone, while FIGS. 55 and 56 are intended to make clear that the pins and the guide surface that interconnects them are at least in some manner tangent and/or coplanar with the surface to be created in this form of the pinplasty technique of the present invention. FIGS. 57 to 71 show that a cutting tool (in the instance shown, an oscillating saw blade) could be located, oriented, and/or moved/manipulated along, across, and/or through the pins/guides of the present invention in any manner desired.

In the embodiment shown in FIG. 52, the drill holes are oriented at approximately a 15 degree angle relative to a vertical line running from the top to the bottom. It will be recognized that it is intended that the pins/guides used in accordance with the pinplasty technique of the present invention may be inserted at any angle with respect to the orientations shown. The alignment systems used to dictate the location and orientations of the pin guide members of the present invention may therefore need to be 'infinitely adjustable' or, perhaps more properly, 'infinitesimally adjustable' in all 6 degrees of freedom, or any combination of degrees of freedom to facilitate proper pin/guide placement. This may be especially important in computer assisted surgery where initial placement is often estimated, and additional fine tuning of the location and/or orientation of alignment system or cutting guide systems is required. Incremental adjustment, especially in well-designed manual alignment systems, may also work well. Specifically, the pins of the present invention could also be oriented at up to a 90 degree angle relative to the vertical line that represents the tangential line formed on the surface to be resected. In the embodiment shown in FIG. 52, the longitudinal axis of the pin guide members are located parallel to each other and approximately 1.50" apart from each other. Although greater distance between pins may facilitate greater accuracy in final cut/pin location and orientation, the pins could be located more closely together to allow for decreasing or alternative surgical exposure of the bone.

Figure 72:
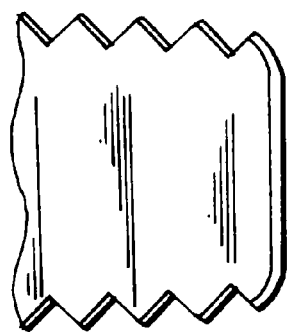
Figure 71:
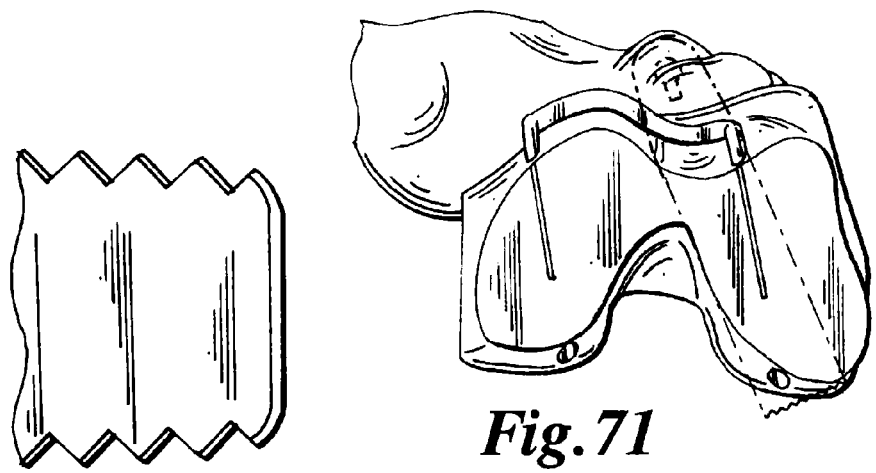
Figure 73:
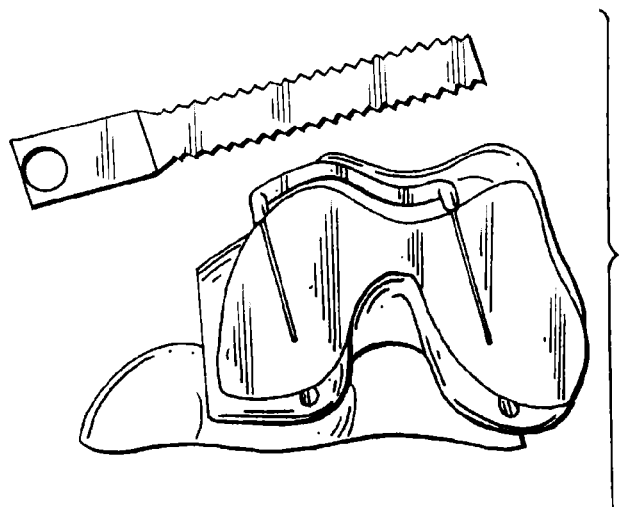
Figure 74:
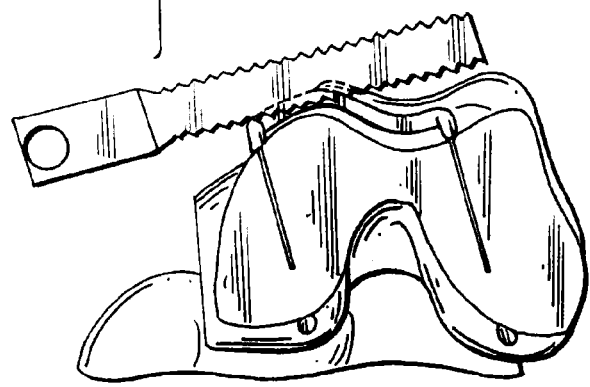
Figure 75:
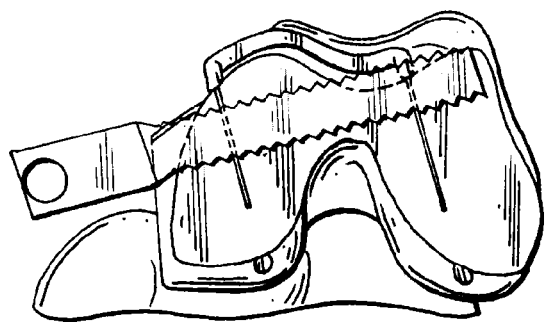
Figure 76:
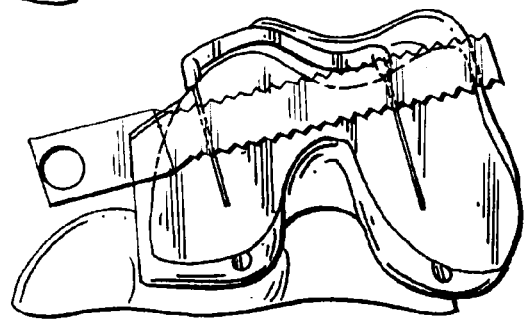
Figure 77:
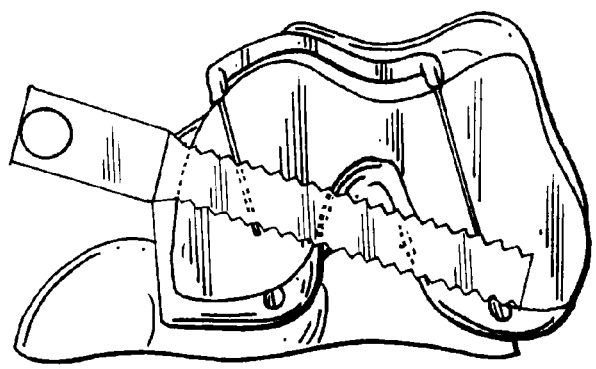
Figure 78:
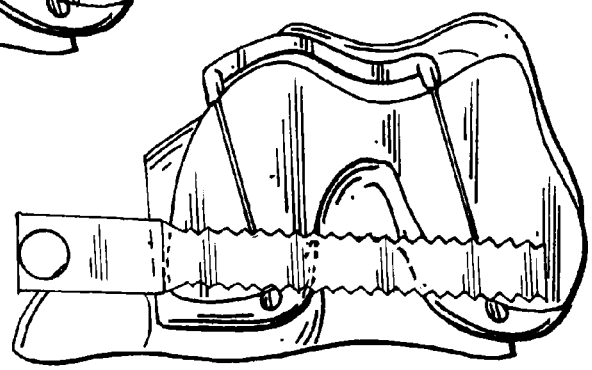

FIG. 72 shows the distal end of a sagittal saw with its distal most teeth smoothly rounded to minimize any damage induced by contact between the cutting tool and the soft tissues surrounding the joint. Given that a bruise is generally more desirable than a laceration (especially in terms of arteries or nervous tissue), this feature is particularly beneficial in connection with the present invention and in conjunction with other techniques or inventions. Alternatively, the smoothing of the distal most teeth or distal end of the sagittal saw could be created by slipping a cover over the distal end area, or formed as an integral part of it, to form a non-cutting distal most area configured to minimize harm to tissues whose integrity it is desirable to maintain. In one embodiment, the distal most end could be fitted with Teflon® tip that would serve as this distal-most bumper of the sagittal saw blade.

FIGS. 73 through 78 show a cutting tool (in this example a sagittal saw) traversing the pins/guide of the current invention in undercutting mode.

Figure 79:
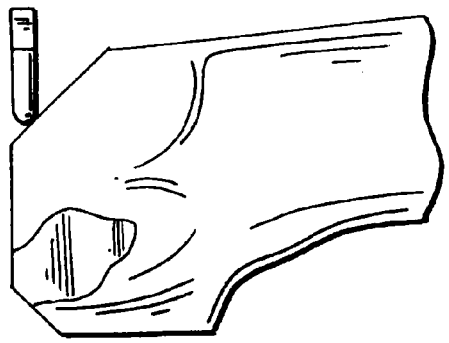
Figure 80:
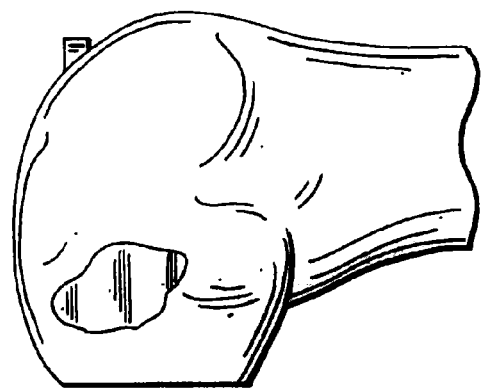
Figure 81:
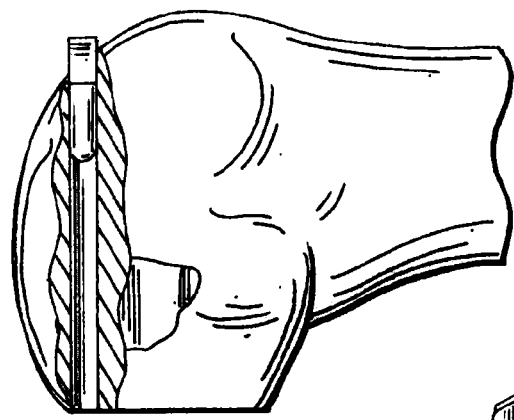
Figure 82:
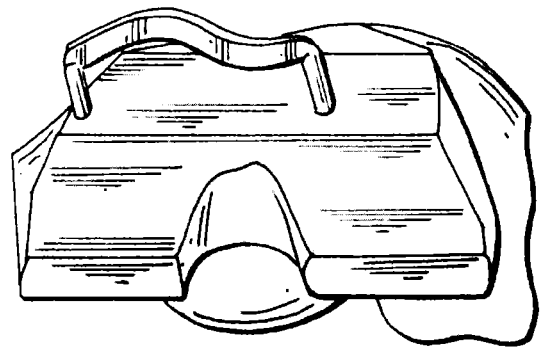
Figure 83:
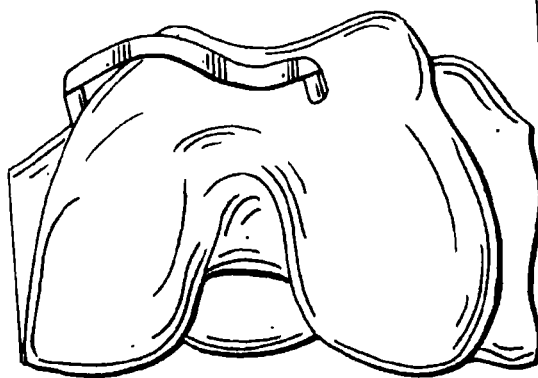
Figure 84:
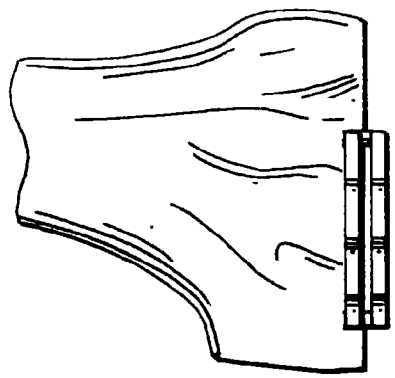

FIGS. 79 through 84 are intended to make clear that even in overcutting mode, the use of the pins/guides of the present invention need not leave artifacts if it is so desired. FIG. 79 shows an overcutting guide prior to its use with the distal cut it will participate in creating already made. FIG. 80 shows the guide with respect to the femur prior to any cuts. Similarly, no cuts have yet been made in FIG. 81 (except the holes), but the bone is shown as being transparent. FIG. 82 further clarifies this aspect of the present invention via a frontal view of the distal cut surface. FIG. 83 shows the distal femur prior to cutting. In this form of the present invention, the pins will be engaged to the cutting tool over a lesser length than the hereinbefore disclosed forms, but may still act to guide the cutting tool effectively without creating artifacts. Undercutting could also be implemented in conjunction with this form of the present invention. FIG. 84 shows a saw capture on the overcutting guide with the cut shown.

Figure 85:
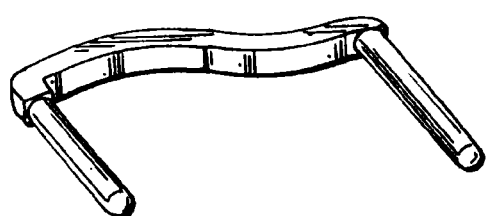
Figure 86:
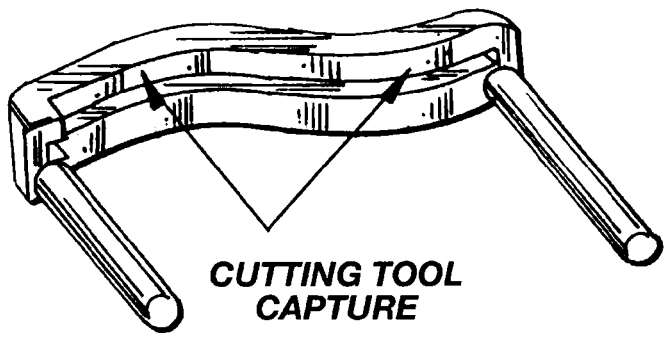

FIGS. 85 and 86 show the pins/guide without the bone. It should be noted that the cutting tool capture noted in FIG. 86 could be modular and/seperable from the pins, or it could form a one piece construct with them, or there could be a second capture opposite the first such that the guide could be applied to left or right knees or other joints/bones (this concept could be described as a 'bilateral design'). It should be noted that any of the forms of the present invention disclosed herein could be adapted to bilateral design to facilitate ease of use and/or economics by the surgeon, hospital, or staff, cleaning staff, and/or OEM's or contract manufacturers.

Figure 92:
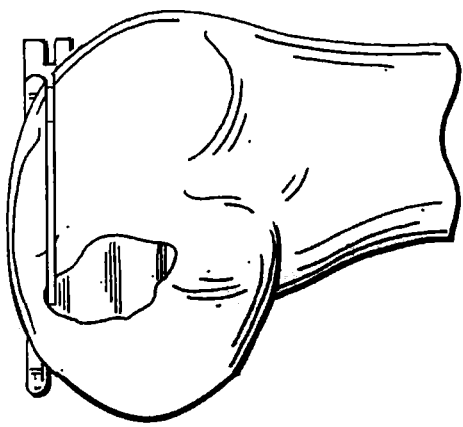

FIGS. 87 through 94 disclose one form of an undercutting guide. As noted earlier, the potential advantage of an undercutting guide is that it is attached to holes formed in bone tissue that is to be removed by completion of the cuts thus avoiding the creation of artifacts. Comparing FIGS. 88 and 89 also makes clear that the lower most portion of the cutting guide pins will still be fixed to bone overlying the posterior chamfer cut when the distal cut has been completed. Thus, the distal cut will be accurate even if the last bit of bone to be cut beyond the distal cut shown in FIGS. 92 and 93 becomes less accurate as the bone to which the guide is attached is consumed. In other words, FIG. 92 shows the distal cut completed and the remainder of the bone to be cut is simply to allow for the placement of subsequent alignment guides, cutting guides, sensors, or other instrumentation.

Figure 87:
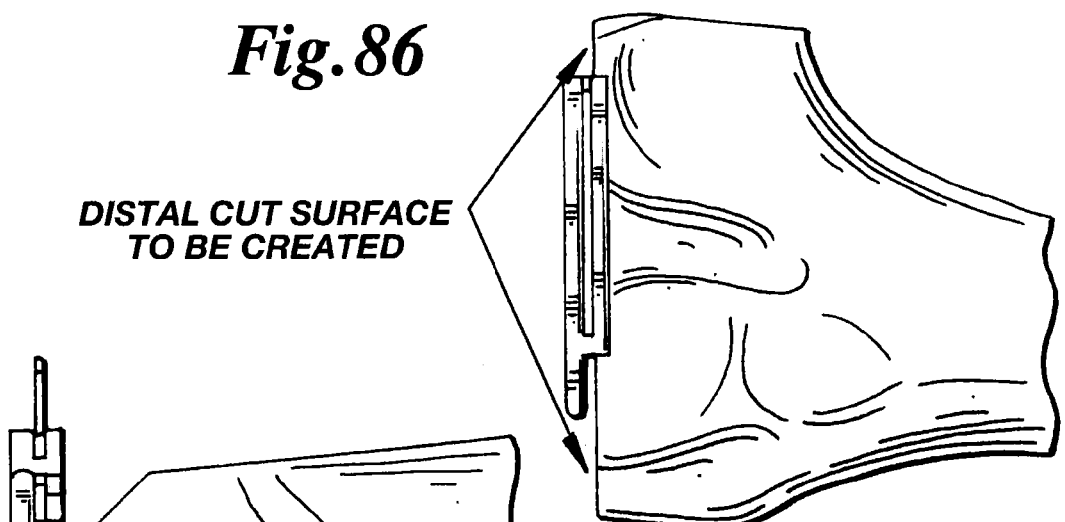
Figure 88:
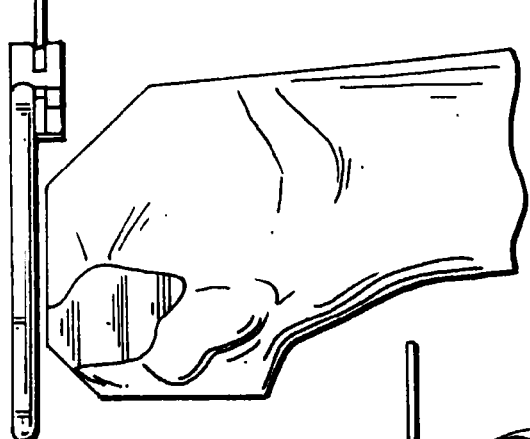
Figure 89:
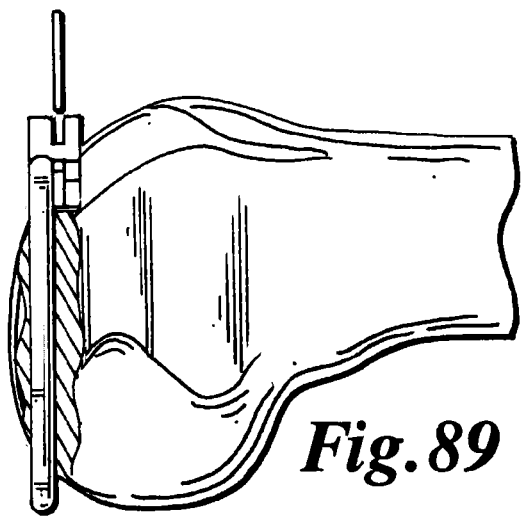
Figure 90:
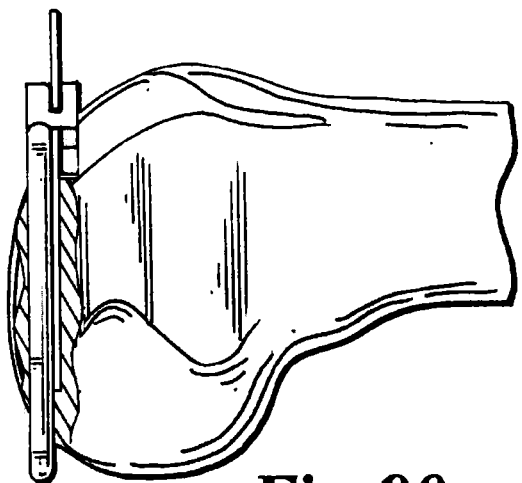
Figure 91:
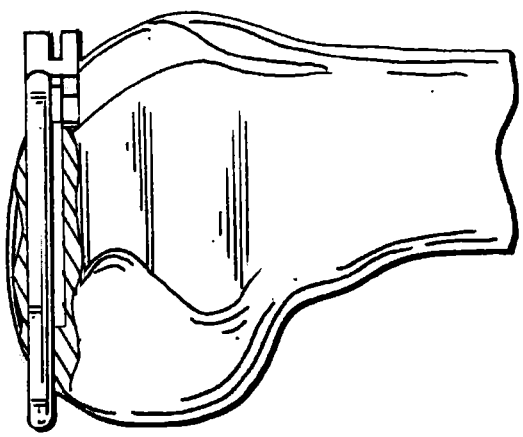

In another embodiment, the pins of the present invention could be 'split' as shown in FIG. 88. Additional guide surfaces could be incorporated into this embodiment as shown in FIG. 87 where a modular or non-modular cutting tool 'capture' is disclosed for integral or modular attachment to the pins.

Figure 93:
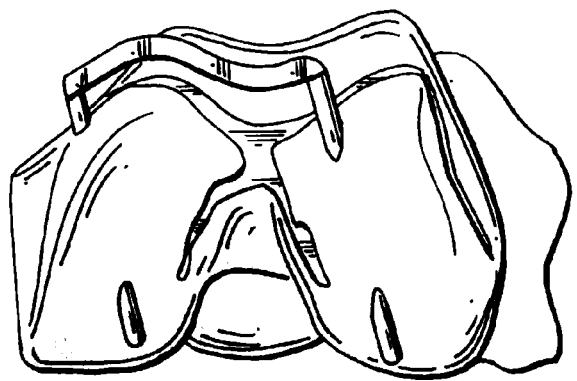

FIG. 93 shows the guide surface spanning the two pins as being biased to the medial side of the femur. This feature is intended to allow for greater ease of use in minimally or less invasive procedures without compromise of reproducibility. Also, this guide surface is somewhat wavy shaped in order to conform to the contours of the femur thus allowing placement of the guide surface as close to the cut surface as possible to increase reproducibility by reducing the cantilevering effect demonstrated in FIGS. 1 and 2, and to minimize the distraction or displacement of any soft tissue (this makes the guide both easier to insert and use while minimizing the size of the incision necessary for use). It should also be noted that the guide surface interconnecting the pins could be shaped like the symbol pi ($\pi$) where the guide surfaces extend beyond their intersection with the pins about the border of the cut(s) to be created.

Figure 94:
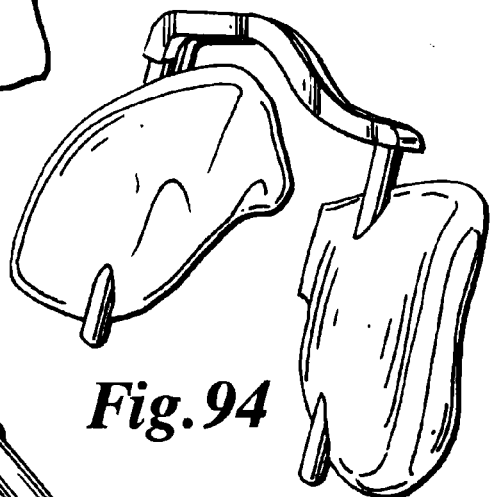
Figure 95:
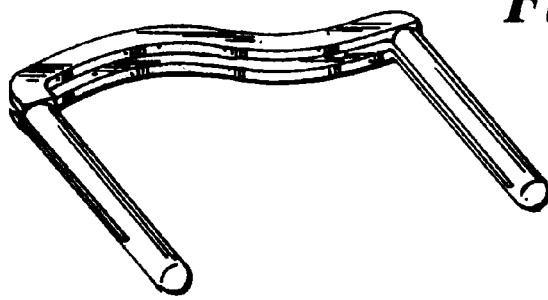

Interestingly, FIG. 94 shows that the pieces of bone to which the undercutting form of the present invention are attached may be removed from the incision after the cut is complete. This looks a bit like an olive stuck on the end of a toothpick and may reduce what is commonly referred to as 'fiddle factor.'

Figure 96:
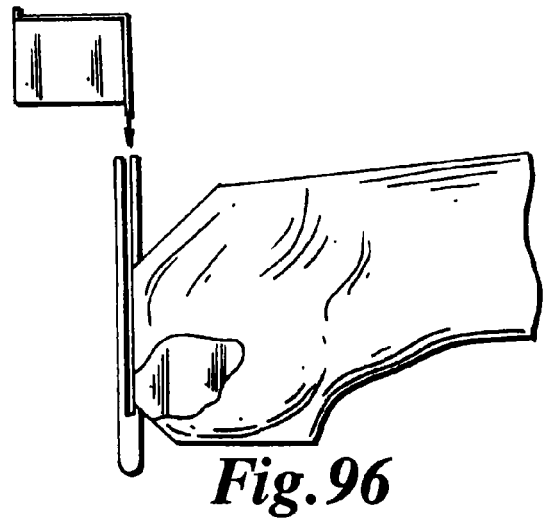
Figure 101:
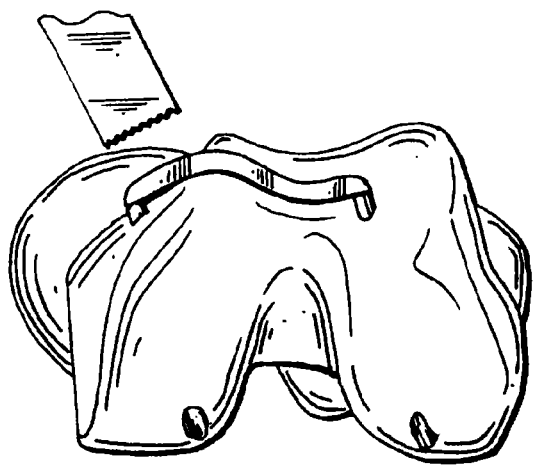
Figure 102:
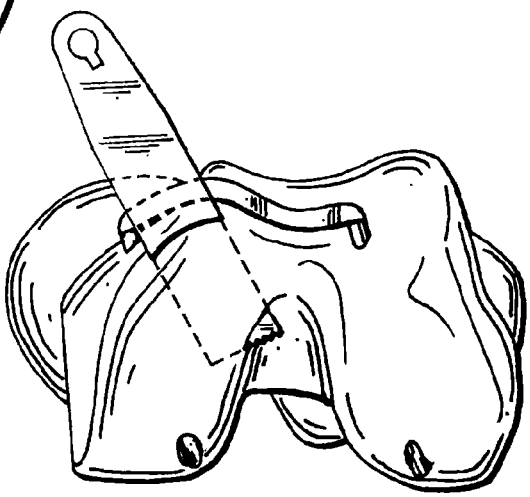
Figure 103:
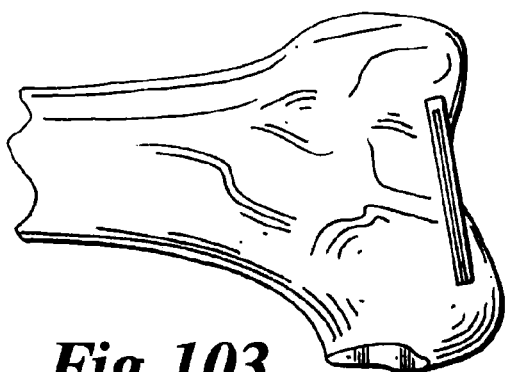
Figure 104:
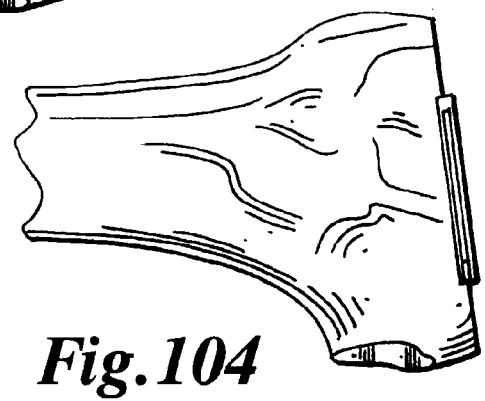
Figure 105:
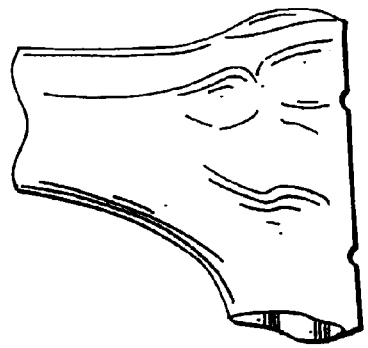
Figure 106:
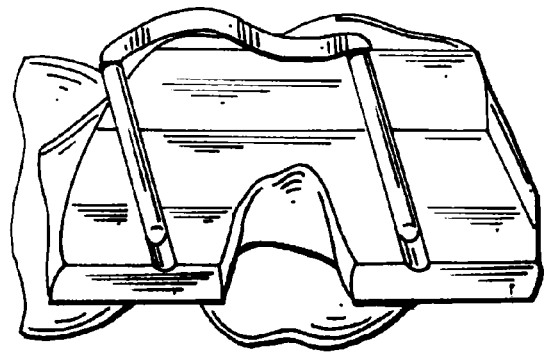
Figure 169:
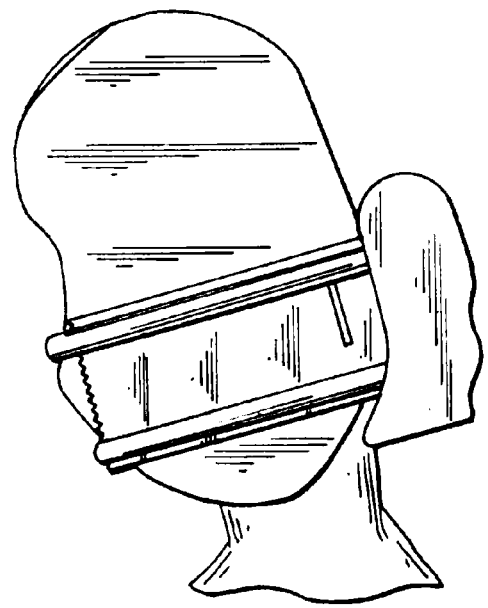
Figure 170:
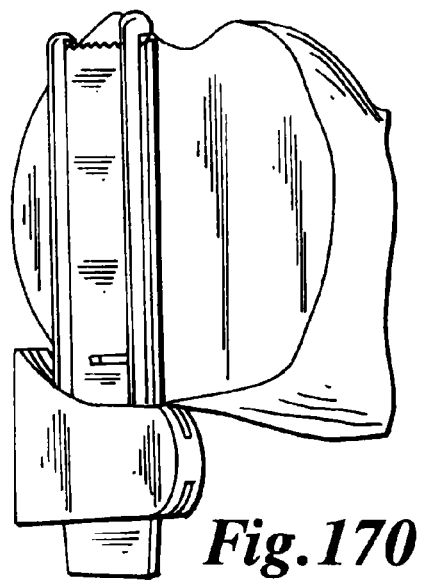

FIGS. 95 through 107 disclose various aspects of the "Split Pin" form of the present invention. This form provides for continuous or semi-continuous capture of the cutting tool in a slotted feature throughout the cutting process. FIG. 96 shows the slotted feature as extending to the point allowing for the completion of the distal cut, but not beyond. It is easily enough modified to extend the slotted feature and/or the pins to extend beyond the bone to be cut to allow for the removal of remaining bone, or the design could be as shown for situations where it is desirable to prevent movement of the cutting tool beyond a certain point to protect soft tissues (see FIGS. 169 and 170 for an example of this, and note that there are many applications where this may be desirable including endplate preparation in the spine where protecting anatomic structures such as the Spinal Cord, Aorta, and Vena Cava is of paramount importance). FIGS. 96 through 100 show a cutting tool, in this example a sagittal saw, with its long axis extending in a generally side to side direction while cutting. FIGS. 101 and 102 show a cutting tool, in this example an oscillating saw, whose long axis is extending in a generally top to bottom orientation. FIGS. 105 to 107 clearly demonstrate that the artifacts created by the use of this form of the present invention are significantly less pronounced than overcutting forms of the present invention.

FIGS. 108 through 127

Figure 108:
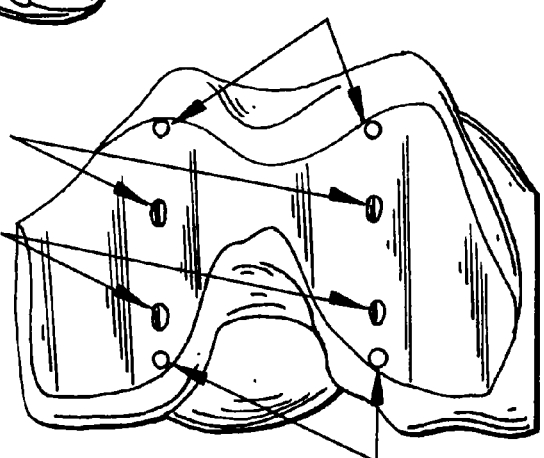
Figure 109:
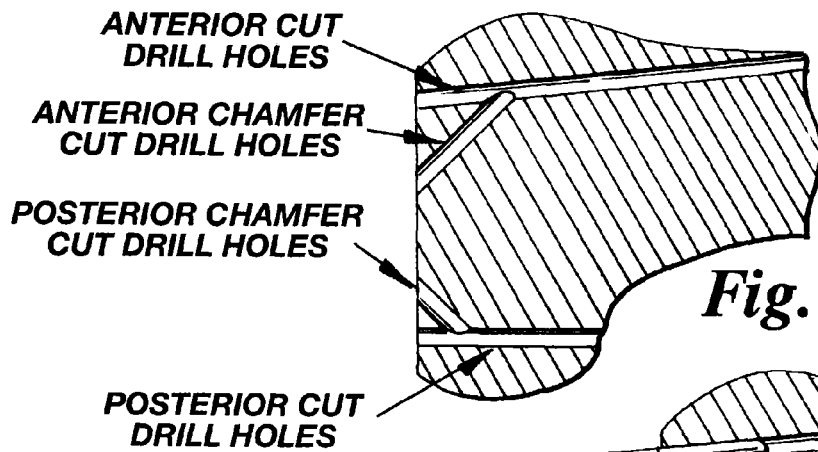
Figure 110:
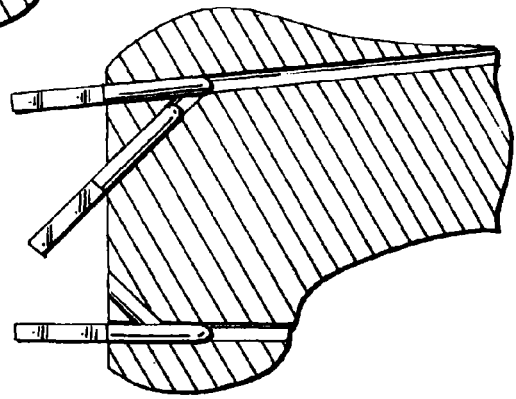
Figure 111:
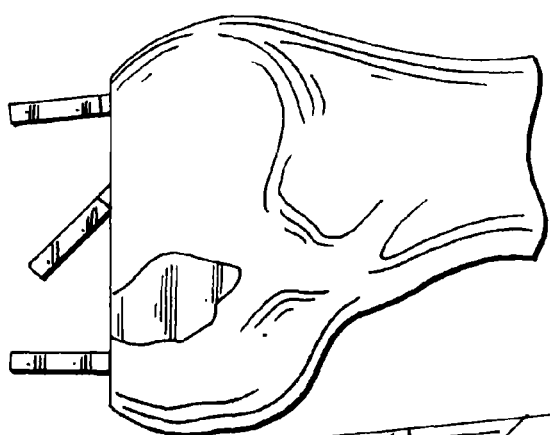
Figure 112:
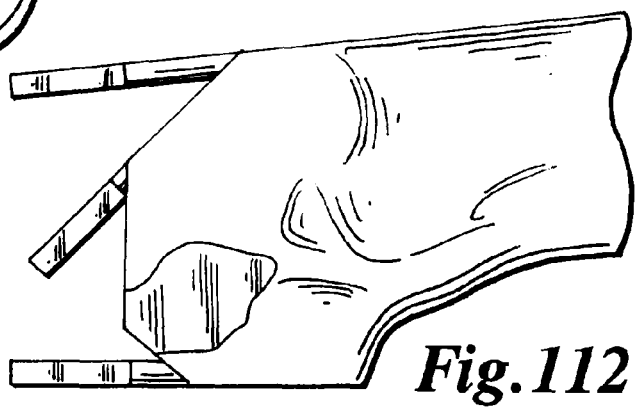
Figure 113:
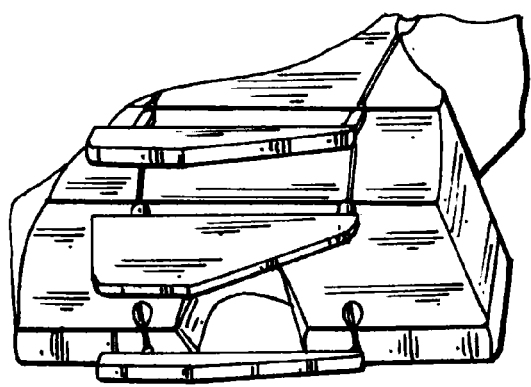
Figure 114:
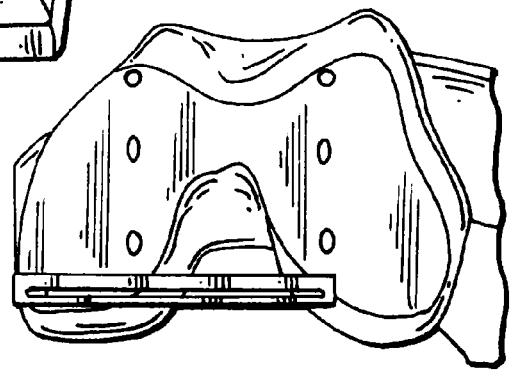
Figure 115:
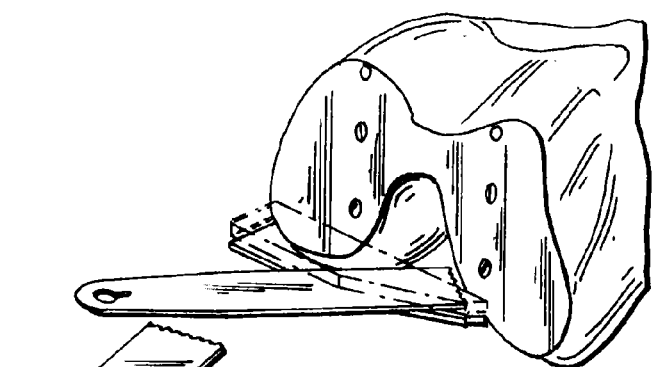
Figure 116:
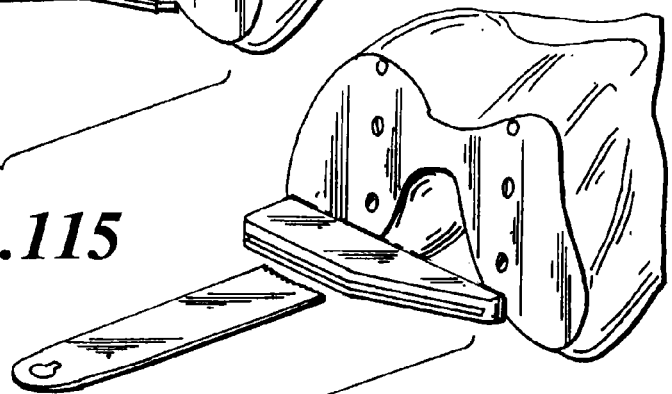
Figure 117:
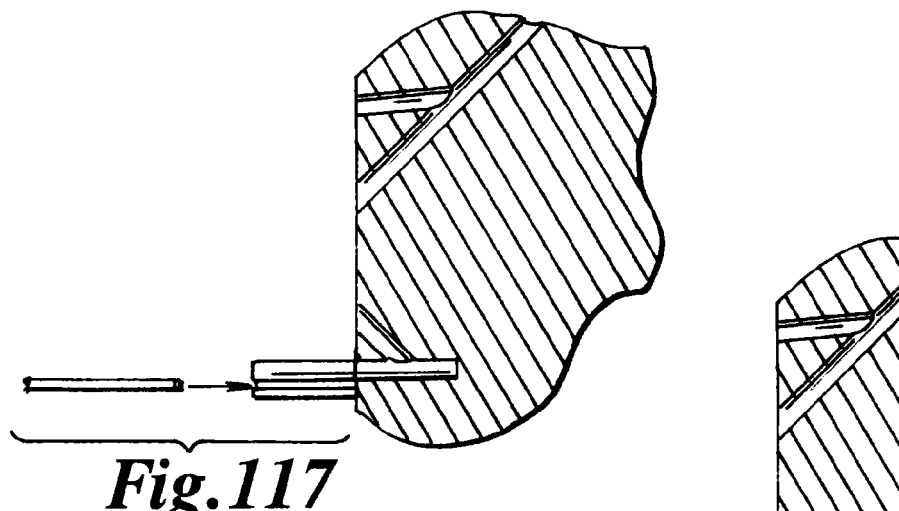
Figure 118:
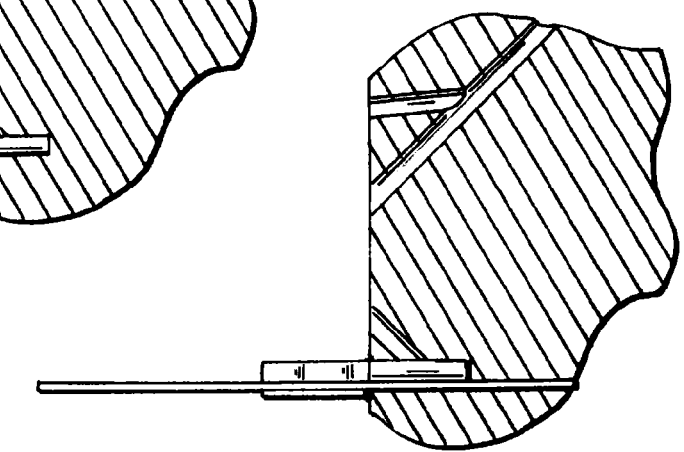
Figure 119:
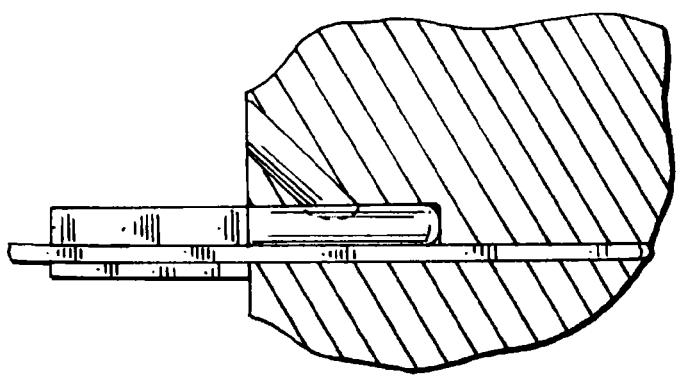
Figure 120:
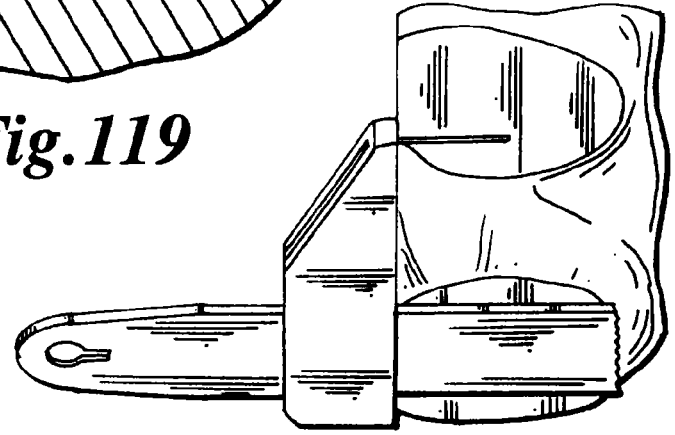
Figure 121:
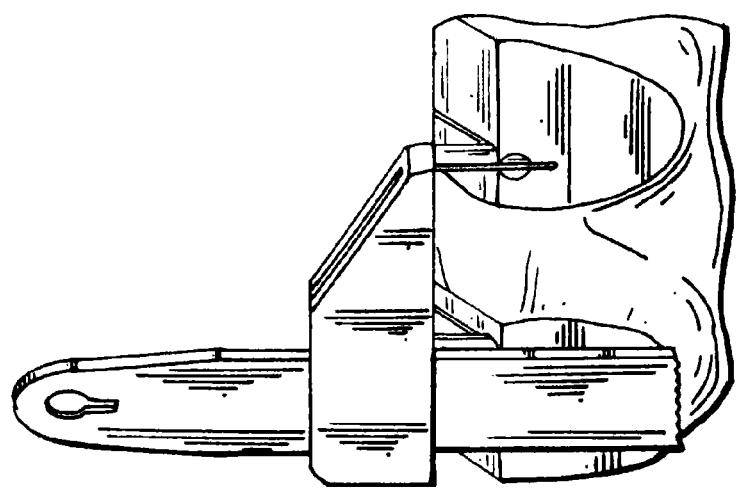

FIGS. 108 and 109 show the distal femur having been prepared to receive the cutting guide forms of the present invention that could be used to complete the remainder of the cuts. Beneficially, a single guide could be used to complete all the cuts by being incrementally attached to the bone at the appropriate locations as shown in FIGS. 110 through 121. Alternatively, a modified '4 in 1' cutting block designed to engage the pins of the present invention could be used. The modified '4 in 1' block could further be modified by being vertically cut in half and having the pins extending laterally of the block to provide guidance of the cutting tool laterally beyond the location of the conventional guide surfaces. FIGS. 114 through 121 show a capture feature added to the guides previously shown in FIG. 113. Note that FIG. 120 demonstrates that despite the abbreviation of the laterally located guide surfaces (to facilitate medial incision based procedure), the cutting tool remains robustly guided by the guide of the present invention when both the medial and lateral side of a bone is cut. Note that this design is shown to facilitate a medial approach and thus the guide has been 'medialized' to minimize necessary incision size—if a lateral approach were implemented, a 'lateralized' form of the present invention could be made available.

Figure 122:
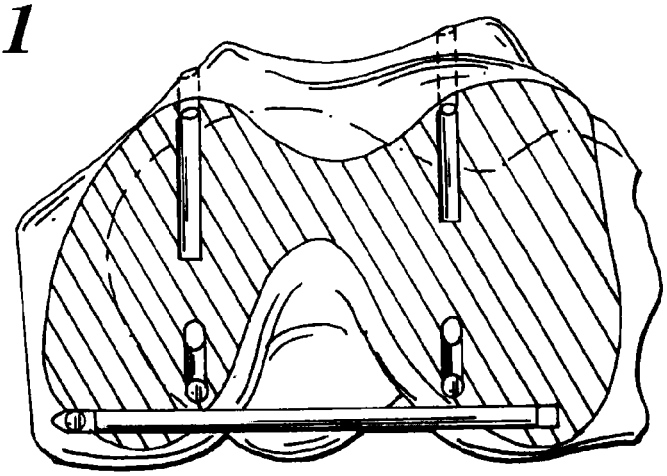
Figure 123:
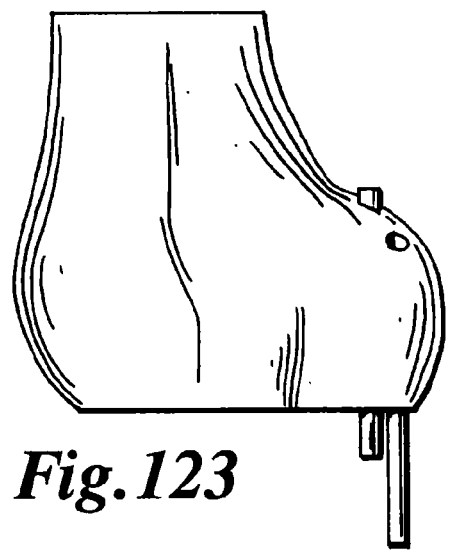
Figure 124:
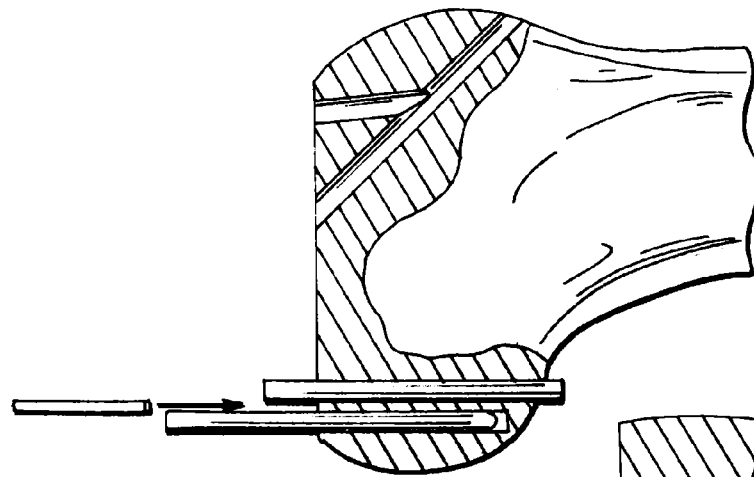
Figure 125:
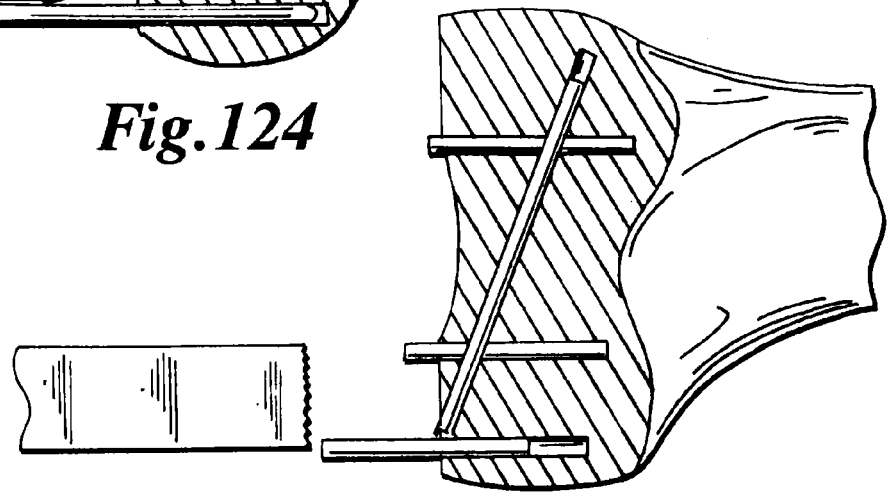
Figure 126:
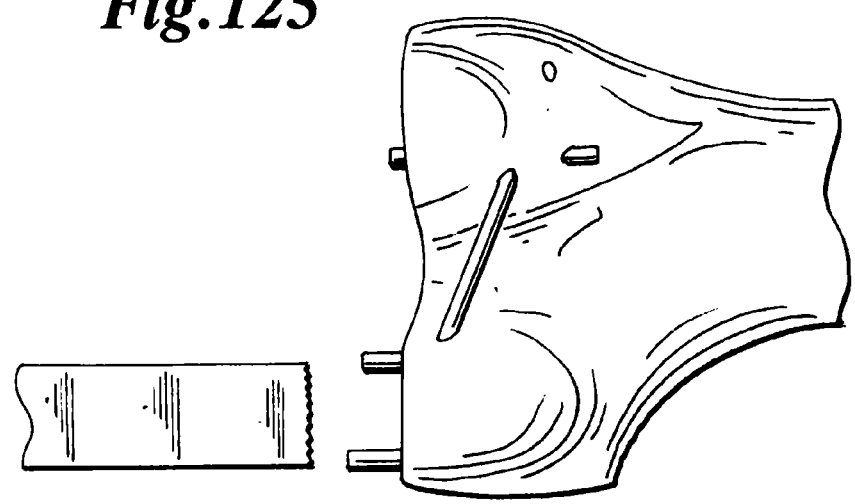
Figure 127:
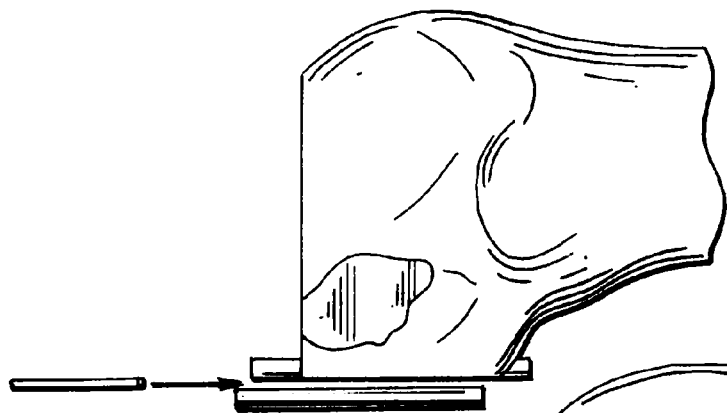
Figure 128:
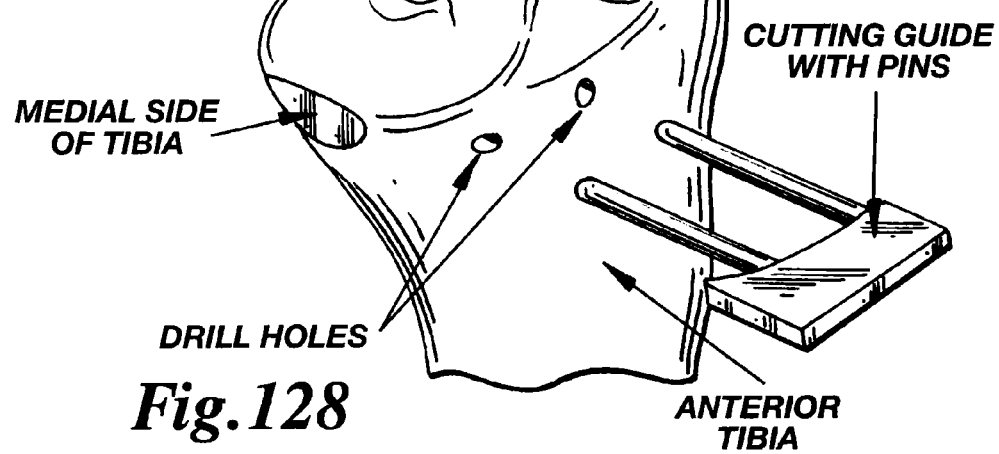
Figure 129:
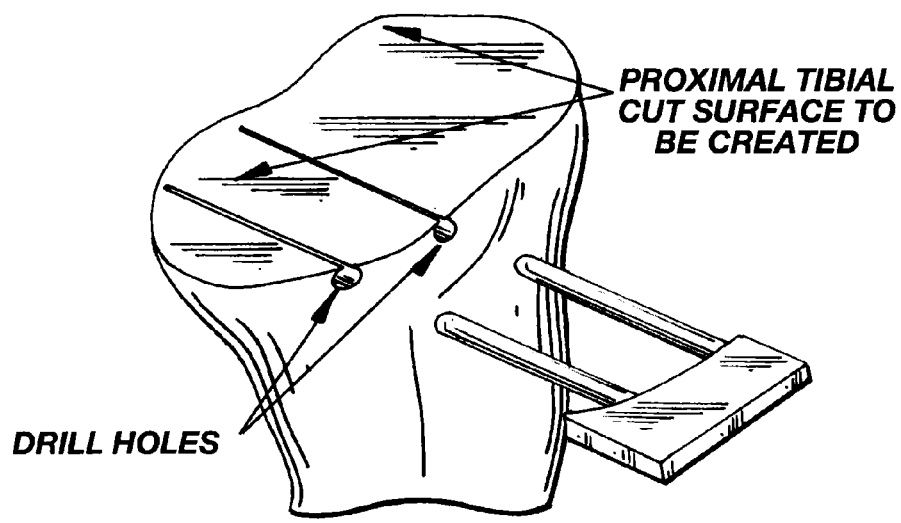
Figure 130:
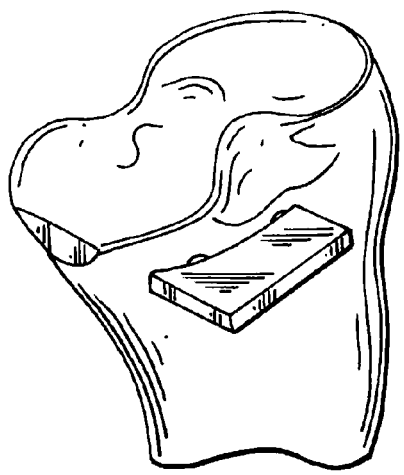
Figure 131:
Figure 132:
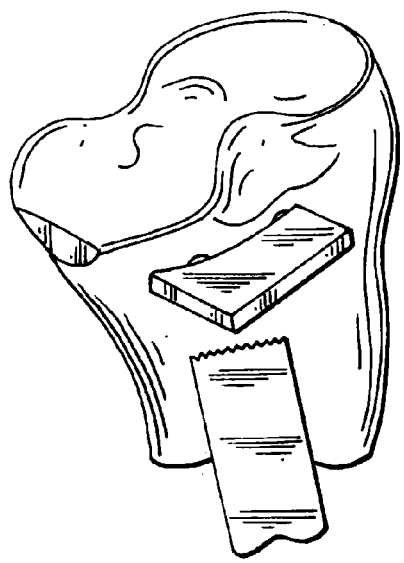
Figure 133:
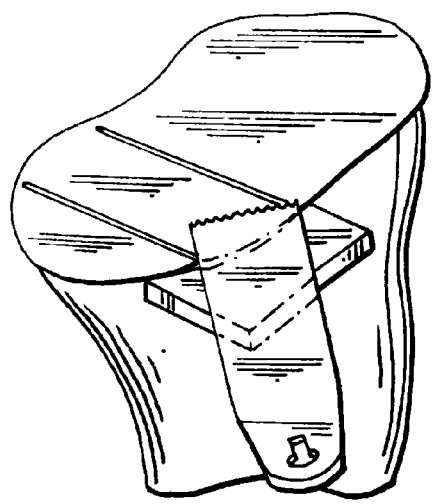
Figure 134:
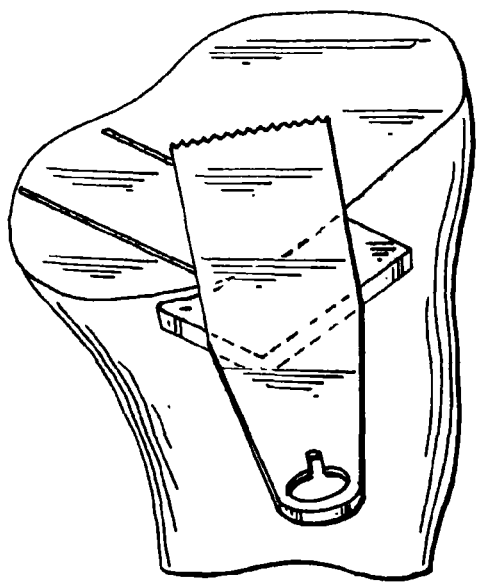
Figure 135:
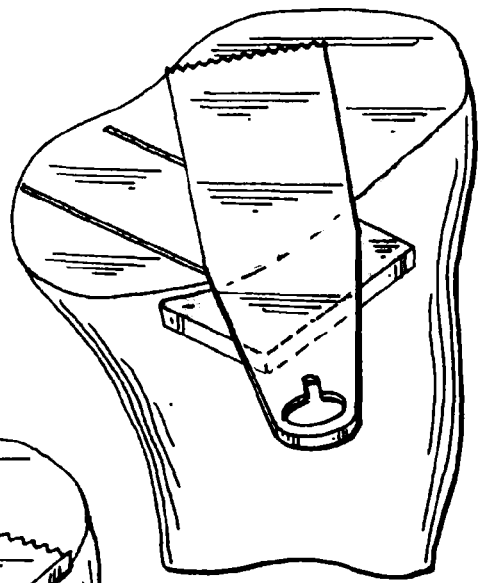
Figure 136:
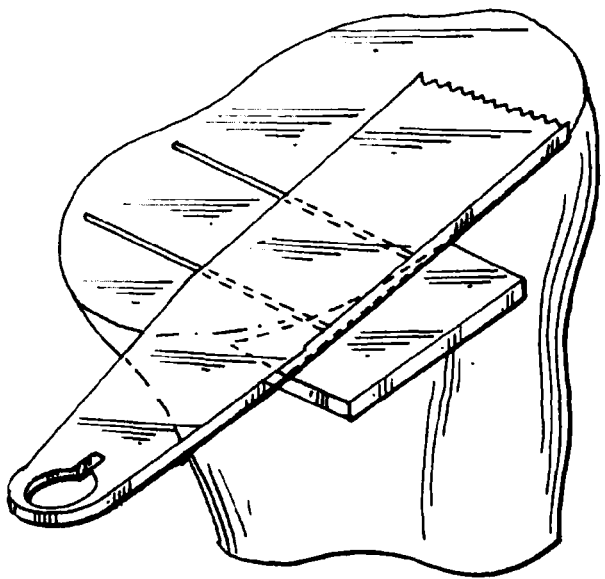
Figure 137:
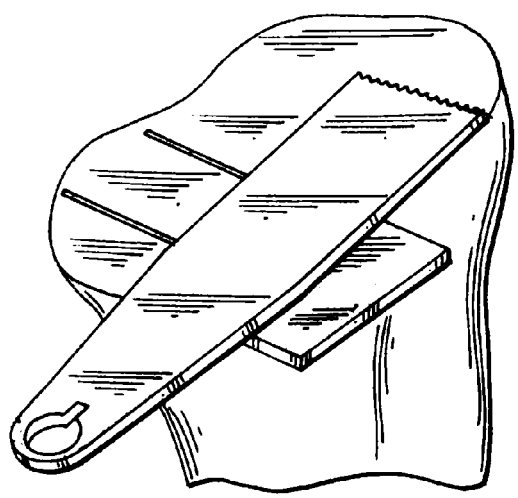
Figure 138:
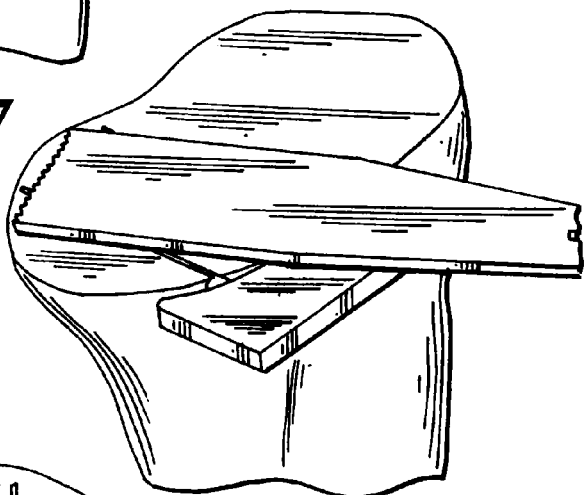

FIGS. 122 through 127 show some of the combinations of the forms of the present invention in use to complete the posterior cut. As shown in FIGS. 122, 125, and 127, two pins are located in overcutting mode, while two other pins are shown in undercutting mode. The combination of these pins acts to constrain motion of the cutting tool from traveling beyond the plane to be cut. For the sake of clarity, any combination of the forms of the present invention disclosed herein may be modified or combined to form constructs not specifically disclosed herein, but still within the scope of the present invention.

FIGS. 128 through 148

Tibial resection in TKA can be somewhat frustrating to a certain percentage of orthopedic surgeons. This frustration appears to stem from the high demands upon the surgeon's manual skills or craftsmanship. The forms of the present invention may help alleviate this issue by providing positive guidance of the cutting tool throughout all or most of the cutting process. Also, it should be noted that these concepts allow for implementation with very small incisions.

FIGS. 128 through 148 disclose a number of different forms of overcutting type pins/guides. Cutting tool captures are not shown, but could be seperably attached or formed integrally with the guide or pins. It is important to note in FIG. 136 the extent to which this and other forms of the present invention allow for contact with and guidance of the cutting tool. The solid lines (shown in yellow) show approximately where an oscillating saw would contact the pins, while the dashed lines (shown in yellow) outline the contact area between the saw and the guide surface bridging the pins. This creates a very stable surface for guiding the cutting tool. It should be noted that undercutting forms of the present invention could be used with guides or pins of similar configurations.

Figure 139:
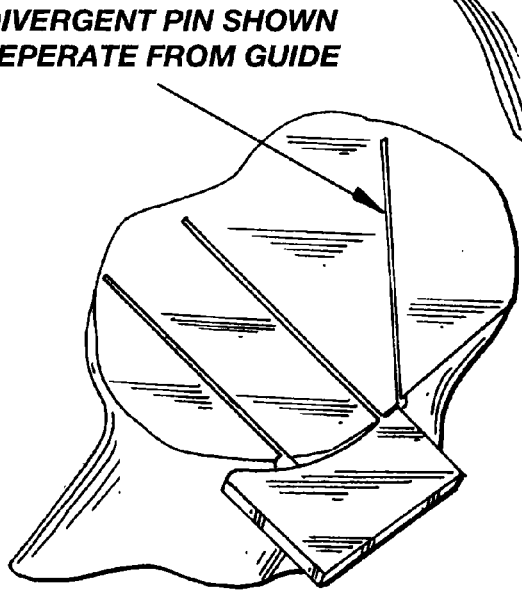
Figure 155:
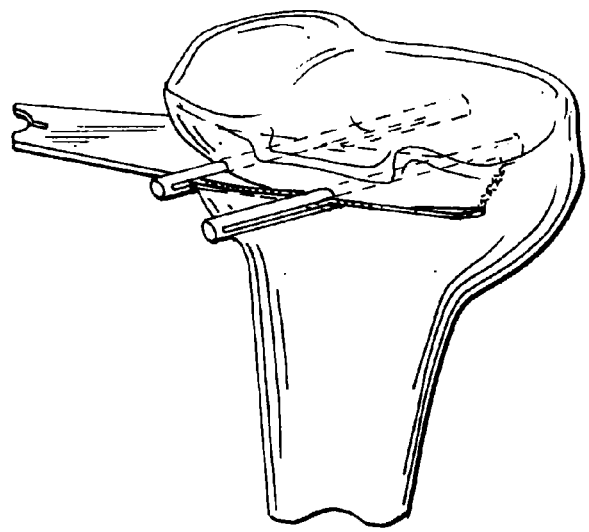
Figure 156:
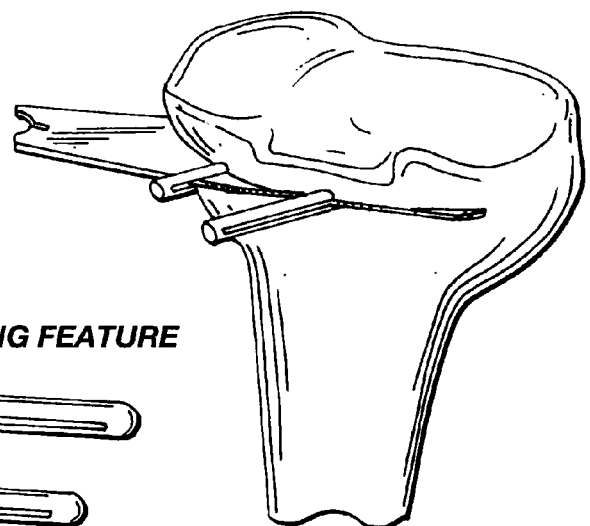
Figure 157:
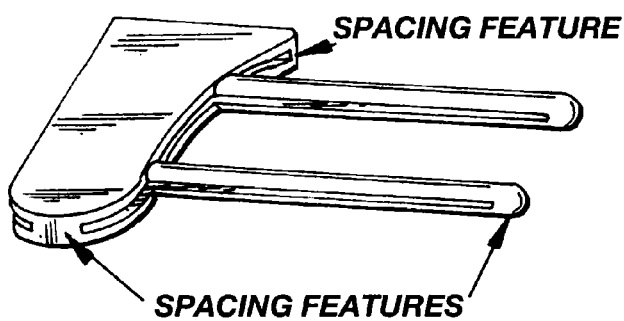
Figure 158:
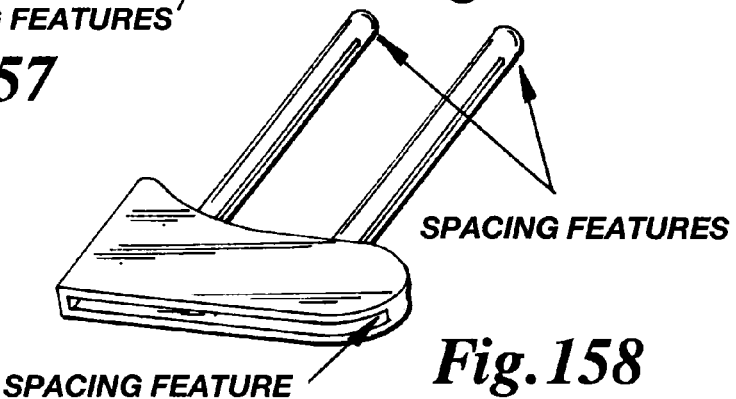
Figure 159:
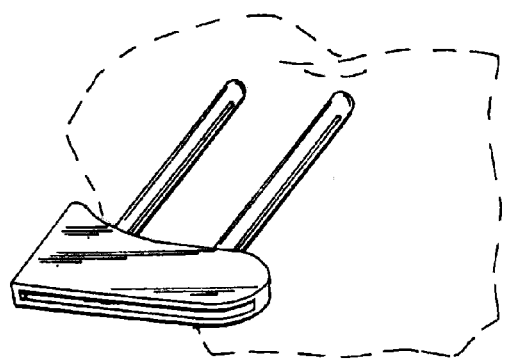
Figure 160:
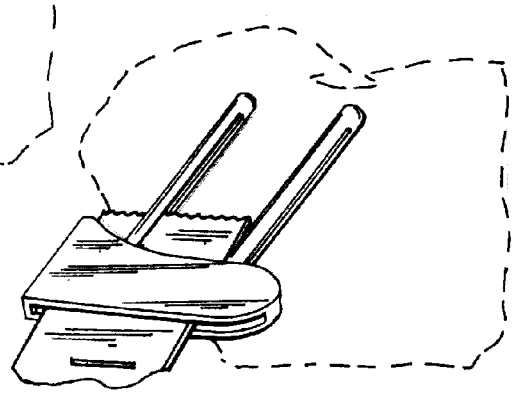
Figure 161:
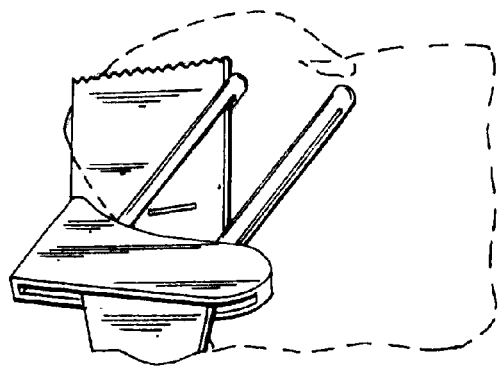
Figure 162:
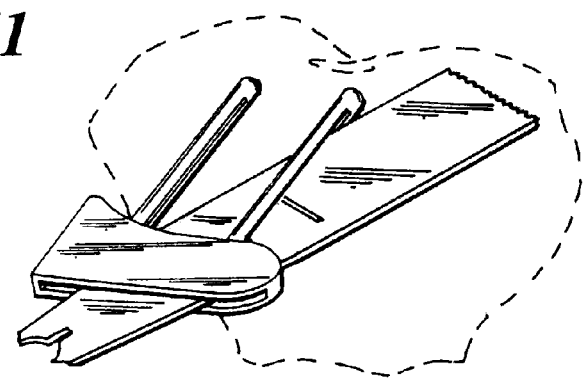
Figure 163:
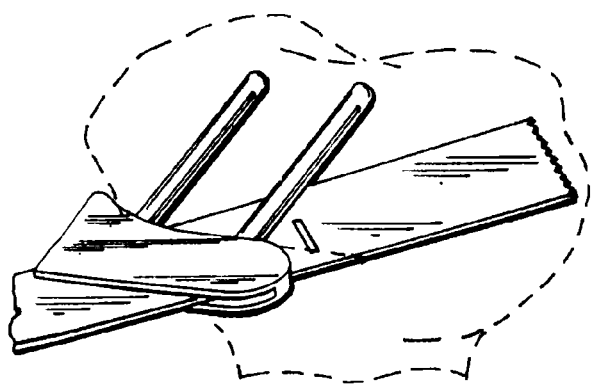
Figure 164:
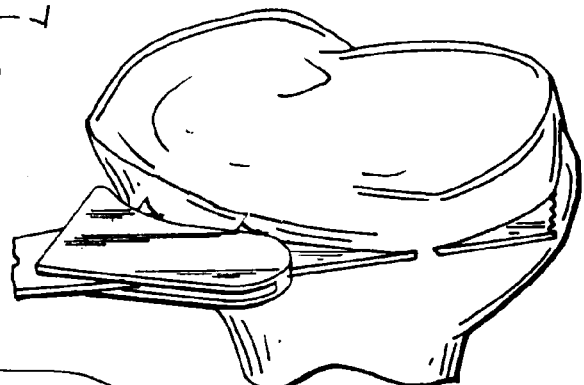

FIGS. 139 through 148 show a pin or pins which are not physically interconnected with a guide surface. FIG. 139 shows a pin embedded in the tibia that is in no way attached to the other components of the pin guide. It should be noted that it could easily be engaged to some form of mating feature in the guide surface bridging the other two pins shown, if desired. FIG. 141 very importantly shows that a plurality of pins which are not interconnected could be positioned entirely within bone, or with very little of their material extending beyond the surface of the bone. This embodiment allows for extremely small incisions to be utilized while maintaining excellent cutting tool guidance.

FIGS. 142 through 148 show two independently fixed pins extending beyond the surface of the bone enabling contact between the pins and the cutting tool prior to penetration of the cutting tool into the bone. Movement of the cutting tool along the pins can be generally parallel to the long axis of the pins (as shown in FIGS. 142 to 144) or transverse to the long axis of the pins (as shown in FIGS. 145 to 148), but it will likely be desirable to implement both forms of tool manipulation to complete the cutting process.

FIGS. 149 through 170

FIGS. 149 through 156 show a split pin form of the present invention for tibial resection. Although an oscillating saw is disclosed in these figures, a multitude of cutting tools could be implemented for use with this and other forms of the present invention. A sagittal saw is one obvious choice, but perhaps a side cutting milling tool would yield even more superior results while avoiding damage to the soft tissue structures surrounding the joint. Once again, the split pin form enables a less significant artifact.

Figure 165:
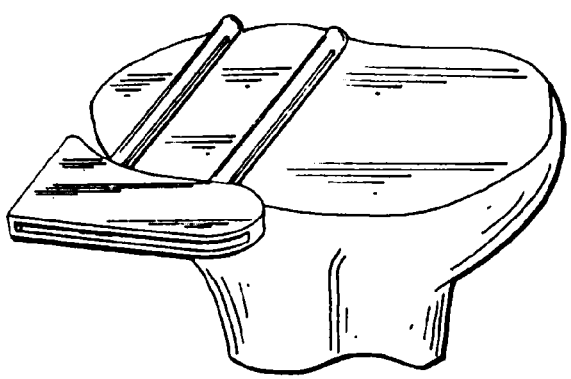
Figure 166:
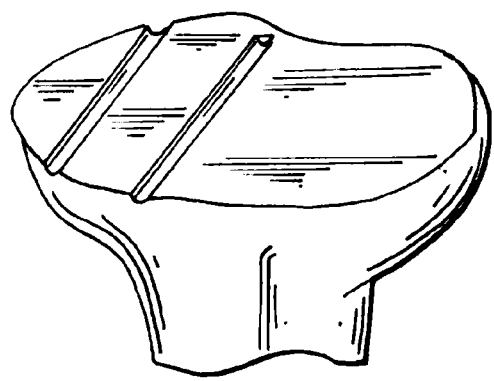
Figure 167:
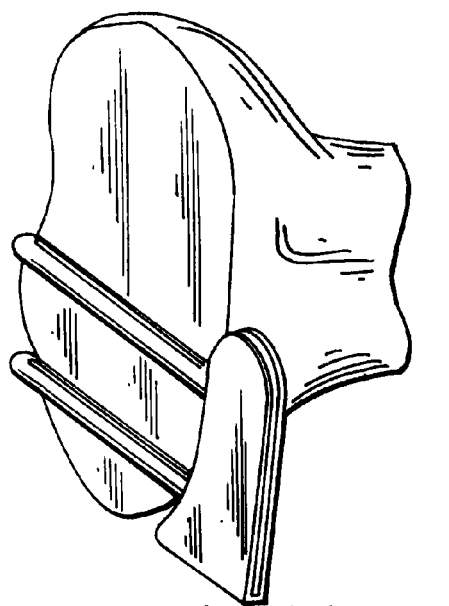
Figure 168:
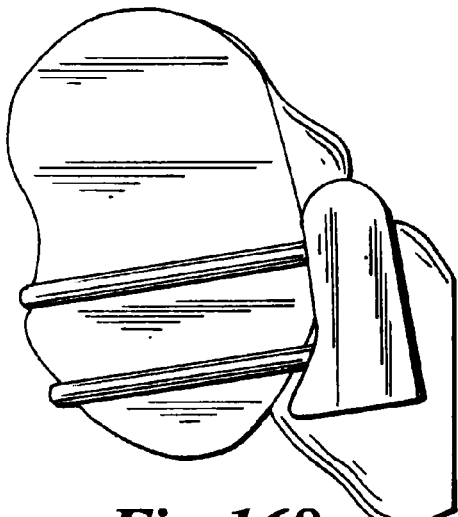

FIGS. 157 through 170 show a split pin with bridging guide surfaces. Importantly, one potentially problematic issue with the split pin forms of the present invention may be the tendency of the slots to collapse or partially close preventing easy passage of the cutting tool along the pins. To avoid this, and the debris generation it would likely create, one embodiment of the guide possesses spacing features (see FIGS. 157 and 158) to prevent collapse of the surfaces that guide the cutting tool. Comparing FIGS. 165 and 167 shows that the pins can be extended partially across the surface to be cut, or entirely across the surface to be cut. This principal of operation could be critical in protecting the vascular and nervous structures posterior of the posterior capsule of the knee joint from accidental damage through contact with the cutting tool. This is more clearly shown in FIGS. 169 and 170 where the spacing features act to prevent the cutting tool from extending beyond the cut surface and into anatomic structures that must be preserved and protected from harm. This cost of damaging these anatomic structures could be the ability of the patient to walk or could require amputation due to nervous or vascular compromise.

FIGS. 171 through 186 and 190 through 193

FIGS. 171 through 186 and 190 through 193 describe another embodiment of the present invention. The device overcomes the drawbacks of the inability to easily and accurately secure existing alignment or guide systems to a desired location or position, a problem often referred to as the fiddle factor problem. The fiddle factor problem extends intraoperative time, creates surgeon frustration and can lead to implant mal-alignment due to inaccurate alignment guide or cutting guide positionings.

Figure 181:
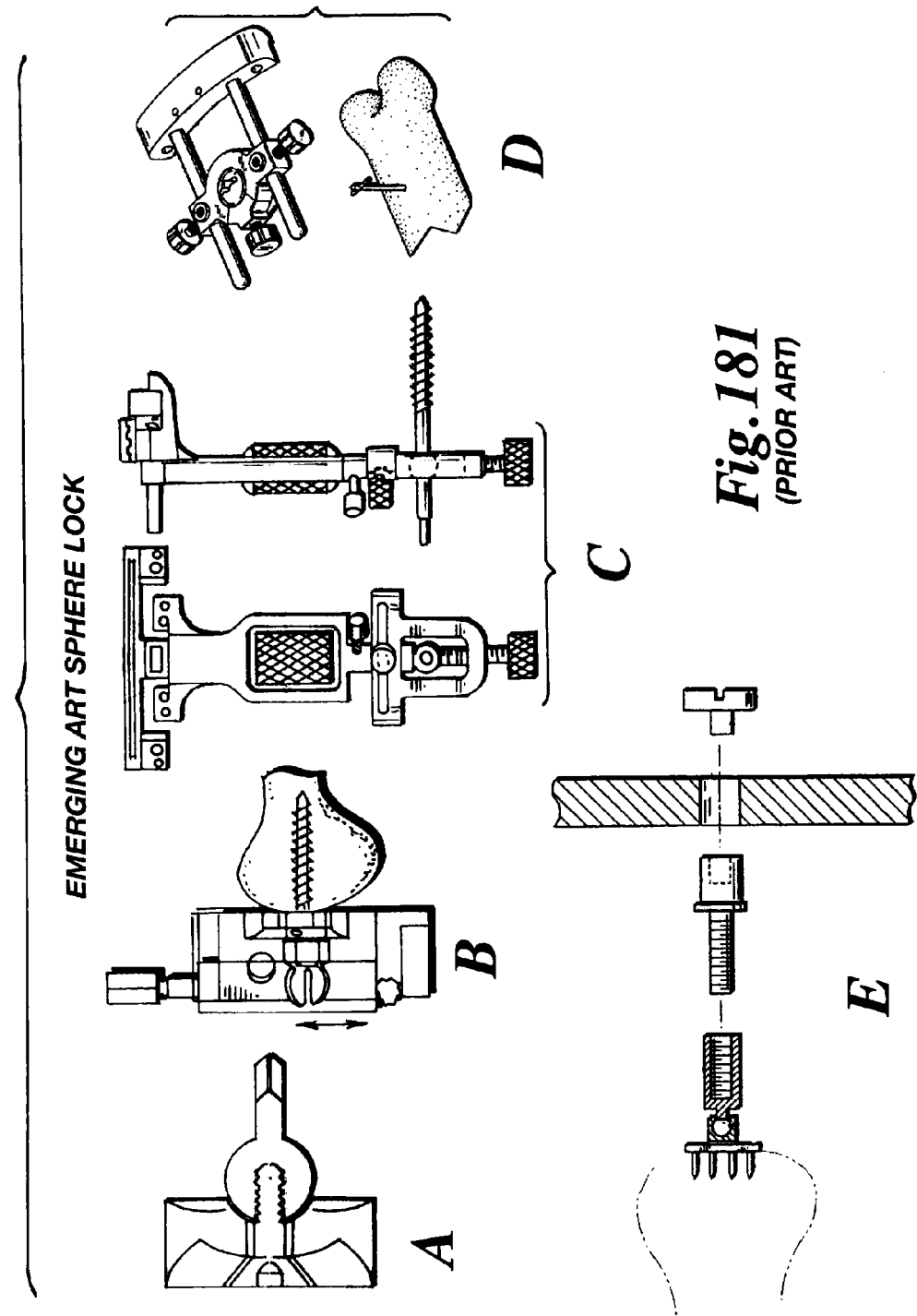

An example of the fiddle factor problem in existing alignment and guide systems is shown, for example, in the device by Grimm described in U.S. Patent Publ. No. 2004/0122436 (herein incorporated by reference). As shown in FIG. 181 of this application, it will be observed that the actuation of the locking mechanism generally indicated as 34 to fix the carriage 40 with respect to the sphere 22 will actually cause the carriage 40 to rotate with respect to sphere 22. Thus in use, the surgeon would attain the correct location and orientation of the cutting tool guide of Grimm, as indicated on the computer display, and then attempt to lock varus valgus, flexion extension, and internal/external rotational alignment by way of the actuation of locking mechanism 34, but in doing so, the carriage, and thereby the cutting tool guide would shift from the desired orientation. This dynamic will force the surgeon to iteratively tighten the lock, adjust the carriage, tighten the lock a little more, adjust the carriage a little more, tighten the lock even more, adjust the carriage a little more, etc., until intraoperative time constraints would compel the surgeon to move forward with the procedure with alignment that is suboptimal. These problems can be compounded by several additional adjustment and locking mechanisms to similarly fiddle that need to be made prior to making the first cut.

Simply put, the major problem with the majority of surgically navigated "anchor-cutting guide linkage" type devices (such as those applications identified in FIG. 181 which are herein incorporated by reference) is that the act of locking the orientation and location of the cutting guide in place with respect to the anchor and/or the desired implant location and orientation actually causes the location and orientation of the cutting guides to change, in some cases radically. As the ultimate objectives of surgical navigation are to improve accuracy and promote and facilitate minimally invasive implantation, the fiddle factor problem clearly runs counter to these objectives. One can clearly see this problem in effect by reviewing those devices described in patent or patent application numbers shown in FIG. 181, which are herein included by reference.

This embodiment of the present invention solves the fiddle factor problem by providing for an elegant locking mechanism that secures a plurality of translation and rotational degrees of freedom in a manner which fails to shift the location and orientation of the cutting tool guide while it is being secured. More precisely, the sum of the force moment couples acting about the center of mass of the cutting tool guide(s) by the actuation of the locking mechanism are governed by the following equation:

$$\Sigma M_{(x,y,z)} + \Sigma F_{(x,y,z)} = 0 \quad (1)$$

M=moments about three mutually orthogonal axes

F=forces about three mutually orthogonal axes

Figure 171:
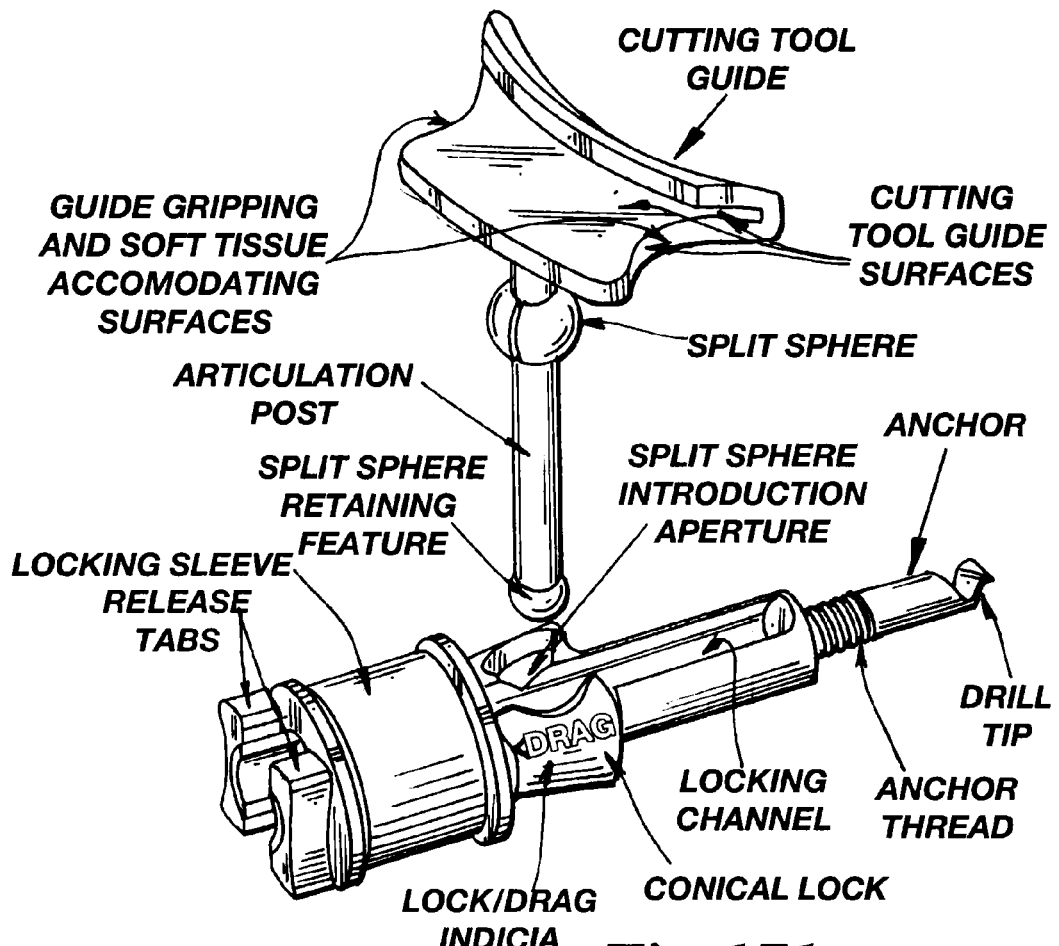

The primary components of this embodiment of the present invention are shown in FIG. 171. These include the anchor (see also FIG. 175), the locking sleeve (see also FIGS. 177 through 180), the split sphere (see also FIG. 174), the cutting tool guide (see also FIGS. 176, 193, and 218), and the Surgical Navigation Sensor (not shown for the sake of clarity and will herein be referred to simply as a "sensor").

Figure 182:
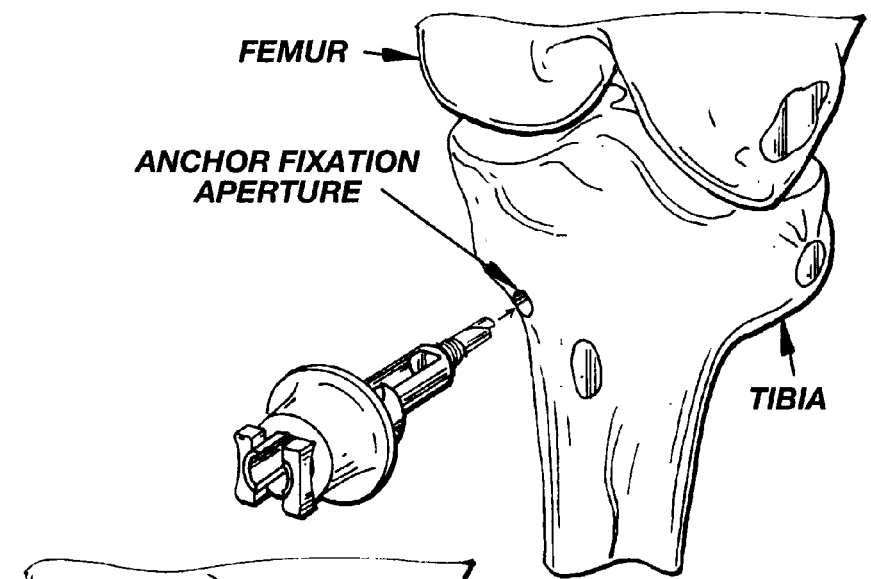
Figure 183:
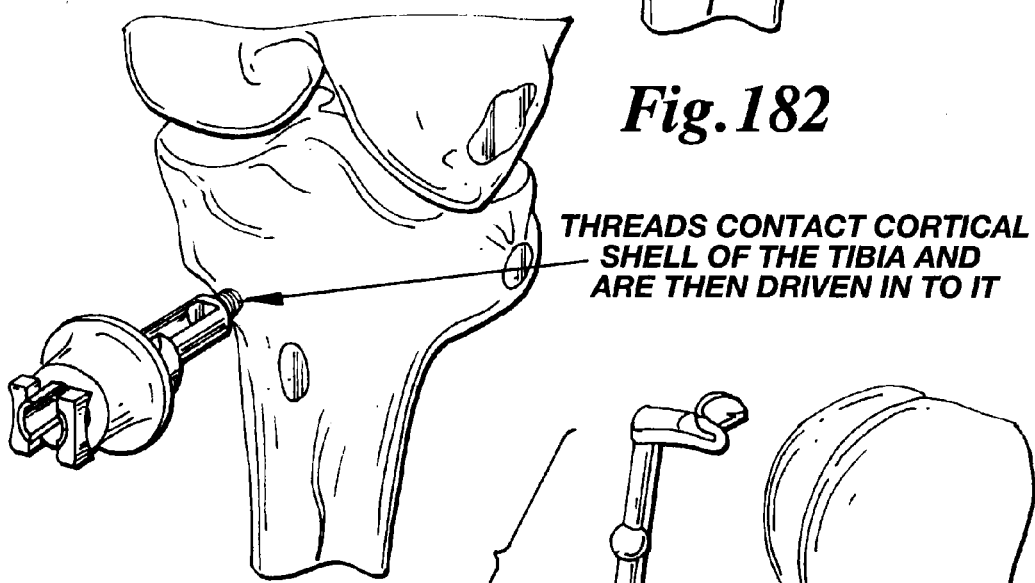
Figure 184:
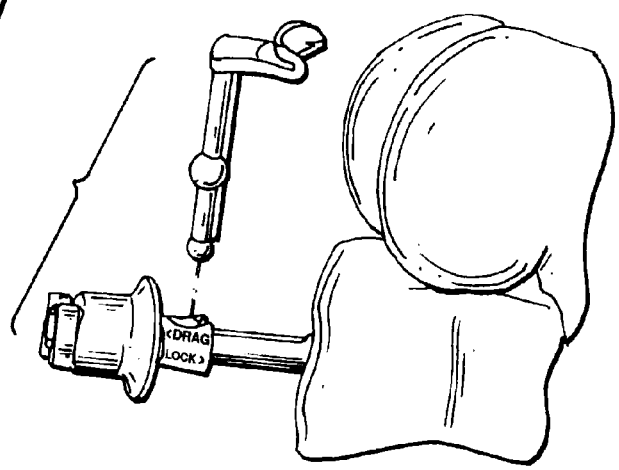
Figure 185:
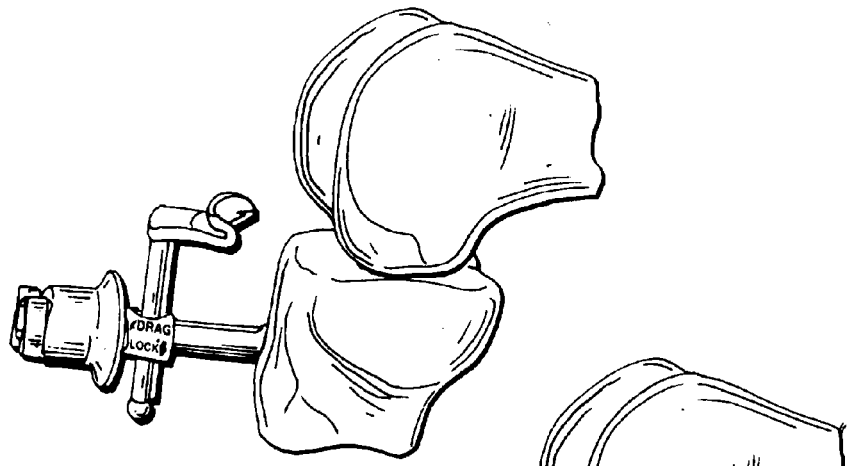
Figure 186:
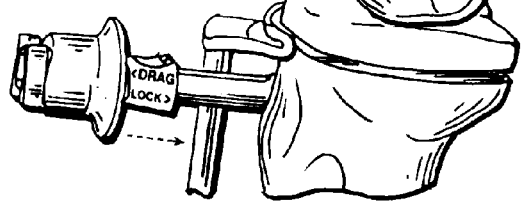

The anchor possesses four primary features, either alone or in combination with the primary components of this embodiment of the present invention. Those features include a bone penetrating and anchor stabilizing feature (indicated as the anchor thread in FIG. 171 and the drill tip in FIG. 171), a locking feature (indicated as the conical lock in FIG. 171), a linkage engagement feature (indicated as the locking channel in FIG. 171), and a quick release feature (indicated as the release tabs in FIG. 171). In use, the anchor may be drilled into and fixed to a face of the bone in one continuous or semi-continuous step, or an aperture may be predrilled to which the anchor is subsequently fixed (as shown in FIGS. 182 and 183). If pre-drilling is used, a simple template (not shown) including a faux guide surface, drill guide aperture, and handle may be used for the purpose of facilitating the surgeon's "eyeball" placement of the pre-drilled aperture; in other words, the faux guide surface acts as a general indication of where the surgeon thinks the cut is to be located simply based on how it looks relative to the bone based on the surgeon's judgment/experience to facilitate pre-drilled aperture placement for the anchor enabling minimal adjustment of the cutting tool guide with respect to the anchor.

Figure 172:
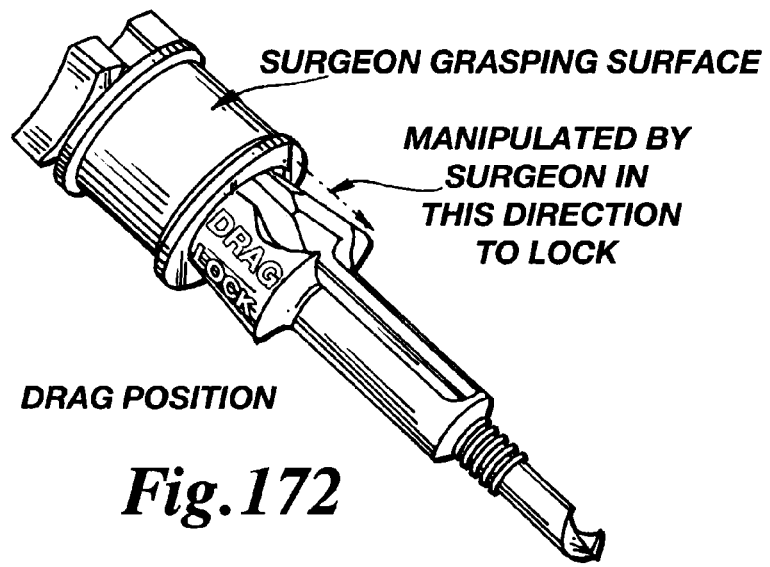
Figure 173:
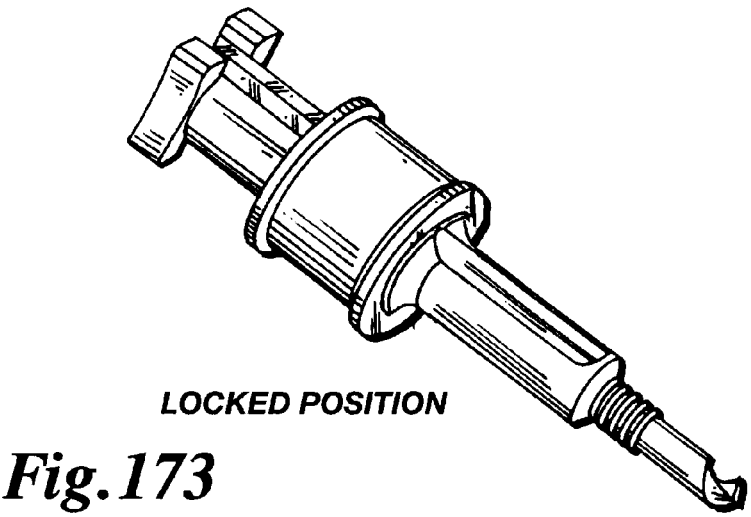

The locking sleeve possesses three primary features alone or in combination with the primary components of the embodiment of the present invention including a drag feature (indicated as the O-ring in FIG. 178), a locking feature (indicated as the cone contacting edge in FIG. 177), and a surgeon grasping surface (indicated in FIG. 172). These features coact to enable rapid and effective locking and quick release of the cutting tool guide with respect to the anchor. The drag feature coacts with the anchor, split sphere, and cutting tool guide to affect frictionally resisted movement of the cutting tool guide with respect to the anchor about 3, 4, 5, 6, 7, or 8 degrees of freedom.

Figure 174:
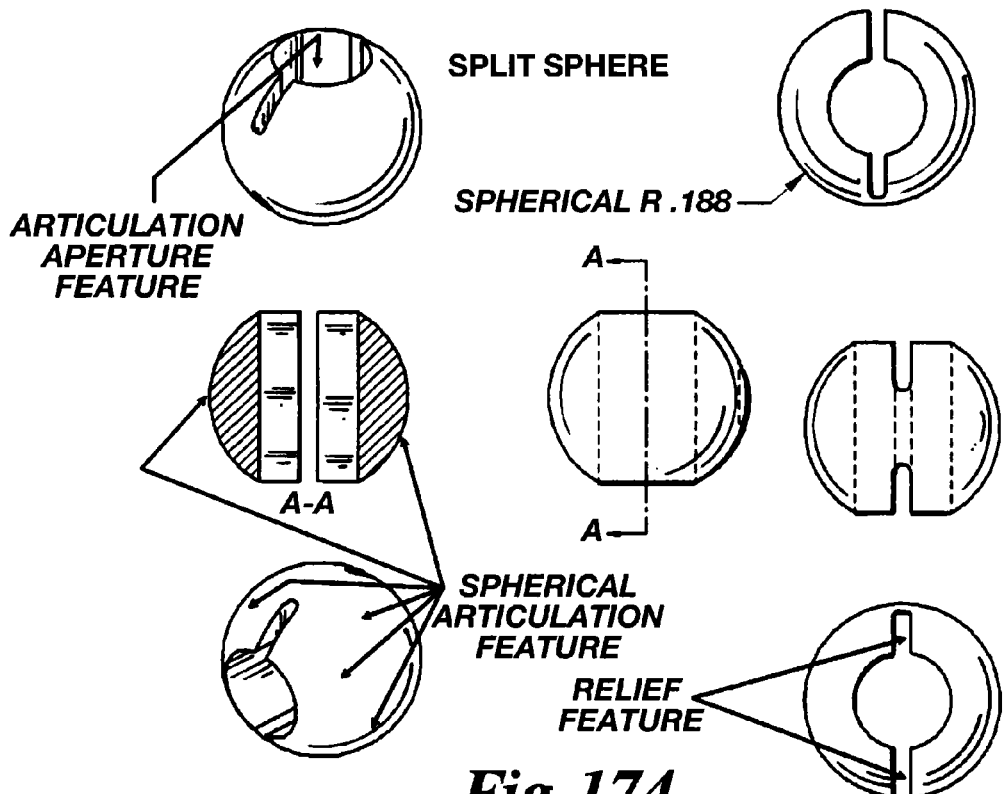
Figure 175:
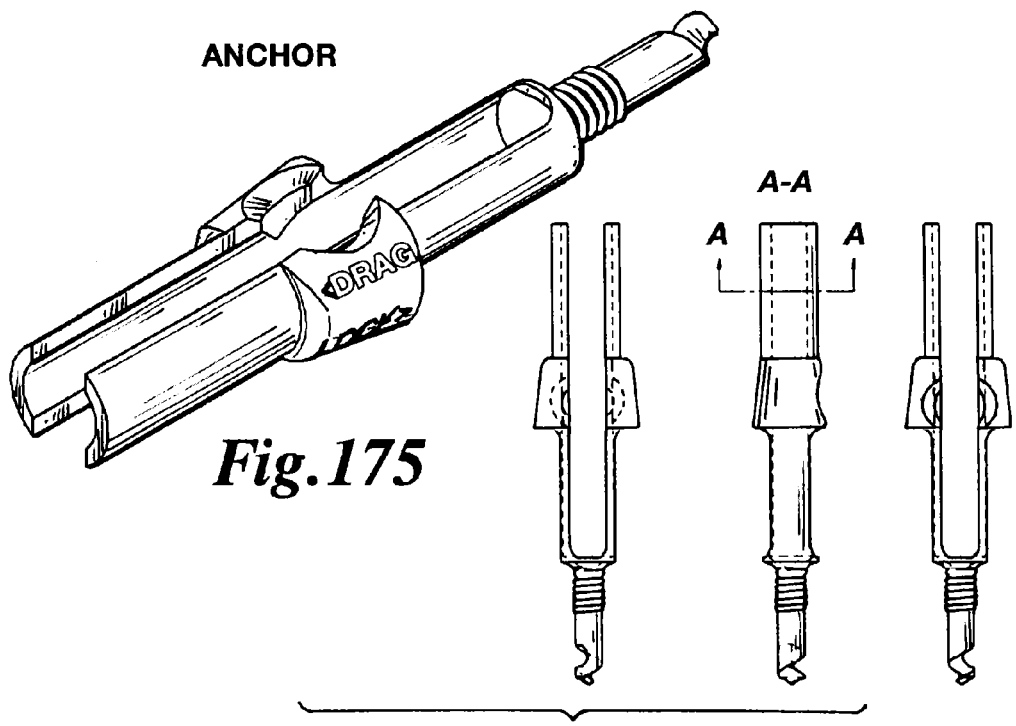

The split sphere, in this embodiment of the invention, possesses three primary features alone or in combination with the primary components of the embodiment of the present invention including an articulation aperture feature (indicated in FIG. 174), a spherical articulation feature (indicated in FIG. 174), and a relief feature (indicated in FIG. 174). As may be seen in FIG. 171, and by comparing FIGS. 190 & 191, the articulation aperture feature of the split sphere coacts with the articular post of the cutting tool guide to enable frictionally resisted movement and frictionally affected locking of the cutting guide with respect to the split sphere. When enabling frictionally resisted movement (herein described as "drag mode"), the amount of force against which this mechanism must resist movement of the cutting tool guide with respect to the anchor is at least equivalent to the force affected by way of gravity, and in preferred embodiments, is at least equivalent to the combination of force affected by gravity and the force affected by soft tissue contacting the device. When enabling frictionally affected locking (herein described as "locking mode"), the amount of force against which this mechanism must resist movement of the cutting tool guide with respect to the anchor, in a preferred embodiment, is at least equivalent to the force moment couples the applied to the device by the combination of gravitational, soft tissue, and cutting tool contacting forces. To further facilitate the effectiveness of these modes, the internal and external surfaces of the split sphere, and optionally the features of the present invention that come into contact with them, are textured to facilitate robust fixation. Such textures include, but are in no way limited to, #7 to #20 grit blast, Tecotex™, knurling, and other means known in the art for effectively increasing the surface area of a smooth surface.

The spherical articulation feature of the split sphere enables both tri-axial rotational and single axial translational manipulation of the split sphere with respect to the anchor and along its long axis, as well as simultaneous locking of those degrees of freedom, and an additional axial translational degree of freedom of the articulation post of the cutting tool guide with respect to the articulation aperture feature of the split sphere. Locking is attained by compression of the locking channel feature (see FIG. 171) of the anchor against the spherical articulation feature and, by way of the relief feature of the split sphere, the articulation post feature of the cutting tool guide. The relief feature of the split sphere enables two distinct functions. The relief feature enables elastic compression of the split sphere against the articulation post of the cutting tool in response to force applied to the split sphere by the locking channel feature in response to actuation of the conical lock feature.

Figure 190:
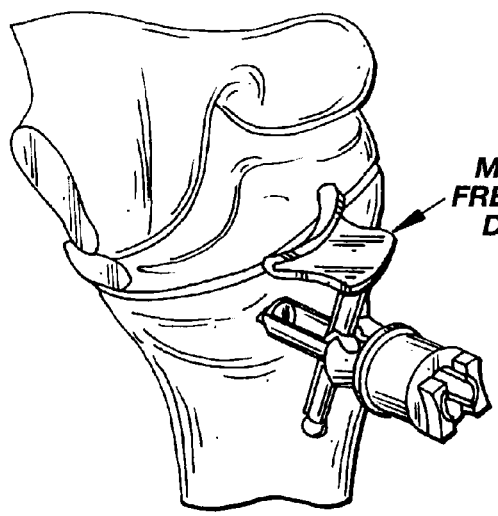
Figure 191:
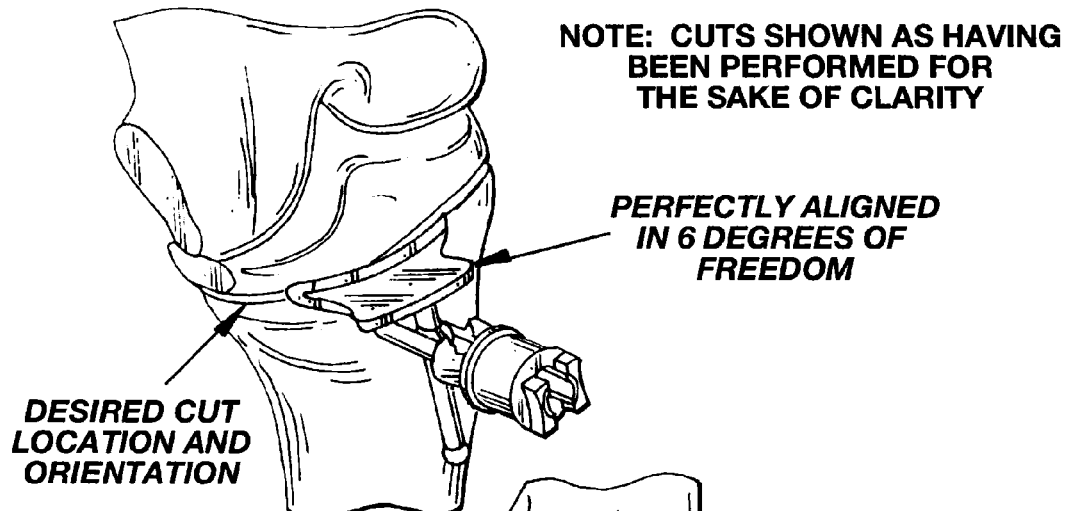

In the context of tibial resection for the embodiment of the present invention shown in FIGS. 190 and 191, the sphere articulates with respect to the anchor in 4 degrees of freedom (anterior to posterior, varus-valgus, internal external rotation, and flexion-extension) while the articulation post, and thereby the cutting tool guide, articulate with respect to the split sphere, and thereby the anchor and bone, in at least one additional degree of freedom (proximal-distal). The second function of the relief feature is to optionally allow the articulation post of the cutting tool guide to be rotationally keyed to the split sphere to enable the split sphere and cutting tool guide to be rotated in tandem with respect to the locking channel of the anchor.

In another embodiment of the present invention (not shown), the articulation post of the cutting tool guide could be split along its long axis and coact with an articulation feature on the cutting tool guide to enable mediolateral translation and locking of the cutting tool guide with respect to the bone wherein effective locking of the mediolateral degree of freedom would also be affected by actuation of the cone lock feature in addition to the aforementioned 5 degrees of freedom.

Figure 254:
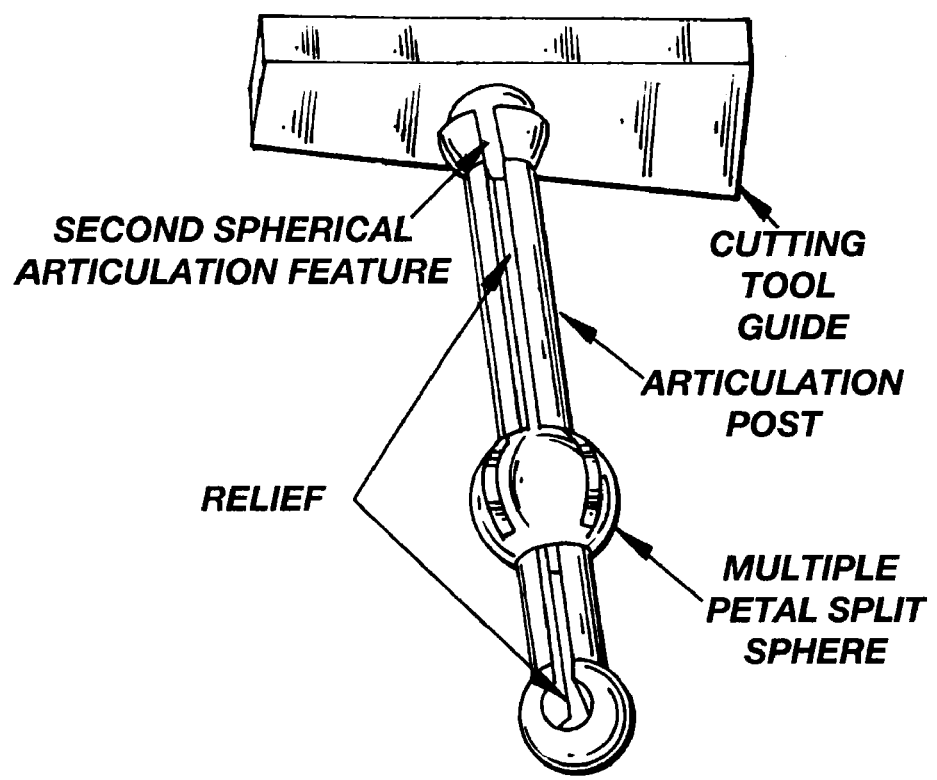

In yet another embodiment of the present invention as shown in FIG. 254, a second spherical articulation feature could be formed integrally with the underside of the cutting tool guide shown in FIG. 171 which would be 'grasped' by a mating spherical locking aperture on the top of the split articulation post which would subsequently allow for continuous, non-incremental manipulation of the cutting tool guide in six, seven, or eight degrees of freedom all a which would be locked by the actuation of a single locking mechanism (see FIG. 254 for an exemplary embodiment). Critically, in one embodiment of the present invention, all of these degrees of freedom are smoothly adjustable (as that term is defined in U.S. Pat. No. 6,685,711 by Axelson, et al which is herein incorporated by reference) to any desired location and orientation and are rigidly and quickly locked by the single actuation of a single locking mechanism that does not cause the cutting tool guide to move with respect to its desired location and orientation.

Figure 176:
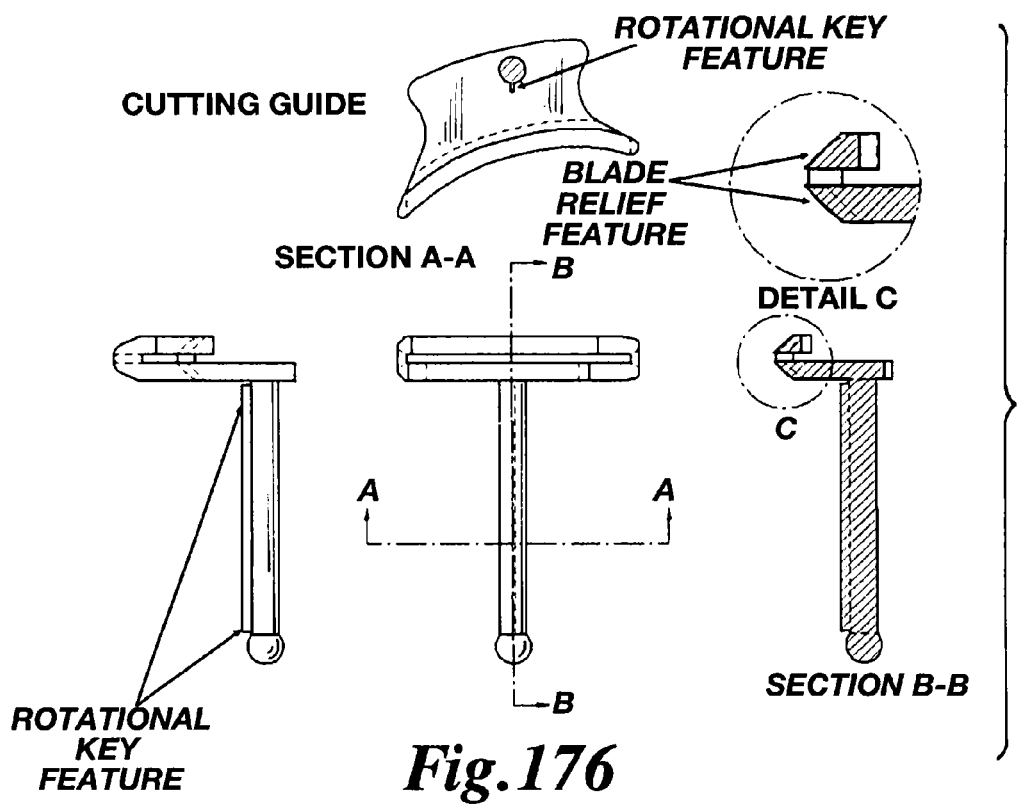

The cutting tool guide (see also FIGS. 171, 176, 193, and 218), in this embodiment of the invention possesses three primary features alone or in combination with the primary components of the present invention including a cutting tool guide surface(s) feature (FIGS. 171, 176, 193, and 218), the articulation post feature (FIGS. 171, 176, 193, and 218), and the sensor (not shown). The cutting tool guide surface(s) takes many forms in different embodiments of the present invention. FIG. 176 shows a fairly conventional oscillating saw blade guide with a saw blade capture feature, which could optionally be a non-integral modularly attachable feature. FIG. 171 clearly shows optional guide gripping and soft tissue accommodating surfaces which enable the surgeon to grasp and manipulate the cutting tool guide to perfectly position the guide in the incision and with respect to the intended implant location and orientation as well as to provide significant surface area for saw blade guidance and contact while minimizing the displacement of soft tissue by the cutting tool guide and thereby minimizing the size of the incision necessary to perform resection. As may be seen in FIG. 191, the soft tissue accommodating feature is intended to contact both the medial and lateral edges of the incision for an anterior approach, or, optionally, in a Quad-Sparing type approach to contact more posteromedial and anteromedial edges of the incision (it should be obvious to one of ordinary skill in the art that soft tissue contact occurs with this embodiment at any incision location and orientation about the knee, spine, or other joint without limitation).

Additional optional features are beneficially added to the embodiments shown. In one embodiment of the present invention, a modularly attachable handle provided to attach to the cutting tool guide could be used to manipulate the cutting tool guide with respect to the desired implant location and beneficially includes extramedullary alignment rod(s) (one extending along the anterior aspect of the tibia from proximal to distal locations and one extending along the medial or lateral aspects of the tibia from proximal to distal enable complete visual alignment as per conventional techniques for varus-valgus and flexion extension alignment) and a depth or sizing stylus, as is known in the art, for contacting the bone and determining cut depth or location and/or implant size. As has been noted in the prior art, the computers facilitating surgical navigation techniques still have a tendency to "crash" and the availability of these features is crucial in avoiding leaving a surgeon "stranded" with a live patient on the table under anesthesia in the event of such a "crash."

In yet another embodiment of the present invention, the cutting tool guide (as shown in FIGS. 194 through 197, and FIGS. 213 and 218) acts to guide a standard drill, pin, or coring drill to either position implements to which a cutting guide is attached, or to create apertures in bone to which the cutting guide is attached. In facilitating techniques more similar to prior art practices, the pins, drills, etc., could be merely fixation means to provide additional stability to the cutting guide's (such as in the embodiment shown in FIG. 171) fixation to the bone. It is of significant utility to utilize the drills, pins, etc., as extensions of the cutting guide surface through the border of the cuts to be made and across the plane of the cut to be made to simultaneously fix the guide and implement the positioning of pinplasty style cutting guide embodiments of the present invention as shown in FIGS. 213 and 218. The articulation post feature coacts with the split sphere feature as previously noted, and, optionally, with the second spherical articulation feature of the previously noted embodiment of the present invention.

Although the sensor feature of this embodiment of the present invention is central to surgically navigated surgery, it will be understood that there are multiple and numerous variations of sensor technologies; features for modularly attaching sensors to cutting tool guides or other components of arthroplasty instrumentation or implants, features for forming the sensors as integral components of instrumentation and implants, that can be combined with this embodiment of the present invention. It will be appreciated that there are various ways in which electromagnetic phenomenon based sensors can be utilized to facilitate and determine bone cutting and/or implant placement. It will also be appreciated that multiple and numerous mechanical fiducial techniques and apparatus can be used in cooperation with the align and cutting guide systems.

The following patents and patent applications describing various surgical navigation system and alignment and cutting guide systems that are beneficially utilized in whole or in part with the embodiments of the present invention are herein incorporated by reference:

U.S. 2004/0122436, U.S. 2003/0069591, U.S. 2004/0039396, U.S. 2004/0153083, U.S. Pat. No. 5,810,827, U.S. Pat. No. 6,595,997, U.S. 2003/0069585, U.S. 2003/0028196, JP74214-2002, U.S. 2003/0208122, U.S. Pat. No. 6,725,080, U.S. 2004/0122305, U.S. Pat. No. 6,685,711, U.S. 2004/0153085, U.S. 2004/0152970, U.S. Pat. No. 6,694,168, WO04100758, WO04070580, WO04069036, U.S. Pat. No. 5,799,055, U.S. Pat. No. 6,236,875, U.S. Pat. No. 6,285,902, U.S. Pat. No. 6,340,363, U.S. Pat. No. 6,348,058, U.S. Pat. No. 6,430,434, U.S. Pat. No. 6,470,207, U.S. Pat. No. 6,477,400, U.S. Pat. No. 6,491,699, U.S. Pat. No. 6,697,664, U.S. Pat.

No. 6,701,174, U.S. Pat. No. 6,711,432, U.S. Pat. No. 6,725,080, U.S. Pat. No. 6,796,988, and U.S. Pat. No. 6,827,723.

Another feature of the embodiments of the present invention is an elegant quick release mechanism enabling extremely rapid unlocking and removal to the cutting tool guides from the anchor before or after completion of bone resection. As noted in FIG. 196, the act of releasing the cutting tool guide from the anchor is as simple as the surgeon squeezing the release tabs together, manipulating the locking sleeve from lock mode to drag mode, and simply removing the cutting tool guide. This level of simplicity truly facilitates the easy instruction and operation of this embodiment of the present invention, even permitting surgeons to be able to pick up the surgical instrument and intuitively understand the proper use of the instrument without instruction.

Figure 192:
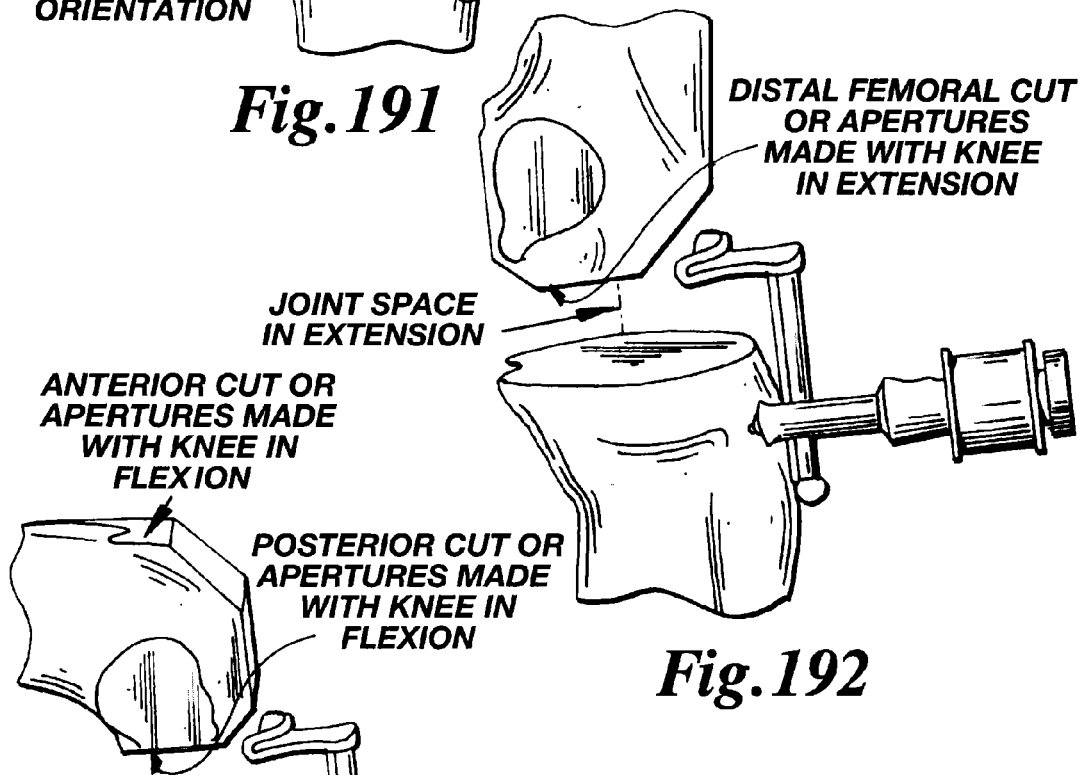
Figure 193:
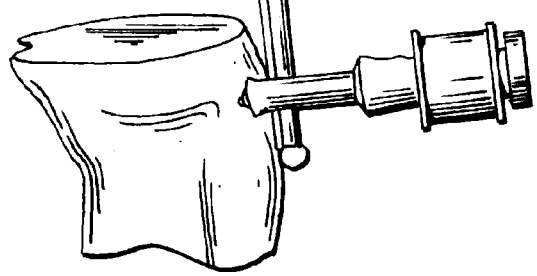
Figure 208:
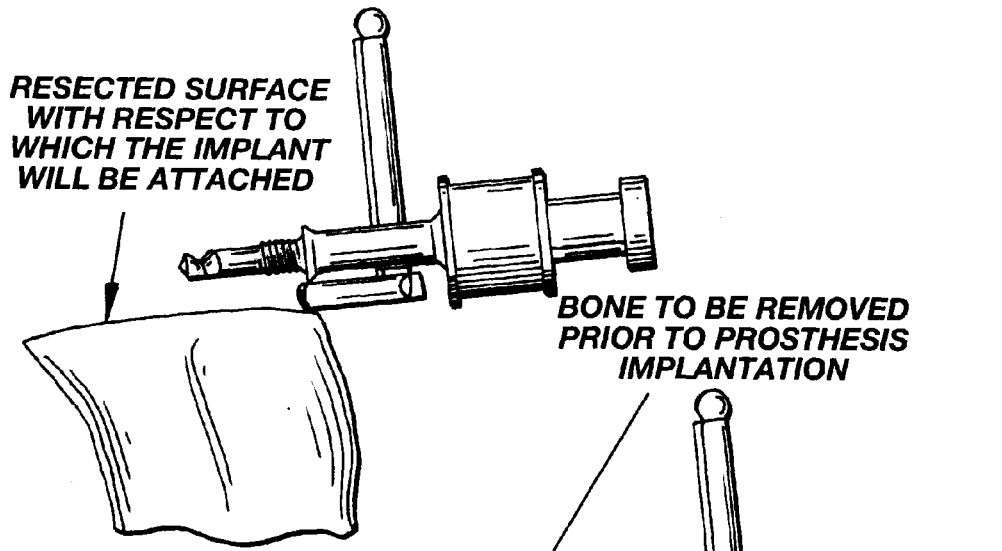
Figure 209:
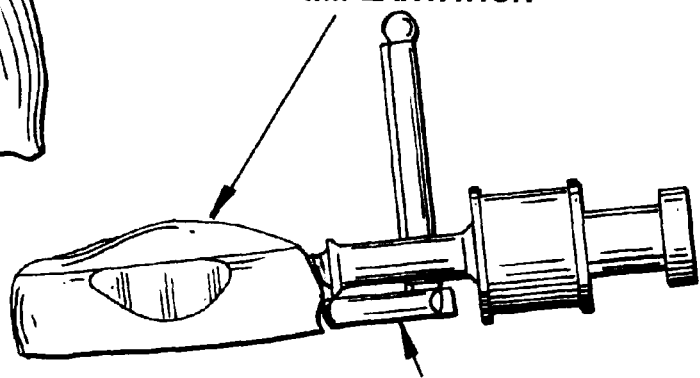
Figure 210:
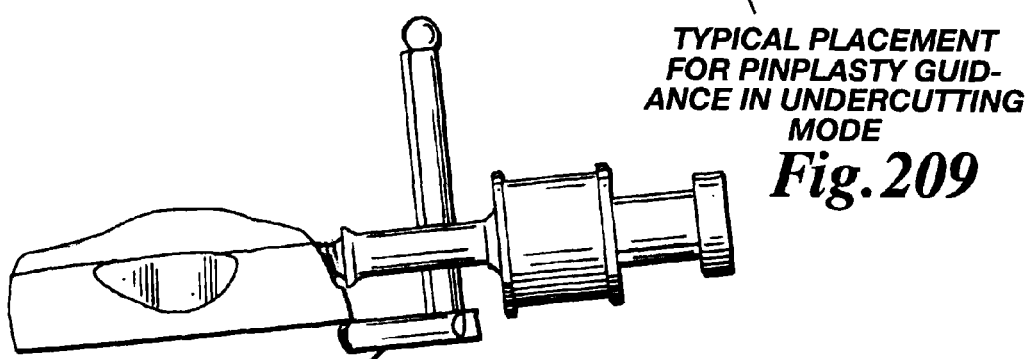

FIGS. 192 and 193 represent another embodiment of the present invention wherein the same cutting tool guide utilized to cut a first bone (in the example shown, it's the tibia) is located and oriented to cut a bone that opposes the first (in the example shown, it's the femur). As an especially useful ability for TKA or Unicondylar Knee Arthroplasty, the femur may be manipulated into positions of different degrees of flexion or extension to enable the cutting tool guide to be aligned with the desired location of different resected surfaces. FIG. 192 shows the device positioned properly to create a distal resection, while FIG. 193 shows the femur oriented to allow the cutting tool guide to be manipulated to cut the posterior cut, the anterior cut, and/or the chamfer cuts with respect to which the implant(s) are fixed. This embodiment of the present invention and the associated techniques that are facilitated by use of this embodiment of the present invention are easily and beneficially applied to the other embodiments of the present invention described herein.

The methods of using the embodiments of the present invention are quite simple. Attach the anchor to the bone, attach the split sphere and the cutting tool guide to the anchor, align the cutting tool guide with respect to the desired implant location and orientation as indicated and/or tracked by non-surgically navigated or surgically navigated system(s) and/or indicia, lock the cutting tool guide in said location and orientation, remove boney material to create a resected surface with respect to which an implant will be fixed to bone, remove the anchor from the bone, and attach the implant with respect to the bone; wherein the step of aligning the cutting tool guide further includes the step of manipulating the cutting tool guide location and orientation in four, five, six, seven, or eight degrees of freedom all of which are locked by the actuation of a single locking mechanism.

FIGS. 194 through 197, 202 and 205

FIGS. 194 through 197, 202 and 205 show yet another embodiment of the present invention. In this embodiment, the cutting tool guide is configured to guide the placement of drills, pins, punches, coring drills, etc., to create apertures in bone which dictate implant location and orientation and to which cutting guides are subsequently attached (this shall be referred to as a "drill guide"). FIG. 194 shows the drill guide that is located and oriented with respect to the desired implant location and orientation in the same manner described for the embodiments of present invention described above for FIGS. 171 through 186, 190-197, 202 and 205.

In yet another embodiment of the present invention, FIG. 195 and FIGS. 202 and 205 show the cannulated style pinplasty cutting guide for use in conjunction with the coring drill (see FIGS. 195, 197 and 202). One of the principal benefits of utilizing a cannulated or coring drill is that the volume of living tissue that is disrupted by the surgical procedure is minimized thereby minimizing the amount of damage that must heal postoperatively for overcutting, or split pin style pinplasty. As minimizing postoperative recovery time and return to function are the core objectives of MIS arthroplasty, every opportunity to minimize the damage to soft and osseous tissue is beneficially taken advantage of by these embodiments of the present invention.

In use, the drill guide is manipulated into the desired location and orientation as hereinbefore described and locked or pinned in place. The coring drill (shown in FIGS. 195 through 197), twist drill, punch, pin, nail, screw, or other bone penetrating feature is used create the apertures in the bone (shown in FIG. 202) to which the cutting guide is subsequently attached. The cutting guide then coacts with the cutting tool to partially or completely create the desired resection(s).

FIGS. 207 through 212

Figure 211:
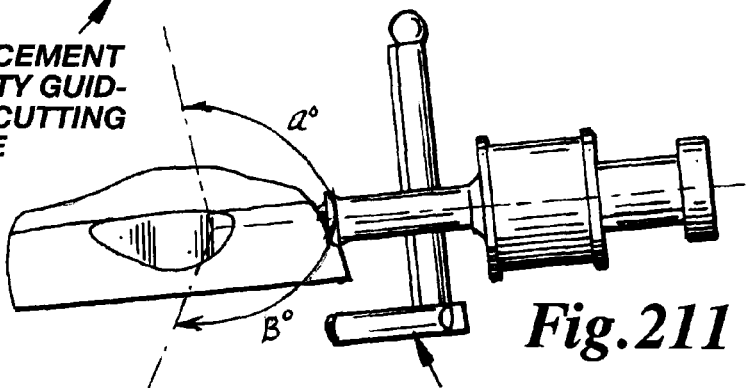

FIGS. 207 through 212 show another embodiment of the present invention wherein the anchor is attached to a face of a bone to be subsequently removed prior to fixation of the prosthesis with respect to the resected surface(s). In comparing FIGS. 207 and 208, it is clear that the anchor is fixed to bone to be replaced by the implant. FIGS. 209 through 212 show the modes (undercutting, overcutting, conventional, and split pin, respectively) of cutting guide embodiments of the present invention. FIG. 211 makes it clear that the axis of the anchor may vary significantly with respect to the axis(es) of the drill guide or other cutting tool guide embodiments of the present invention (FIG. 211 makes it clear that the axis may vary by an included angle of greater than 180 degrees).

One advantage of the embodiments of the present invention is the low profile nature of the embodiments enabling the anchor feature and the cutting tool guide feature to both be positioned adjacent to bone within the same incision thereby avoiding the additional trauma and cosmesis compromise inherit in having to create a separate incision for the anchor feature as necessitated by the work of Axelson, et al in U.S. Pat. No. 6,685,711 by Axelson, et al which is herein incorporated by reference. FIG. 207 describes the cutting tool guide as being capable of being located immediately above, immediately below, or in fact straddling the anchor location to facilitate this optional use of the present invention.

FIGS. 213 and 218

FIGS. 213 and 218 show yet another embodiment of the present invention wherein the cutting tool guide is both a saw blade guide and a drill or pin guide. This embodiment of the present invention could also be described as a hybrid pinplasty and conventional cutting guide as the placement of the pins in essence extend the cutting tool guiding surfaces of the cutting guide into the bone from a first position located outside the border of the cut to be created to a second location within the border of the cut to be created along an axis(es) that are parallel to the cut to be created. This embodiment of the present invention also makes clear that the pinplasty guide surfaces need not extend along parallel axes, but may instead be divergent or convergent with respect to each other.

A feature of the present invention which differs from some of the other embodiments of the present invention is that the pin or drill of the present invention possesses a flat surface to be aligned in a coplanar fashion with the conventional cutting guide surface(s). Also included within the scope of the present invention would be a cutting guide where the drill or pin guide apertures in the cutting tool guide are not interrupted by the cutting tool guide surface of the cutting tool guide, but posses a minimal wall thickness or a minimal interruption enabling the use of cylindrical pins or drills with guide surfaces for contact with the cutting tool that are only a few thousandths of an inch offset from the cutting tool guide surface. In other words, the centerline of the drill or pin guide apertures are parallel to but offset from the guide surfaces (as indicated in FIG. 213) by an amount generally less than 20% of the diameter of the apertures.

FIGS. 221 and 227

FIGS. 221 and 227 show yet another embodiment of the cutting guides of the present invention. This embodiment could be described as a hollow, divergent, split pin configuration cutting guide. In this embodiment of the present invention, the divergent angle of the pin axes are set to approximately 20 degrees, but divergent angles of up to 130 degrees are considered to be within the scope of the present invention as are pins that coact to form axes that intersect within the border of the resected surface(s) to be created as viewed from a direction normal to the resected surface to be created. One feature of critical benefit to MIS procedures with respect to this embodiment of the present invention is the ability of the split pin to incorporate a stop feature (as shown in FIG. 227) where critical structures such as ligaments, tendons, capsule, veins, arteries, or nerves may be prevented from direct contact with the cutting tool's cutting surfaces by limiting the depth to which the cutting tool may be extended in the direction of those critical structures prior to contacting the stop feature. Another important feature of this embodiment of the present invention is the flexibility of the divergent guide that enables the cutting guide to be squeezed by the surgeon to initially line up and insert the tips of the pin features into the divergent apertures and then push the pins into the location desired. It should also be noted that the two divergent pins could be constructed as independent constructs as opposed to the unitary structure shown in FIG. 221 and optionally provide features for attachment of a bridging feature.

Figure 242:
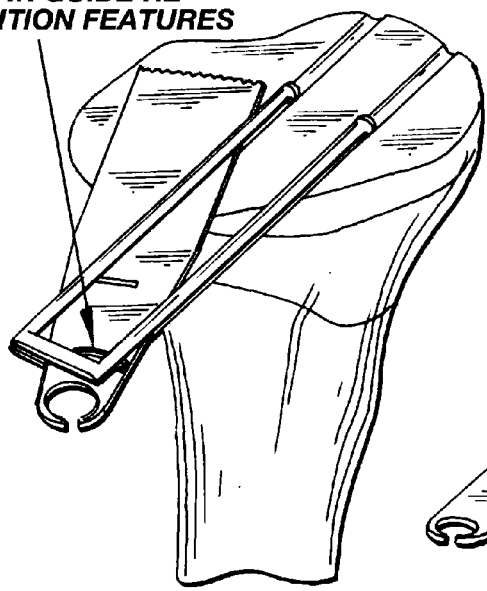

FIGS. 237, 241, and 242

FIGS. 237, 241, and 242 show an embodiment of the present invention that in essence provides for the apertures formed in the bone to act as the cutting guide in coacting with a carriage linked to a saw blade or other cutting tool. Beneficially, the saw blade and carriage (hereinafter referred to as the "cutting tool/pin guide") may be packaged together as an assembly intended for single use only, or a limited number of uses, and/or as sterile or non-sterile. In essence, the retention feature of the cutting tool/pin guide enables the cutting tool and carriage components to coact to continuous guide the cutting tool as it traverses the surfaces within, along, and about the apertures formed in the bone to create the resected surfaces with respect to which the implant is to be fixed. This embodiment also possesses an effective stop feature preventing the cutting teeth from inducing catastrophic damage to soft tissue structures.

Figure 246:
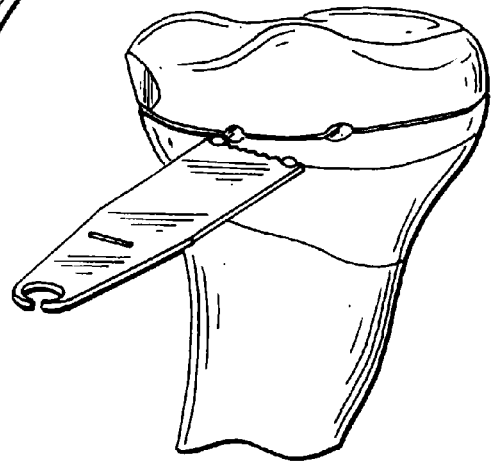
Figure 250:
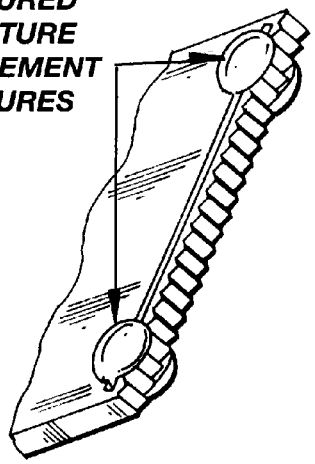
Figure 252:
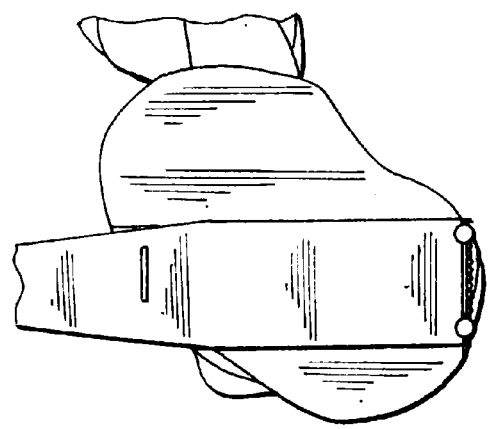

FIGS. 246, 250, and 252

FIGS. 246, 250, and 252 show another embodiment of the present invention wherein the aperture guidance feature of the cutting tool is formed as component of the cutting tool. The independent or linked sphere or bullet features shown in FIG. 250 (and described therein as captured aperture engagement features). A track is formed in the end of the blade such that the aperture guidance feature may articulate therein to an extent greater than the arc or line through which the saw blade is oscillated by the saw. In use, the sphere or bullet features of the cutting tool are inserted into the apertures formed in the bone and manipulated by the surgeon to traverse the axis(es) of the apertures to cut the bone.

FIG. 254

FIG. 254 shows an embodiment of the present invention enabling as many as eight degrees of freedom to be rigidly locked by the actuation of a single locking mechanism. The second spherical articulation feature is critical to this embodiment of the present invention as it enables smooth adjustment and robust locking of three rotational degrees of freedom of the cutting tool guide (shown in a generic form in FIG. 254) with respect to the articulation post as shown in FIG. 254. This embodiment includes the second spherical articulation feature with the mating collet of the articulation post of this embodiment of the present invention the relief and multiple petal split sphere. Although the surgeons will likely place the anchor in a location and orientation enabling the cutting tool guide to be located and oriented with little manipulation, this embodiment of the present invention enables radical realignment to be performed as the angle between the articulation post and the cutting tool guide may reside anywhere within a 150 degree included conical section swept about the center of the second spherical articulation feature's center point.

Alternative Embodiments & Fields of Use

The surgical application of the above described embodiments of the present invention for anchor-cutting tool guide-linkage type devices have been predominantly demonstrated in the context of tibial resection in TKA or Unicondylar Knee Arthroplasty. It should be noted that the scope of the present invention is in no way limited to this field of use and therefore several examples of additional fields of use shall be herein provided to demonstrate the significant utility of this invention.

For years, spinal surgeons have struggled with the demands of polyaxial screw based pedicle screw technologies in that having the sphere formed as an integral part of the anchoring screw prohibits axial adjustment of the rods with respect to the screw spheres. The design of the anchor of this embodiment of the present invention is beneficially modified by shortening the relative length of the locking channel and providing split spheres positionable along the rod. The external surfaces of the anchor opposing the interior surfaces of the locking channel would be threaded, beneficially with a conical thread, to which a mating threaded cap is threadably attached. In use, the pedicle screws of the present invention would be attached to the vertebral bodies by way of the pedicles as per standard techniques, including placement by way of the present invention for screw placement under surgical navigation guidance. Next, transversely oriented rods with split spheres along their lengths would be interconnected with the locking channel by contacting the spherical articulation feature of the split sphere with the interior surfaces of the locking channel. In the clinical application of scoliosis reduction and/or fusion, the spine would then be reduced (or straightened, stretched, and generally realigned to a desirable configuration) and the threaded cap would be actuated to move distally (toward the tip of the screw that first penetrates the bone) lock the spheres and thereby the rods in the desired location and orientation within the locking channel of the pedicle screw of the present invention. A second threaded cap could beneficially be implement with this technique to additionally lock the split sphere feature of the present invention in place by advancing it along the pedicle screw along external threads in a proximal direction. The proximal end of the anchor would beneficially include frangible ends that could be trimmed after complete locking to reduce the profile (the extent to which the device displaces or traumatizes soft tissue and/or bone) of the assembled device and therefore enhance its minimally invasive nature.

It should further be noted that the locking channel could be partially countersunk or counterbored into the bone to further reduce the extent to which the anchors extend beyond the naturally occurring bone surfaces further enabling the rods to be positioned in close proximity to the bone (thus reducing intraoperative invasion requirements for implantation of the system). Of specific interest in implantable embodiments of the present invention, the use of a biocompatible adhesive to permenantly lock the respective members of the assembly in position could be used to further facilitate permanent, robust locking. Additionally, the surfaces of the coacting features could be textured or even porous to affect improved fixation with or without the use of adhesive compounds. Commercially available materials and/or processes to provide textured or porous surfaces and/or materials include the publicly available material on TecoTex™ and Trabeculite™ from Tecomet, Inc. of Connecticut and Trabecular Metal™ distributed by Zimmer, Inc. of Warsaw, Ind. Furthermore, the adhesive could be used to coat the assembly and thereby provide smooth external soft tissue contacting surfaces to avoid the well understood soft tissue reaction to stiff, sharp implant geometries coming into contact with soft tissue and thereby eliciting some level of foreign body response by living soft tissue manifest, for instance, by encapsulation of the offending implant by fibrous tissue.

Although specific examples of applying the embodiments of the present invention to femoral resection in knee surgery were given in FIGS. 192 and 193, clearly this embodiment of the invention has significant utility where the anchor is attached to the femur for femoral resection, as opposed to being attached to the tibia for femoral resection. This embodiment of the present invention will beneficially implement the principals of operation utilized in any of the other embodiments of the present invention described herein including, but not limited to, the following: (a) attachment of the anchor feature to bone to subsequently be removed; (b) embodiments of the cutting tool guide as a drill guide, saw blade cutting guide, punch guide, pin guide, hybrid drill guide/saw blade cutting guide, drill guide for screw or other fixation mechanism placement guide; (c) four, five, six, seven, or eight degrees of freedom locked by the actuation of a single locking mechanism; (d) attachment of the anchor to bone along an axis "above" or "below" the cuts to subsequently be made with respect to which the implant will be attached; (e) attachment of the anchor to the femur wherein the cutting tool guide is manipulated to be located and oriented with respect to the tibia to facilitate tibial resection to create cuts with respect to which an implant will be attached.

The requirements for effective femoral resection are quite different from tibial resection given the geometry of the implant surfaces to be fixed with respect to the femur in knee surgery and the soft tissue anatomy in and about the knee joint adjacent the femur. This creates opportunities to implement the present invention to even greater benefit. For instance, in a Quad-Sparing approach (such as the technique popularized by Zimmer, Inc.), a more medialized incision is utilized thus exposing femoral anatomic structures located more medially than a more standard medial para-patellar incision which facilitates insertion of cutting tools from a more generally mediolateral direction than the "head on" approaches favored in the standard approaches. Thus, the cutting tool guide positioned by the embodiment of the present invention could be similar to those taught by U.S. Pat. No. 5,514,139, and U.S. Pat. No. 5,810,827 (which are both incorporated herein by reference) wherein at least one continuous or discrete multiplanar guide surface(s) possessing cutting guides are positioned along the medial or lateral sides of the femur and are secondarily fixed in position by first locking and then pinning or screwing the cutting tool guide in place. A cutting tool of any kind known in the art may then be traversed along the guide surface(s) while cutting the bone to receive the femoral implant.

Further, cutting tool guides possessing both guide surfaces located to the medial or lateral sides of the femur and further "wrapping around" the more distal border of the femoral surface to be cut (as may be seen in U.S. Publ. Application No. 2004/0153066 in FIGS. 27 through 32 by Coon, et al. which application is herein incorporated by reference) are also included in the scope of the present invention. The Coon et al. work could be further modified to implement the overcutting, undercutting, hollow pin, split pin, or hollow split pin embodiments of the present invention wherein the cutting guides are attached to the bone subsequent to creation of the apertures or wherein the hybrid methodology described above is used in conjunction with the cutting tool guide shown in FIGS. 213 and 218 or with the other embodiments of the present invention. Furthermore, benefit is obtained by limiting the number of cutting guide surfaces per guide to those corresponding to resected surfaces accessible through the incision with the knee positioned at different locations within its range of motion (such as one guide to perform the more anterior cuts with the leg somewhere between −10 and 45 degrees of flexion and one guide to perform the more posterior cuts with the leg somewhere between 60 and 145 degrees of flexion) thus facilitating minimally invasive resection and implantation incision such as the modular or unitary guide rail shown in FIG. 45 of this application optionally including the "wrapping around" guide surfaces of Coon, et al.

Benefit will also be found in an embodiment of the present invention where a bracket is positioned and fixed to the side of the femur wherein the bracket is configured to receive cutting guide surfaces as illustrated in U.S. Pat. No. 6,695,848 (which is herein incorporated by reference) FIGS. 13A through 15C by Haines, the applicant for the present invention.

Another embodiment of the present invention would be the implementation of the cutting tool guide shown in FIGS. 53 through 56 of U.S. Pat. No. 6,702,821 (which is herein included by reference) by Bonutti and/or utilizing the anchor feature of the present invention as a substitute for the anchor number 1338 in FIG. 93 of U.S. Publ. Application No. 2003/0028196 (herein incorporated by reference) also by Bonutti.

Figure 33:
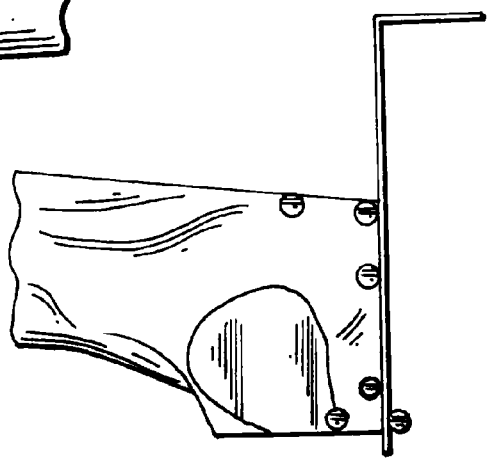
Figure 34:
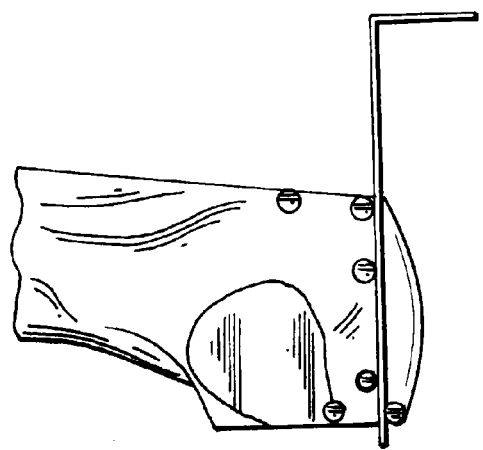
Figure 35:
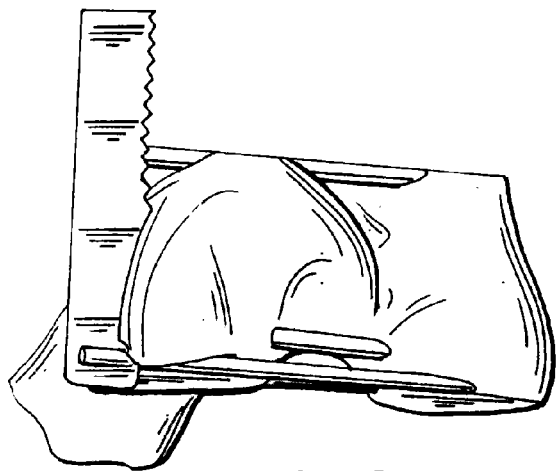
Figure 36:
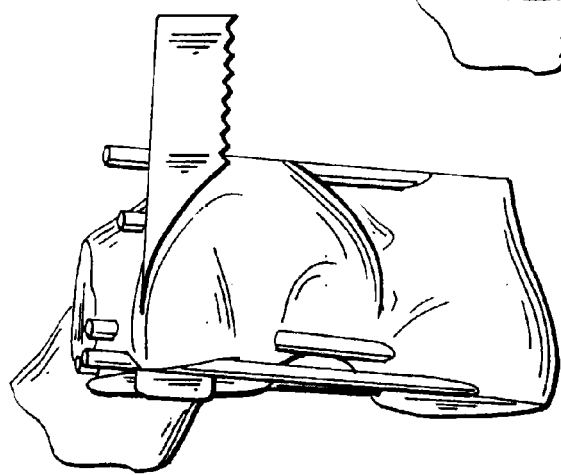
Figure 37:
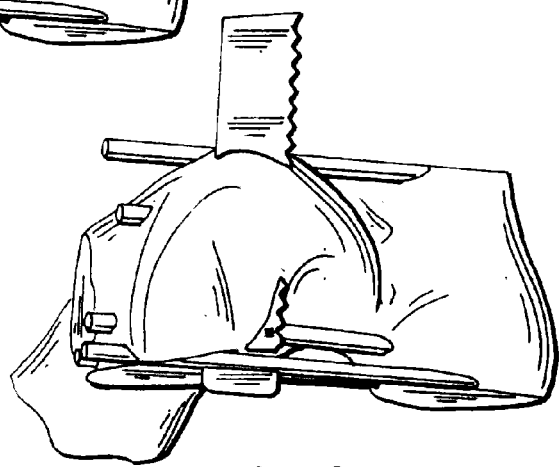
Figure 38:
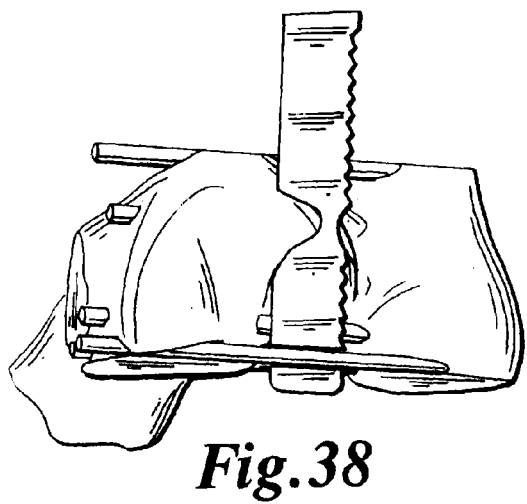
Figure 39:
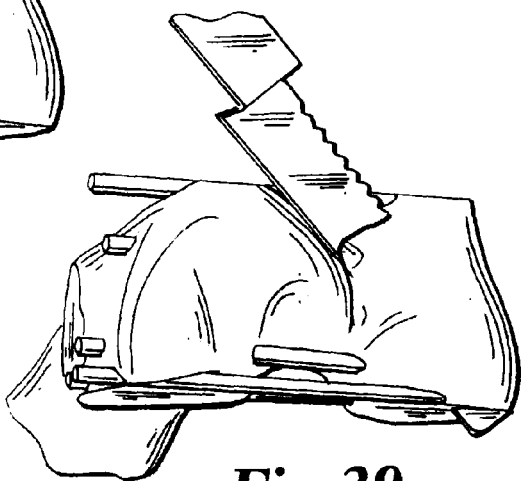
Figure 40:
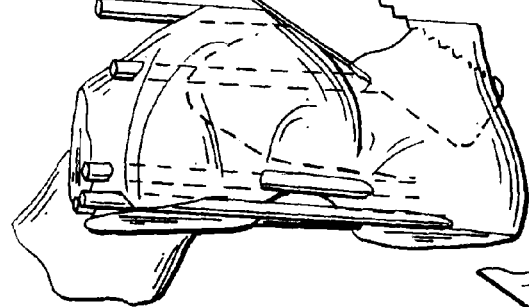
Figure 41:
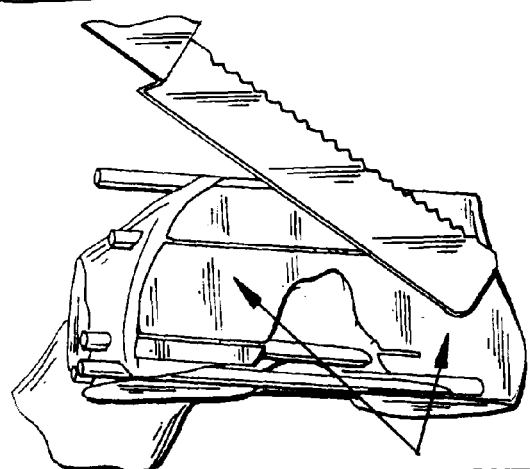
Figure 46:
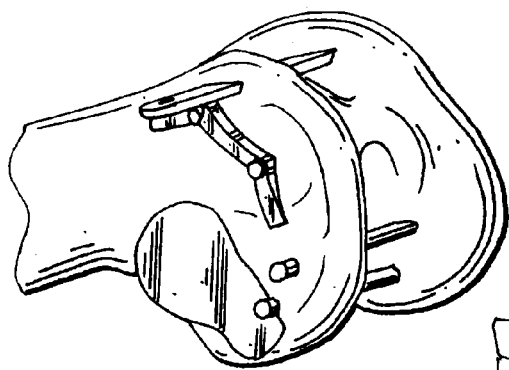
Figure 47:
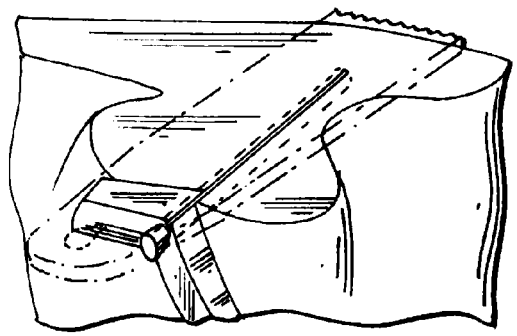
Figure 48:
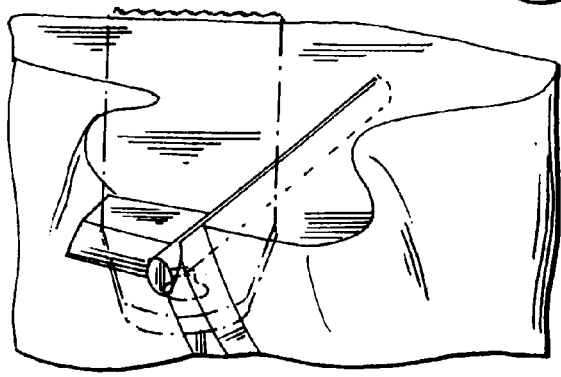
Figure 49:
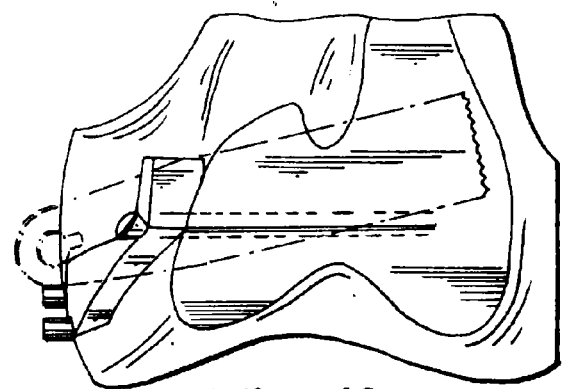
Figure 53:
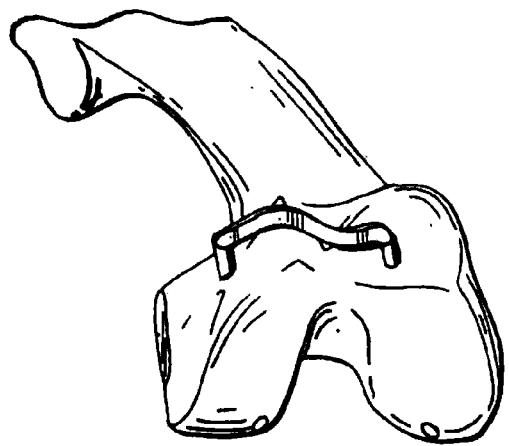
Figure 54:
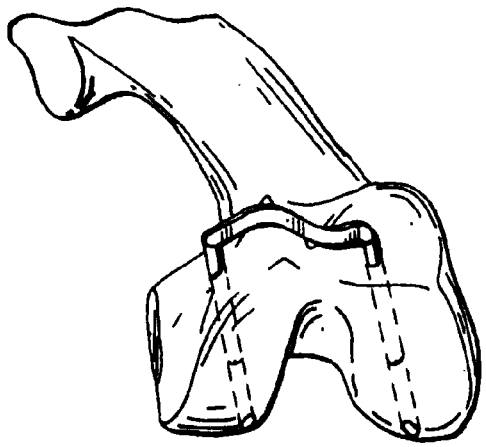

In yet another embodiment of the present invention, the cutting tool guide could be implemented to create apertures in bone to be removed, such as the bone removed by the anterior chamfer cut and the posterior chamfer cut, wherein the long axis of the apertures extends in a generally mediolateral direction such as the apertures to which the pin shown in FIG. 33 of this application which is imbedded in bone to be removed by the creation of the anterior chamfer cut (since the anterior cut, posterior cut, and distal cut coact to define both the implant location, orientation, and size, the chamfers may be completed by conventional means without loss of the benefits of the present invention when applied to conventional total condylar femoral implants most commonly used with flat planar fixation surfaces for apposition and fixation with respect to complementary resected bone surfaces).

For curvilinear fixation, adaptation of these concepts to determine the location and orientation curvilinear or "cortical" prostheses, BMO prostheses, and or Porous Prostheses (as shown and described in the co-pending applications by the inventor of the present invention) is readily apparent.

Benefit will also be derived from adapting the present invention to act as what could be described as an abbreviate intramedullary rod type anchor of generally cruciform punch configuration as described in U.S. Publ. Application No. 2003/0069591 (herein incorporated by reference) for FIG. 46B by Carson et al.

Benefit will also be derived from adapting the present invention as a substitute for the anchor feature of FIGS. 1, 2, and 5 through 8 of U.S. Publ. Application No. 2004/0153083 (herein incorporated by reference) by Nemec et al. wherein the anchor is fixed to the bone through an incision other than the incision in which the cutting tool guide and/or cutting tool is positioned adjacent the bone to facilitate resection.

Another embodiment of the present invention may be illustrated by the use of the present invention in conjunction with the instrumentation and prostheses of U.S. Publ. Application No. 2003/0212403 (herein incorporated by reference) by Swanson, which describes devices for use in a what is essentially a pure medial or pure lateral surgical exposure approach to tibial, femoral, and patellar resection and implantation.

Another embodiment of the present invention may be illustrated by way of combining the apparatus and methods of copending provisional applications (previously incorporated by reference) to facilitate both the improved longevity of the prosthesis and improved rate of patient recovery post operatively.

Another embodiment of the present invention may be illustrated by the use of the present invention in conjunction with the instrumentation and prostheses of U.S. Patent Application No. 2003/0130665 (herein incorporated by reference) by Pinczewski, et al, which describes devices for use in a what is essentially a form of kinematic resection. It is clear the present invention has significant utility as a means for locating and orienting the cutting tools, cutting guides, and other surgical implements of Pinczewski, et al both in kinematic resection and non-kinematic resection based techniques. Very similarly, another embodiment of the present invention may be illustrated by use of the present invention in conjunction with the instrumentation and prostheses of U.S. Pat. No. 6,482,409 by Engh, et al, (herein incorporated by reference) which describes devices for use in what is in essence anothe form of kinematic resection.

Another embodiment of the present invention may be illustrated by the use of the present invention in conjunction with the instrumentation and prostheses of U.S. Patent Application No. 2003/0208122 (herein incorporated by reference) by Melkent, et al, which describes devices for use in a what is essentially a freehand surgically navigated method for pin, screw, drill, or other bone displacing implements. As shown in FIGS. 8-11 of copending U.S. Provisional Patent Application No. 60/551,080, a similar method is demonstrated that in use in conjunction with the Melkent, et al patent provide significant benefit in terms of ease of use and reduced intraoperative time. The copending application demonstrates that once the surgically navigated drill guide of FIGS. 8-11 of that application are properly located and oriented with respect to the desired prosthesis location and orientation while being tracked by indicia in as many as 6 degrees of freedom, the sharp leading tip of the cannulated drill guide is impacted into the bone such that the tip of the drill which is subsequently inserted through the cannulae first contacts bone inside the tip of the cannulated drill guide. This embodiment of the present invention mitigates opportunity for the drill tip to "walk" prior to penetrating the bone thus avoiding implant malalignment due to one of the greatest short comings of prior art joint and spinal arthroplasty systems. The implementation of coring drills, twist drills, punches, nails, screws, cannulated screws, pedicle screws, and other bone displacing tools is considered to be within the scope of the invention.

Another embodiment of the present invention may be illustrated by the use of the present invention in conjunction with the instrumentation and prostheses of as shown in the same copending U.S. Provisional Patent Application No. 60/551,080, which describes devices for pivotable guide surfaces. The embodiments of the present invention are beneficially applied to the creation of the bone aperture features shown therein and could further be implemented to guide the forstner style drill to facilitate the "guideless cutting" technique described by FIGS. 40 through 44 and the written description associated therewith.

Another embodiment of the present invention may be involves the use of a cutting tool guide in conjunction with the hybrid drill/pin guide of FIGS. 213 and 218 for femoral resection. In this embodiment, the anchor-cutting tool guide-linkage device would be positioned adjacent the border of a resected surface to be created wherein the cutting tool guide possesses the "wrap around" feature herein described and the drill or pin guide features of FIGS. 213 and 218. In this embodiment of the present invention, the cutting tool guide would be positioned as herein described and the pin-like cutting guide features extended or driven into the bone through, along, across, over, or under the cut surface to be created. Of particular interest, positioning the cutting guide surfaces both medially and distally (or optionally laterally and distally) across less than ½ of the mediolateral width of the resection to be made and extending the pin-like cutting guide features a distance of at least $\frac{1}{3}^{rd}$ of the width of the resection to be made provides for excellent guidance of the cutting tool while enabling minimal incisions.

Yet another embodiment of the present invention includes alternative locking mechanisms to affect fixation of the split sphere feature of the present invention with respect to the anchor. Any mechanism which adheres to the requirement that the sum of the force moment couples acting about the center of mass of the cutting tool guide is considered to be within the scope of the present invention including, but not limited to the following: a) forceps type mechanisms applying force to the locking channel feature, b) vice grips type mechanisms applying force to the locking channel feature, c) surgical towel clamp type mechanisms applying force to the locking channel feature, d) lockable pliers type mechanisms applying force to the locking channel feature, e) cam locking type mechanisms applying force to the locking channel feature, f) latchig type mechanisms applying force to the locking channel feature, g) bolting type mechanisms applying force to the locking channel feature, h) conical thread type mechanisms applying force to the locking channel feature, i) wedge type mechanisms applying force to the locking channel feature, j) pivot type mechanisms applying force to the locking channel feature, k) and radially actuated type mechanisms and/or mechanisms where rotational motion, about or substantially about or in predefined relation to the locking channel feature (such as a locking channel the extends along a first axis parallel to the central axis of the anchor feature and then bends in a second direction to form a "divergent section" wherein the locking mechanism acts on the diverging section to facilitate ease of use) applies force to the locking channel feature. It should be noted that although the locking channel feature is shown as being substantially "female" in nature to its interaction with the split sphere as being substantially "male", these roles could beneficially be reversed wherein the split sphere feature would be provided as the "female" component with locking affected by the expansion of the "leaves" of the "male" version of the locking channel.

Another embodiment of the present invention further facilitating ease of use and accuracy of implant location and orientation entails referencing the bone apertures described herein with a surgically navigated probe to verify the alignment of the bone apertures with respect to a desired location and orientation of the implant prior to creation of the resected surface. If an error is detected in the alignment of a single aperture, where a second aperture is properly aligned, a surgically navigated drill guide with a probe for referencing the properly aligned second aperture may be used to create a corrected aperture. If an unacceptable error is detected in both apertures, a plurality of pins may be provided wherein there are a plurality of lines of contact constituting a corrected plane of resection by providing cutting tool guide surface that are non-parallel to the axis of the apertures into which the pins are inserted. In this way, the malaligned apertures may be used as to hold or support the cutting guide that can correct for the malalignment of the apertures.

Another embodiment of the present invention of particular utility involves modification of the drill tip feature of the anchor of the present invention shown in FIG. 171. In a first embodiment, the drill tip takes the form of a cannulated or coring drill wherein the cannulation extends from the leading tip of the drill cutting teeth with the tip back through some or all of the anchor thread to minimize trauma to living bone. In second embodiment, minimized trauma and improved ease of use are facilitate by offering a truncated version of the anchor feature wherein the cannulated coring drill type anchor would be made to be "self tapping" by shortening the anchor feature so that its distal most tip possess threads that are interrupted by the coring drill cutting teeth or where the teeth interrupt the leading edge of a smooth shaft leading the the threads. This second embodiment would minimize trauma by limiting the penetration of the anchor feature into bone to perhaps 25 mm or less, and preferably 5 mm to 10 mm, minimizing the displacement of living bone, and facilitating quick, free hand or semi-free hand attachment of the anchor feature to the bone in a robust manner.

The complete disclosures of the patents, patent applications and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein.

What is claimed:

1. A method for implanting an orthopedic prosthesis during a knee athroplasty surgery comprising:

creating a plurality of apertures during the knee arthroplasty surgery, the apertures extending into a bone from a position that intersects a peripheral rim border that externally delineates a resected surface to be created in the bone that defines a surface shaped to interface with a corresponding fixation surface of the orthopedic prosthesis, wherein the fixation surface is in a generally back to back relation to an articulation surface of the orthopedic prosthesis positioned for contacting a second orthopedic prosthesis;

for each of the apertures, inserting a pin from a position outside the border of the resected surface into that aperture, such that the pin extends along an axis parallel to the resected surface with a distal end of the pin positioned within the border of the resected surface;

utilizing a cutting instrument to create the resected surface wherein the cutting instrument includes at least one surface that engages at least a portion of at least a line of contact on at least two of the pins that define a plane that is parallel with the resected surface; and operably attaching the corresponding fixation surface of the orthopedic prosthesis to the resected surface.

2. A method of performing knee arthroplasty comprising:

creating a plurality of apertures in a bone during the knee arthroplasty, each aperture having a cross section defined perpendicular to an axis of the aperture that intersects a plane of a resected surface to be created in the bone and also intersects a peripheral rim border that externally delineates the resected surface;

inserting a pin feature into each of the plurality of apertures;

creating the resected surface by guiding a cutting tool along at least a line of contact of the pin features; and attaching a fixation surface of an implant to the resected surface, wherein the fixation surface is in a generally back to back relation to an articulation surface of the implant positioned for contacting a second implant.

3. A method of implanting a first orthopedic prosthesis during knee arthroplasty surgery, the first orthopedic prosthesis having at least one bone fixation surface in a generally back to back relation to an articulation surface for contacting a second orthopedic prosthesis, the method comprising:

aligning a cutting tool guide with respect to the first bone in a pre-defined relation to a desired implant location and orientation of the bone fixation surface of the first orthopedic prosthesis during the knee arthroplasty surgery, the cutting tool guide possessing a plurality of guide apertures to guide the introduction of a first cutting tool into the first bone;

for each of the plurality of guide apertures, engaging the first cutting tool with the guide aperture and plunging the first cutting tool from a first position beyond an external surface of the first bone to a second position within the external surface of the first bone to create a plurality of bone apertures, the first position and the second position of defining an axis for that bone aperture which is parallel to the desired implant location and orientation;

for each of the apertures, inserting a pin into that bone aperture such that the pin extends along the axis of the bone aperture;

engaging a second cutting tool along at least a line of contact on at least two of the pins to create a resected surface with respect to which a bone fixation surface of the first orthopedic prosthesis is to be attached; and operably attaching the bone fixation surface of the first orthopedic prosthesis to the first bone in predetermined relation to the resected surface such that the bone fixation surface of the first orthopedic prosthesis is positioned at the desired implant location and orientation and the articulation surface of the first orthopedic prosthesis is positioned for contacting with the second orthopedic prosthesis, wherein the bone apertures have cross sections defined perpendicular to the axis of each bone aperture that intersect a plane of the resected surface, and wherein the bone apertures interrupt the resected surface.

4. The method of claim 3 wherein the bone fixation surface is fixed to the first bone directly to the resected surface.

5. The method of claim 3 wherein bone cement is used to fix the bone fixation surface in pre-determined relation to the resected surface.

6. The method of claim 3 a flowable mass is injected through at least one of the bone apertures and into contact with the resected surface and the planar bone fixation surface after attachment of the first orthopedic prosthesis to the first bone.

7. The method of claim 6 wherein the flowable mass is selected from the set consisting of: bone cement, slurry, allograft, curable fluid, antibiotic, cytokine regulating osteobiological compound, adhesive, or any combination thereof.

8. The method of claim 3 wherein the cutting tool guide is connected to the first bone by a linkage and is manipulated and locked with respect to the bone in at least four degrees of freedom all of which are locked by uniactuation of a single locking mechanism.

9. The method of claim 3 wherein the first bone is selected from the set consisting of one of a tibia, a femur, a patella, or a vertebral body.

10. The method of claim 3 wherein the pins are interconnected on proximal ends of each pin by a bridge adapted to be located externally of an external surface of a bone, wherein the bridge also coacts with the second cutting tool to create the resected surface in the step of engaging the second cutting tool.

11. The method of claim 10 wherein the bridge is contoured to approximate a shape of a peripheral rim border of the resected surface and a contoured surface of the bridge is positioned generally adjacent the border.

12. The method of claim 3 wherein the pins and the first cutting tool are the same implement and the steps of plunging the first cutting tool and inserting the pins are accomplished simultaneously.

13. The method of claim 3 further comprising the step of attaching a fiducial to the first bone to which the implant will be attached to determine a desired implant location and orientation prior to the step of aligning the cutting guide tool.

* * * * *